US012077594B2

(12) United States Patent
Kastelein et al.

(10) Patent No.: US 12,077,594 B2
(45) Date of Patent: Sep. 3, 2024

(54) IL2RG BINDING MOLECULES AND METHODS OF USE

(71) Applicant: Synthekine, Inc., Menlo Park, CA (US)

(72) Inventors: Robert Kastelein, Menlo Park, CA (US); Deepti Rokkam, Menlo Park, CA (US); Patrick J. Lupardus, Menlo Park, CA (US); Sandro Vivona, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 24 days.

(21) Appl. No.: 18/006,525

(22) PCT Filed: Aug. 5, 2021

(86) PCT No.: PCT/US2021/044602
§ 371 (c)(1),
(2) Date: Jan. 23, 2023

(87) PCT Pub. No.: WO2022/031884
PCT Pub. Date: Feb. 10, 2022

(65) Prior Publication Data
US 2023/0272089 A1  Aug. 31, 2023

Related U.S. Application Data

(60) Provisional application No. 63/136,098, filed on Jan. 11, 2021, provisional application No. 63/135,884, filed on Jan. 11, 2021, provisional application No. 63/136,095, filed on Jan. 11, 2021, provisional application No. 63/078,745, filed on Sep. 15, 2020, provisional application No. 63/061,562, filed on Aug. 5, 2020.

(51) Int. Cl.
*C07K 16/28* (2006.01)
*A61K 45/06* (2006.01)

(52) U.S. Cl.
CPC .......... *C07K 16/2866* (2013.01); *A61K 45/06* (2013.01); *C07K 2317/22* (2013.01); *C07K 2317/24* (2013.01); *C07K 2317/565* (2013.01); *C07K 2317/569* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| 8,258,268 B2 | 9/2012 | Wu et al. |
| 8,921,528 B2 | 12/2014 | Holt et al. |
| 8,975,382 B2 | 3/2015 | Revets et al. |
| 10,927,186 B2 | 2/2021 | Roobrouck et al. |
| 2006/0024295 A1 | 2/2006 | Brunetta |
| 2010/0297127 A1 | 11/2010 | Ghilardi et al. |
| 2011/0028695 A1 | 2/2011 | Revets et al. |
| 2011/0053865 A1 | 3/2011 | Saunders et al. |
| 2011/0142831 A1 | 6/2011 | Cua et al. |
| 2011/0250213 A1 | 10/2011 | Tso et al. |
| 2012/0201746 A1 | 8/2012 | Liu et al. |
| 2012/0316324 A1 | 12/2012 | Adams et al. |
| 2014/0065142 A1 | 3/2014 | Roschke et al. |
| 2014/0154256 A1 | 6/2014 | Wu et al. |
| 2014/0302038 A1 | 10/2014 | Dimasi et al. |
| 2015/0079088 A1 | 3/2015 | Lowman et al. |
| 2016/0046730 A1 | 2/2016 | Ghayur et al. |
| 2016/0251440 A1 | 9/2016 | Roobrouck et al. |
| 2017/0106051 A1 | 4/2017 | Oh et al. |
| 2017/0298149 A1 | 10/2017 | Baeuerle et al. |
| 2018/0362655 A1 | 12/2018 | Wang et al. |
| 2019/0315864 A1 | 10/2019 | Xu et al. |
| 2019/0382500 A1 | 12/2019 | Abujoub et al. |
| 2020/0071716 A1 | 3/2020 | Raab et al. |
| 2020/0087624 A1 | 3/2020 | Wood et al. |
| 2020/0148772 A1 | 5/2020 | Ting et al. |
| 2020/0157237 A1 | 5/2020 | Regev et al. |

FOREIGN PATENT DOCUMENTS

| CN | 111018985 A | 6/2019 |
| CN | 111040035 A | 4/2020 |
| WO | 2008/011081 A2 | 1/2008 |
| WO | 2009/068631 A1 | 6/2009 |
| WO | 2010/142551 A2 | 12/2010 |
| WO | 2013/006544 A1 | 1/2013 |
| WO | 2013/059299 A1 | 4/2013 |
| WO | 2015/142675 A2 | 9/2015 |
| WO | WO2015/142675 | * 9/2015 |
| WO | 2016/097313 A1 | 6/2016 |
| WO | 2017/198212 A1 | 11/2017 |
| WO | 2018/233624 A1 | 12/2018 |
| WO | 2019/129221 A1 | 7/2019 |
| WO | 2020/094834 A1 | 5/2020 |

(Continued)

OTHER PUBLICATIONS

Apantaku et al. (Breast cancer diagnosis and screening, American Family Physician 2000) (Year: 2000) (Year: 2000).*
Martin et al (Journal of the National Cancer Institute, vol. 92, No. 14: pp. 1126-1135, Jul. 19, 2000) (Year: 2000) (Year: 2000).*
Almagro & Fransson, Frontiers in Bioscience 2008; 13:1619-33 (Year: 2008) (Year: 2008).*
De Genst et al., Dev Comp Immunol 2006; 30:187-98 (Year: 2006) (Year: 2006).*
Yoshinaga et al., J. Biochem 2008; 143:593-601 (Year: 2008) (Year: 2008).*
APMIS, Jun. 11, 2001, vol. 109, No. 10, pp. 647-655, cited on IDS filed Jan. 23, 2023) (Year: 2001).*

(Continued)

*Primary Examiner* — Meera Natarajan
(74) *Attorney, Agent, or Firm* — Kilpatrick Townsend & Stockton LLP

(57) ABSTRACT

The present disclosure relates to biologically active molecules comprising a single domain antibody (sdAb) that specifically binds to the extracellular domain of human IL2Rg, compositions comprising such antibodies, and methods of use thereof.

22 Claims, No Drawings
Specification includes a Sequence Listing.

(56) References Cited

FOREIGN PATENT DOCUMENTS

| WO | 2020/094836 | A1 | 5/2020 |
|----|-------------|----|--------|
| WO | 2020/144164 | A1 | 7/2020 |
| WO | 2020/187711 | A1 | 9/2020 |

OTHER PUBLICATIONS

Fu et al., "Comparison of Camelus Bactrianus VHH Sequences from Conventional and Heavy Chain Antibodies", National Center for Biotechnology Information, Available Online At: https://www.ncbi.nlm.nih.gov/nucleotide/KF179376.1, GenBank: KF179376.1, Sep. 21, 2013, 1 page.
Lundin et al., "Production and Partial Characterization of Mouse Monoclonal Antibodies Recognizing Common Cytokine Receptor Gamma Chain (Gammac) of Human, Mouse and Primate Origin", APMIS Journal, vol. 109, No. 10, 2001, pp. 647-655.
PCT/US21/44602, International Search Report and Written Opinion dated Feb. 2, 2022, 13 pages.
Crepaldi et al. Up-regulation of IL-10R1 expression is required to render human neutrophils fully responsive to IL-10. The Journal of Immunology. Aug. 15, 2001;167(4):2312-22.
Delgoffe et al., "Interpreting mixed signals: the cell's cytokine conundrum," Current Opinion in Immunology, vol. 23(5), pp. 632-638, Retrieved from the internet, URL: https://www.ncbi.nlm.nih.gov/pmc/articles/PMC3190023/pdf/nihms315192.pdf, (Oct. 2011).
Donnelly et al.. The expanded family of class II cytokines that share the IL-10 receptor-2 (IL-10R2) chain. Journal of leukocyte biology. Aug. 2004;76(2):314-21.
Fu et al. Comparison of Camelus Bactrianus VHH Sequences From Conventional and Heavy Chain Antibodies. Genbank Entry (online) National Center for Biotechnology Information, Sep. 21, 2013. Retried from the Internet www.ncbi.nlm.nih.gov/nucleotide/KF179376. 1, 1 page.
Jiang et al. Regulation of interleukin-10 receptor ubiquitination and stability by beta-TrCP-containing ubiquitin E3 ligase. PloS one. Nov. 8, 2011;6(11):e27464.
Lundin, et al. "Production and partial characterization of mouse monoclonal antibodies recognizing common cytokine receptor gamma chain (yc) of human, mouse and primate origin Note." Apmis 109, No. 10 (2001): 647-655.
Pingwara et al. IFN-λ Modulates the Migratory Capacity of Canine Mammary Tumor Cells via Regulation of the Expression of Matrix Metalloproteinases and Their Inhibitors. Cells. Apr. 23, 2021;10(5):999.

* cited by examiner

IL2RG BINDING MOLECULES AND METHODS OF USE

CROSS-REFERENCES TO RELATED APPLICATIONS

This application is a national stage application under 35 U.S.C. 371 of PCT/US2021/044602, filed Aug. 5, 2021, which claims priority to U.S. Provisional Application No. 63/061,562, filed Aug. 5, 2020, U.S. Provisional Application No. 63/078,745, filed Sep. 15, 2020, U.S. Provisional Application No. 63/135,884, filed Jan. 11, 2021, U.S. Provisional Application No. 63/136,098, filed Jan. 11, 2021, and U.S. Provisional Application No. 63/136,095, filed Jan. 11, 2021, the disclosures of which are hereby incorporated by reference in their entirety for all purposes.

SEQUENCE LISTING

The instant application contains a Sequence Listing which has been submitted electronically in ASCII format and is hereby incorporated by reference in its entirety. Said ASCII copy, created on Jan. 19, 2023, is named 106249-1361727-004720US_SL.txt and is 115,783 bytes in size.

FIELD OF THE INVENTION

The present disclosure relates to biologically active molecules comprising a single domain antibody that specifically binds to the extracellular domain of the IL2Rg, compositions comprising such single domain antibodies, and methods of use thereof.

BACKGROUND

IL2 is a pluripotent cytokine which is produced by antigen activated T cells. IL2 exerts a wide spectrum of effects on the immune system and plays important roles in regulating both immune activation, suppression and homeostasis. IL2 promotes the proliferation and expansion of activated T lymphocytes, induces proliferation and activation of naïve T cells, potentiates B cell growth, and promotes the proliferation and expansion of NK cells. Human interleukin 2 (IL2) is a 4 alpha-helix bundle cytokine of 133 amino acids. IL2 is a member of the IL2 family of cytokines which includes IL2, IL-4, IL-7, IL 9, IL-15 and IL21.

IL2 exerts its effect on mammalian immune cells through interaction with three different cell surface proteins: (1) CD25 (also referred to as the IL2 receptor alpha, IL2Rα, p55), CD122 (also referred to as the interleukin-2 receptor beta, IL2Rβ, IL15Rβ and p70-75), and CD132 (also referred to as the interleukin 2 receptor gamma, IL2Rγ; or common gamma chain as it is a component of other multimeric receptors in the IL2 receptor family). In addition to the "low affinity" CD25 IL2 receptor, two additional IL2 receptor complexes have been characterized: (a) an "intermediate affinity" dimeric IL2 receptor comprising CD122 and CD132 (also referred to as "IL2Rβγ"), and (b) a "high affinity" trimeric IL2 receptor complex comprising the CD25, CD122 and CD132 proteins (also referred to as "IL2Rαβγ"). hIL2 possesses a Kd of approximately $10^{-9}$ M with respect to the intermediate affinity CD122/CD132 (IL2βγ) receptor complex. hIL2 possesses a Kd of approximately $10^{-11}$ M with respect to the high IL2 affinity receptor complex. In addition to forming a subunit of the high affinity IL2 receptor, CD132 is a type 1 cytokine receptor and is shared by the receptor complexes for IL-4, IL-7, IL-9, IL-15, and IL21, hence it being referred to in the literature as the "common" gamma chain.

Human CD132 (hCD132) is expressed as a 369 amino acid pre-protein comprising a 22 amino acid N-terminal signal sequence. Amino acids 23-262 (amino acids 1-240 of the mature protein) correspond to the extracellular domain, amino acids 263-283 (amino acids 241-262 of the mature protein) correspond to the 21 amino acid transmembrane domain, and amino acids 284-369 (amino acids 262-347 of the mature protein) correspond to the intracellular domain. hCD132 is referenced at UniProtKB database as entry P31785. Human CD132 nucleic acid and protein sequences may be found as Genbank accession numbers: NM_000206 and NP_000197 respectively. Murine CD132 (mCD132) is expressed as a 369 amino acid pre-protein comprising a 22 amino acid N-terminal signal sequence. Amino acids 23-263 (amino acids 1-241 of the mature protein) correspond to the extracellular domain, amino acids 264-284 (amino acids 242-263 of the mature protein) correspond to the 21 amino acid transmembrane domain, and amino acids 285-369 (amino acids 263-347 of the mature protein) correspond to the intracellular domain. mCD132 is referenced at UniProtKB database as entry P34902.

Although monoclonal antibodies are the most widely used reagents for the detection and quantification of proteins, monoclonal antibodies are large molecules of about 150 kDa which may interferein their use in assays with several reagents competing for close epitopes recognition. A unique class of immunoglobulin containing a heavy chain domain and lacking a light chain domain (commonly referred to as heavy chain" antibodies (HCAbs) is present in camelids, including dromedary camels, Bactrian camels, wild Bactrian camels, llamas, alpacas, vicunas, and guanacos as well as cartilaginous fishes such as sharks. The isolated variable domain region of HCAbs is known as a VHH (an abbreviation for "variable-heavy-heavy" reflecting their architecture) or Nanobody® (Ablynx). Single domain VHH antibodies possesses the advantage of small size (~12-14 kD), approximately one-tenth the molecular weight a conventional mammalian IgG class antibody) which facilitates the binding of these VHH molecules to antigenic determinants of the target which may be inaccessible to a conventional monoclonal IgG format (Ingram et al., 2018). Furthermore, VHH single domain antibodies are frequently characterized by high thermal stability facilitating pharmaceutical distribution to geographic areas where maintenance of the cold chain is difficult or impossible. These properties, particularly in combination with simple phage display discovery methods that do not require heavy/light chain pairing (as is the case with IgG antibodies) and simple manufacture (e.g., in bacterial expression systems) make VHH single domain antibodies useful in a variety of applications including the development of imaging and therapeutic agents.

SUMMARY OF THE INVENTION

The present disclosure provides molecules that specifically bind to the extracellular domain of IL2Rg ("IL2Rg binding molecules").

The present disclosure provides IL2Rg binding molecules that specifically bind to the extracellular domain of IL2Rg (e.g., mouse or human IL2Rg).

In some embodiments, an IL2Rg binding molecule comprises a single domain antibody (sdAb) that specifically binds to the extracellular domain of the human IL2Rg.

In some embodiments, an IL2Rg binding molecule is a sdAb, the sdAb comprising a set of CDRs corresponding to CDR1, CDR2, and CDR3 as shown in a row of Table 1 below.

In some embodiments, the IL2Rg binding molecule comprises a CDR1, a CDR2, and a CDR3 as described in a row of Table 1 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 below.

In some embodiments, the IL2Rg binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 100% identity to a polypeptide sequence of any one of SEQ ID NOS: 1, 5, 9, 13, 17, 21, 25, 29, 33, 37, 41, 45, 49, 53, 57, 61, 65, 69, 73, 77, 81, 85, or 89, as shown in Table 1, below.

TABLE 1 hIL2Rg VHHs and CDRs

| Name | VHH Sequence (CDRs are underlined) | CDR1 | CDR2 | CDR3 |
|---|---|---|---|---|
| hIL2Rg_VHH-1 | QVQLQESGGGSVQAGGSLRLSCAASG FTFDDSDMGWYRQAPGNECDLVSTIS SDGSTYYADSVKGRFTISQDNAKNTV YLQMDSVKPEDTAVYYCAADFMIAIQ APGAGCWGQGTQVTVSS (SEQ ID NO: 1) | FTFDDSDMG (SEQ ID NO: 2) | TISSDGSTYYADSVKG (SEQ ID NO: 3) | DFMIAIQAPGAGC (SEQ ID NO: 4) |
| hIL2Rg_VHH-2 | QVQLQESGGGSVPAGGSLKLSCAASG FSFSSYPMTWARQAPGKGLEWVSTIA SDGGSTAYAASVEGRFTISRDNAKST LYLQLNSLKTESTAMYYCTKGYGDGT PAPGQGTQVTVSS (SEQ ID NO: 5) | FSFSSYPMT (SEQ ID NO: 6) | TIASDGGSTAYAASVE G (SEQ ID NO: 7) | GYGDGTPA (SEQ ID NO: 8) |
| hIL2Rg_VHH-3 | QVQLQESGGGSVQTGGSLRLSCTASG FTFDDREMNWYRQAPGNECELVSTIS SDGSTYYADSVKGRFTISQDNAKNTV YLQMDSVKPEDTAVYYCAADFMIAIQ APGAGCWGQGTQVTVSS (SEQ ID NO: 9) | FTFDDREMN (SEQ ID NO: 10) | TISSDGSTYYADSVKG (SEQ ID NO: 11) | DFMIAIQAPGAGC (SEQ ID NO: 12) |
| hIL2Rg_VHH-4 | QVQLQESGGGSVQAGGSLRLSCTASG FTFDDSDMGWYRQAPGNECELVSTIS SDGNTYYTDSVKGRFTISQDNAKNTV YLQMNSLGPEDTAVYYCAAEPRGYYS NYGGRRECNYWGQGTQVTVSS (SEQ ID NO: 13) | FTFDDSDMG (SEQ ID NO: 14) | TISSDGNTYYTDSVKG (SEQ ID NO: 15) | EPRGYYSNYGGRREC NY (SEQ ID NO: 16) |
| hIL2Rg_VHH-5 | QVQLQESGGGSVQAGGSLRLSCAASG FSFSSYPMTWARQAPGKGLEWVSTIA SDGGSTAYAASVEGRFRISRDNAKST LYLQLNSLKTEDTAMYYCTKGYGDGT PAPGQGTQVTVSS (SEQ ID NO: 17) | FSFSSYPMT (SEQ ID NO: 18) | TIASDGGSTAYAASVE G (SEQ ID NO: 19) | GYGDGTPA (SEQ ID NO: 20) |
| hIL2Rg_VHH-6 | QVQLQESGGGAVQAGGSLRLSCAASG FTFSNAHMSWVRQAPGKGREWISSIY SGGSTWYADSVKGRFTISRDNSKNTL YLQLNSLKTEDTAMYYCAENRLHYYS DDDSLRGQGTQVTVSS (SEQ ID NO: 21) | FTFSNAHMS (SEQ ID NO: 22) | SIYSGGSTWYADSVKG (SEQ ID NO: 23) | NRLHYYSDDDSL (SEQ ID NO: 24) |
| hIL2Rg_VHH-7 | QVQLQESGGGLVQPGGSLRLSCAASG FTFDDREMNWYRQAPGNECELVSTIS SDGSTYYADSVKGRFTISQDNAKNTV YLQMDSVKPEDTAVYYCAADFMIAIQ APGAGCWGQGTQVTVSS (SEQ ID NO: 25) | FTFDDREMN (SEQ ID NO: 26) | TISSDGSTYYADSVKG (SEQ ID NO: 27) | DFMIAIQAPGAGC (SEQ ID NO: 28) |
| hIL2Rg_VHH-8 | QVQLQESGGGSVQAGGSLRLSCVASG YTFSSYCMGWFRQAPGKEREGVAALG GGSTYYADSVKGRFTISQDNAKNTLY LQMNSLKPEDTAMYYCAAAWVACLEF GGSWYDLARYKHWGQGTQVTVSS (SEQ ID NO: 29) | YTFSSYCMG (SEQ ID NO: 30) | ALGGGSTYYADSVKG (SEQ ID NO 31) | AVWACLEFGGSWYDL ARYKH (SEQ ID NO 32) |

TABLE 1-continued hIL2Rg VHHs and CDRs

| Name | VHH Sequence (CDRs are underlined) | CDR1 | CDR2 | CDR3 |
|---|---|---|---|---|
| hIL2Rg_VHH-9 | QVQLQESGGGSVQAGGSLRLSCTASG FTFDDSDMGWYRQAPGGECELVTISS DGSTYYADSVKGRFTISQDNAKNTVY LQMNSLKPEDTAVYYCAAEPRGYYSN YGGRRECNYWGQGTQVTVSS (SEQ ID NO 33) | FTFDDSDMG (SEQ ID NO 34) | TISSDGSTYYADSVKG (SEQ ID NO 35) | EPRGYYSNYGGRREC NY (SEQ ID NO 36) |
| hIL2Rg_VHH-10 | QVQLQESGGGSVQAGGSLRLSCAASG SIYSSAYIGWFRQAPGKKREGVAGIY TRDGSTAYADSVKGRFTISQDSAKKT VYLQMNSLKPEDTAMYYCAAGRRTKS YVYIFRPEEYNYWGQGTQVTVSS (SEQ ID NO 37) | SIYSSAYIG (SEQ ID NO 38) | GIYTRDGSTAYADSVK G (SEQ ID NO 39) | GRRTKSYVYIFRPEE YNY (SEQ ID NO 40) |
| hIL2Rg_VHH-11 | QVQLQESGGGSVQAGGSLRLSCAASG FTFSSAHMSWVRQAPGKGREWIASIY SGGGTFYADSVKGRFTISRDNAKNTL YLQLNSLKTEDTAMYYCATNRLHYYS DDDSLRGQGTQVTVSS (SEQ ID NO 41) | FTFSSAHMS (SEQ ID NO 42) | SIYSGGGTFYADSVKG (SEQ ID NO 43) | NRLHYYSDDDSL (SEQ ID NO 44) |
| hIL2Rg_VHH-12 | QVQLQESGGGSVQAGGSLRLSCAASG FTFSNAHMSWVRQAPGKGREWISSIY SGGSTWYADSVKGRFTISRDNSKNTL YLQLNSLKTEDTAMYYCAENRLHYYS DDDSLRGQGTQVTVSS (SEQ ID NO 45) | FTFSNAHMS (SEQ ID NO 46) | SIYSGGSTWYADSVKG (SEQ ID NO 47) | NRLHYYSDDDSL (SEQ ID NO 48) |
| hIL2Rg_VHH-13 | QVQLQESGGGSVQAGGSLRLSCTASR FIFDDSDMGWYRQAPGNECELVTIS SDGSTYYADSVKGRFTISRDNAKNTV YLQMNSLKPEDTAVYYCAAEPRGYYS NYGGRRECNYWGQGTQVTVSS (SEQ ID NO 49) | FIFDDSDMG (SEQ ID NO 50) | TISSDGSTYYADSVKG (SEQ ID NO 51) | EPRGYYSNYGGRREC NY (SEQ ID NO 52) |
| hIL2Rg_VHH-14 | QVQLQESGGGSVQAGGSLKLSCTVSG FTADDSDMGWYRQGPGNECELVTISS DGSTYYADSVKGRFTISQDNAKNTVY LQMNSLKPEDTACYYCAAEPRGYYSN YGGRRECNYWGQGTQVTVSS (SEQ ID NO 53) | FTADDSDMG (SEQ ID NO 54) | TISSDGSTYYADSVKG (SEQ ID NO 55) | EPRGYYSNYGGRREC NY (SEQ ID NO 56) |
| hIL2Rg_VHH-15 | QVQLQESGGGLVQPGGSLRLSCAASG FTFSSAHMSWVRQAPGKGREWIASIY SGGGTFYADSVKGRFTISRDNAKNTL YLQLNSLKAEDTAMYYCATNRLHYYS DDDSLRGQGTQVTVSS (SEQ ID NO 57) | FTFSSAHMS (SEQ ID NO 58) | SIYSGGGTFYADSVKG (SEQ ID NO 59) | NRLHYYSDDDSL (SEQ ID NO 60) |
| hIL2Rg_VHH-16 | QVQLQESGGGLVQPGGSLRLSCVASG FTFSNAHMSWVRQAPGKGREWISSIY SGGSTWYADSVKGRFTISRDNSKNTL YLQLNSLKTEDTAMYYCAENRLHYYS DDDSLRGQGTQVTVSS (SEQ ID NO 61) | FTFSNAHMS (SEQ ID NO 62) | SIYSGGSTWYADSVKG (SEQ ID NO 63) | NRLHYYSDDDSL (SEQ ID NO 64) |
| hIL2Rg_VHH-17 | QVQLQESGGGLVQPGGSLRLSCAASG FTFSNAHMSWVRQAPGKGREWISSIY SGGSTWYADSVKGRFTISRDNSKNTL YLQLNSLKTEDTAMYYCAENRLHYYS DDDSLRGQGTQVTVSS (SEQ ID NO 65) | FTFSNAHMS (SEQ ID NO 66) | SIYSGGSTWYADSVKG (SEQ ID NO 67) | NRLHYYSDDDSL (SEQ ID NO 68) |
| hIL2Rg_VHH-18 | QVQLQESGGGLVQPGGSLRLSCAASG FTFSSYPMTWARQAPGKGLEWVSTIA SDGGSTAYAASVEGRFTISRDNAKST LYLQLNSLKTEDTAMYYCTKGYGDGT PAPGQGTQVTVSS (SEQ ID NO 69) | FTFSSYPMT (SEQ ID NO 70) | TIASDGGSTAYAASVE G (SEQ ID NO 71) | GYGDGTPA (SEQ ID NO 72) |

TABLE 1-continued hIL2Rg VHHs and CDRs

| Name | VHH Sequence (CDRs are underlined) | CDR1 | CDR2 | CDR3 |
|---|---|---|---|---|
| hIL2Rg_VHH-19 | QVQLQESGGGSVQAGGSLRLSCTASG FTFDDREMNWYRQAPGNECELVSTIS SDGSTYYADSVKGRFTISQDNAKNTV YLQMDSVKPEDTAVYYCAADFMIAIQ APGAGCWGQGTQVTVSS (SEQ ID NO 73) | FTFDDREMN (SEQ ID NO 74) | TISSDGSTYYADSVKG (SEQ ID NO 75) | DFMIAIQAPGAGC (SEQ ID NO 76) |
| hIL2Rg_VHH-20 | QVQLQESGGGSVQAGGSLRLSCTASG FTFDDSDMGWYRQAPGNECELVSTIS SDGSTYYADSVKGRFTISQDNAKNTV YLQMNSLKPEDTAVYYCAAEPRGYYS NYGGRRECNYWGQGTQVTVSS (SEQ ID NO 77) | FTFDDSDMG (SEQ ID NO 78) | TISSDGSTYYADSVKG (SEQ ID NO 79) | EPRGYYSNYGGRREC NY (SEQ ID NO 80) |
| hIL2Rg_VHH-21 | QVQLQESGGGSVQAGGSLRLSCVASG YTSCMGWFRQAPGKEREAVATIYTRG RSIYYADSVKGRFTISQDNAKNTLYL QMNSLKPEDIAMYSCAAGGYSWSAGC EFNYWGQGTQVTVSS (SEQ ID NO 81) | YTSCMG (SEQ ID NO 82) | TIYTRGRSIYYADSVK G (SEQ ID NO 83) | GGYSWSAGCEFNY (SEQ ID NO 84) |
| hIL2Rg_VHH-22 | QVQLQESGGGLVQPGGSLRLSCTASG FSFSSYPMTWARQAPGKGLEWVSTIA SDGGSTAYAASVEGRFTISRDNAKST LYLQLNSLKTEDTAMYYCTKGYGDGT PAPGQGTQVTVSS (SEQ ID NO 85) | FTFSSYPMT (SEQ ID NO 86) | TIASDGGSTAYAASVE G (SEQ ID NO 87) | GYGDGTPA (SEQ ID NO 88) |
| hIL2Rg_VHH-23 | QVQLQESGGGLVQPGGSLRLSCAASG FSFSSYPMTWARQAPGKGLEWVSTIA SDGGSTAYAASVEGRFTISRDNAKST LYLQLNSLKTEDTAMYYCTKGYGDGT PAPGQGTQVTVSS (SEQ ID NO 89) | FSFSSYPMT (SEQ ID NO 90) | TIASDGGSTAYAASVE G (SEQ ID NO 91) | GYGDGTPA (SEQ ID NO 92) |

In some embodiments, the foregoing sets of CDRs are incorporated in a humanized VHH framework to provide "humanized" sdAb IL2Rg binding molecules.

The disclosure further provides methods of chemical or recombinant processes for the preparation of the IL2Rg binding molecules of the present disclosure.

The disclosure further provides nucleic acids encoding the IL2Rg binding molecules. Table 2 below provide examples of DNA sequences encoding IL2Rg binding molecules as described herein.

TABLE 2

Nucleic Acid Sequences Encoding IL2RghIL2Rg Binding Molecules

| Name | DNA Sequence |
|---|---|
| hIL2Rg_VHH-1 | CAGGTCCAGCTCCAGGAGAGCGGGGGCGGTTCTGTGCAAGCCGGAGGCTCATTGAG ACTCTCATGCGCTGCAAGTGGTTTTACCTTCGATGACAGCGATATGGGATGGTATCG TCAGGCTCCGGGCAATGAGTGTGATCTGGTCTCCACTATCTCCTCTGATGGTTCCACA TACTATGCTGACTCTGTCAAGGGGCGCTTTACCATCTCCCAAGATAATGCCAAGAAC ACCGTGTACCTTCAGATGGATTCAGTTAAGCCCGAGGACACAGCCGTCTATTACTGC GCTGCGGATTTTATGATTGCCATCCAAGCTCCCGGAGCGGGATGCTGGGGCCAGGGA ACCCAGGTCACTGTGAGCAGT (SEQ ID NO 93) |
| hIL2Rg_VHH-2 | CAGGTGCAGTTGCAGGAGTCCGGCGGGGGTTCTGTGCCAGCGGGTGGGAGCCTCAA GCTCTCCTGTGCCGCTTCCGGCTTCTCATTCTCCTCTTACCCTATGACCTGGGCACGC CAAGCGCCCGGCAAGGGACTGGAATGGGTGTCCACCATTGCTTCCGATGGCGGTAG TACAGCCTACGCCGCGTCAGTGGAGGGTCGGTTCACGATCAGCCGGGACAACGCGA AGAGCACACTCTACCTCCAGCTGAACTCTCTGAAGACCGAGGACACCGCCATGTACT ATTGCACAAAGGGCTACGGCGACGGCACCCCGGCACCCGGCCAGGGCACCCAGGTG ACAGTCTCTTCC (SEQ ID NO 94) |

TABLE 2-continued

Nucleic Acid Sequences Encoding IL2RghIL2Rg Binding Molecules

| Name | DNA Sequence |
|---|---|
| hIL2Rg_VHH-3 | CAGGTGCAGTTGCAGGAAAGTGGTGGAGGGAGTGTGCAGACTGGGGGCTCTCTCCG<br>CCTCAGCTGCACAGCCTCTGGATTTACCTTCGATGATCGCGAGATGAACTGGTATCG<br>CCAGGCTCCGGGAAACGAGTGCGAACTGGTGTCTACAATCAGTTCTGACGGGTCCAC<br>CTATTACGCTGATAGTGTCAAGGGCCGCTTCACTATCTCTCAGGACAACGCGAAGAA<br>CACCGTTTACTTGCAGATGGATAGCGTGAAGCCTGAAGATACAGCGGTGTATTACTG<br>CGCTGCCGACTTTATGATTGCCATCCAGGCACCGGGGGCGGGGTGTTGGGGACAGG<br>GAACTCAGGTGACTGTGTCCTCC (SEQ ID NO 95) |
| hIL2Rg_VHH-4 | CAGGTTCAACTCCAAGAGAGTGGTGGCGGAAGCGTGCAGGCGGGCGGTTCTCTGCG<br>TCTGAGTTGCACTGCCAGCGGGATTTACCTTCGACGATTCCGACATGGGATGGTACAG<br>ACAGGCCCCTGGTAACGAGTGCGAACTCGTGAGTACTATCAGCTCCGACGGCAACA<br>CCTATTACACCGATTCTGTGAAGGGCAGGTTCACCATCTCCCAGGACAACGCTAAGA<br>ACACTGTGTACCTGCAAATGAATAGCCTGGGACCCGAGGACACAGCGGTCTATTACT<br>GCGCGGCAGAGCCGCGCGGCTATTACAGCAACTACGGCGGTAGACGCGAGTGCAAC<br>TACTGGGGGCAGGGGACGCAAGTGACTGTCTCCTCC (SEQ ID NO 96) |
| hIL2Rg_VHH-5 | CAAGTGCAGCTTCAGGAGTCCGGGGGTGGCAGCGTCCAGGCTGGGGGCAGCTTGCG<br>CCTGTCTTGCGCTGCGTCTGGGTTCAGCTTTAGCTCCTACCCTATGACCTGGGCTAGA<br>CAGGCCCCCGGCAAGGGGCTGGAGTGGGTGAGTACAATCGCCTCCGACGGAGGTAG<br>TACGGCCTACGCAGCGTCCGTCGAGGGTCGCTTCACCATCAGCCGGGATAACGCTAA<br>GTCCACCCTGTACCTTCAGCTCAATTCTCTCAAAACGGAGGATACCGCCATGTACTA<br>TTGCACCAAGGGATATGGCGACGGCACCCCAGCTCCTGGACAGGGCACACAGGTCA<br>CCGTTAGCTCC (SEQ ID NO 97) |
| hIL2Rg_VHH-6 | CAGGTCCAGCTTCAGGAGTCTGGCGGGGGCGCAGTACAGGCAGGGGTTCTCTGCG<br>TCTGTCCTGCGCCGCGTCCGGCTTTACTTTCAGCAACGCACACATGAGTTGGGTGCG<br>CCAAGCGCCCGGCAAGGGCCGGGAATGGATCAGTAGCATCTACAGTGGAGGCAGCA<br>CATGGTACGCCGACTCTGTTAAGGGTCGTTTTACGATCTCTCGTGACAACTCCAAGA<br>ACACTTTGTACCTCCAGCTCAATTCTCTCAAGACCGAGGACACCGCGATGTACTATT<br>GTGCCGAGAACAGGCTGCACTACTATTCCGACGATGACTCTCTCAGGGGCCAGGGA<br>ACTCAAGTTACCGTGTCCAGC (SEQ ID NO 98) |
| hIL2Rg_VHH-7 | CAAGTGCAGCTCCAAGAGAGTGGTGGCGGGCTGGTTCAGCCAGGGGGCAGCTTGAG<br>ACTCTCCTGCGCAGCTTCAGGCTTTACCTTCGATGACCGTGAGATGAACTGGTATCG<br>TCAGGCCCCAGGCAACGAGTGTGAGCTGGTTAGCACGATTTCTTCCGACGGTTCCAC<br>CTATTACGCCGACTCTGTGAAGGGACGTTTCACTATCTCCCAGGACAATGCCAAGAA<br>CACCGTGTACCTCCAGATGGACAGCGTGAAGCCGGAGGATACTGCTGTGTATTACTG<br>CGCTGCCGACTTTATGATCGCCATCCAGGCCCCTGGCGCGGGTTGCTGGGGCCAGGG<br>CACTCAGGTGACCGTGTCTTCC (SEQ ID NO 99) |
| hIL2Rg_VHH-8 | CAAGTGCAACTGCAAGAGTCCGGCGGTGGATCTGTGCAGGCCGGAGGCAGCCTGCG<br>GCTGAGCTGTGTAGCTTCCGGGTATACCTTTAGCTCATACTGTATGGGCTGGTTTCGT<br>CAGGCCCCCGGTAAGGAGCGCGAGGGCGTGGCCGCTCTTGGTGGAGGCTCCACCTA<br>TTACGCCGATTCCGTGAAGGGCAGGTTTACTATCTCCCAGGACAACGCGAAGAATAC<br>GCTCTATCTCCAGATGAATAGCCTGAAGCCCGAGGATACAGCTATGTATTACTGTGC<br>TGCCGCTTGGGTAGCCTGCCTGGAGTTCGGTGGCTCCTGGTACGATCTGGCACGGTA<br>CAAACATTGGGGGCAGGGCACCCAGGTCACCGTGTCTAGC (SEQ ID NO 100) |
| hIL2Rg_VHH-9 | CAGGTCCAGTTGCAGGAATCTGGGGGCGGTTCCGTACAAGCAGGTGGCTCCCTTCGG<br>TTGAGCTGTACCGCATCCGGCTTTACTTTCGACGATAGCGATATGGGCTGGTATCGT<br>CAGGCCCCAGGGGGCGAGTGCGAGCTGGTTACAATCTCCTCTGACGGCAGTACCTAT<br>TACGCAGACTCCGTCAAGGGCAGGTTCACTATCAGTCAGGACAATGCAAAGAACAC<br>TGTGTATCTCCAGATGAACTCTCTGAAGCCAGAAGATACTGCCGTGTATTACTGCGC<br>TGCCGGAACCGAGAGGCTATTACTCTAATTATGGCGGGCGTCGGGAGTGTAATTATTG<br>GGGACAGGGAACCCAGGTGACCGTGTCCTCC (SEQ ID NO 101) |
| hIL2Rg_VHH-10 | CAGGTGCAGCTCCAGGAGAGTGGCGGAGGCTCCGTGCAGGCTGGGGGCTCTCTGCG<br>TCTGAGCTGTGCCGCAAGCGGTAGCATTTACAGCTCTGCCTACATCGGGTGGTTTCG<br>TCAAGCGCCGGGCAAAAAGCGCGAAGGCGTGGCCGGAATCTACACGCGCGATGGCT<br>CCACCGCTTATGCTGACAGCGTTAAGGGACGTTTTACGATCAGCCAGGACTCTGCCA<br>AAAAGACTGTGTATCTCCAGATGAACTCCCTGAAACCTGAGGACACAGCCATGTATT<br>ACTGCGCCGCTGGCCGCCGTACAAAGAGCTATGTTTACATCTTTCGCCCCGAAGAGT<br>ACAACTACTGGGGCCAGGGAACCCAAGTGACTGTGTCCAGT (SEQ ID NO 102) |
| hIL2Rg_VHH-11 | CAGGTTCAGTTGCAGGAGTCCGGCGGAGGCAGCGTGCAGGCCGGAGGCTCCTTGCG<br>CTTGTCCTGTGCGGCTTCTGGCTTCACCTTCTCATCTGCTCACATGAGTTGGGTGCGT<br>CAGGCCCCAGGGAAAGGTCGCGAGTGGATTGCCTCCATCTACAGCGGTGGGGGCAC<br>TTTTTATGCGGACAGCGTGAAGGGCCGCTTTACCATCAGCCGTGACAACGCTAAGAA<br>CACCCTGTATCTCCAACTCAATTCCCTCAAGACCGAGGATACAGCGATGTACTATTG<br>TGCAACCAACCGCCTTCACTATTACTCCGACGATGACAGCCTGCGCGGACAGGGGAC<br>CCAGGTGACGGTGTCCAGC (SEQ ID NO 103) |
| hIL2Rg_VHH-12 | CAGGTGCAACTCCAGGAAAGTGGCGGAGGCTCAGTGCAGGCAGGTGGCTCTCTCCG<br>CCTTTCCTGCGCTGCCAGCGGATTCACCTTCTCTAACGCTCACATGAGCTGGGTTCGT<br>CAGGCTCCCGGCAAAGGCCGTGAATGGATTAGCTCCATCTATAGTGGCGGAAGTACT |

TABLE 2-continued

Nucleic Acid Sequences Encoding IL2RghIL2Rg Binding Molecules

| Name | DNA Sequence |
|---|---|
| | TGGTACGCAGATAGCGTCAAGGGCCGCTTCACTATTAGTCGGGATAACTCCAAGAAC<br>ACTCTGTACCTCCAGCTGAACTCATTGAAAACCGAGGACACGGCTATGTACTATTGT<br>GCTGAGAACAGGCTGCACTATTACTCCGACGATGACTCTCTGAGGGGTCAGGGCACC<br>CAGGTGACCGTCAGCTCC (SEQ ID NO 104) |
| hIL2Rg_VHH-13 | CAGGTCCAACTCCAGGAGTCCGGCGGAGGCAGCGTGCAGGCTGGAGGCTCTCTCCG<br>CCTGAGCTGCACAGCTTCCAGATTCATCTTCGATGACTCCGACATGGGCTGGTATCG<br>CCAGGCTCCAGGGAACGAGTGCGAACTGGTGAGCACCATCTCTTCAGACGGTAGCA<br>CCTATTACGCCGACAGTGTGAAGGGGCGCTTCACCATCTCCCGCGACAATGCTAAAA<br>ATACGGTGTATCTCCAGATGAACTCCCTCAAACCGGAGGACACAGCTGTATATTACT<br>GTGCTGCGGAACCACGGGGCTACTATAGCAACTATGGTGGAAGGCGCGAGTGCAAC<br>TACTGGGGTCAGGGCACACAGGTGACGGTTTCCTCC (SEQ ID NO 105) |
| hIL2Rg_VHH-14 | CAGGTGCAGCTCCAGGAGAGCGGCGGTGGCTCCGTGCAGGCTGGTGGCAGCCTGAA<br>GCTGTCCTGCACCGTGAGTGGCTTCACAGCCGACGATTCTGATATGGGCTGGTATCG<br>CCAAGGCCCCGGCAATGAGTGCGAGCTGGTAACCATTAGCTCAGACGGCTCTACAT<br>ACTATGCCGATTCTGTTAAGGGCCGCTTTACTATCTCACAGGATAATGCCAAGAACA<br>CAGTGTACTTGCAGATGAACTCTCTGAAACCGGAAGACACAGCTGTGTATTACTGTG<br>CTGCGGAGCCTAGAGGGTATTACAGCAATTACGGGGGCCGGAGAGAGTGTAACTAT<br>TGGGGGCAGGGCACCCAAGTGACCGTTTCCTCC (SEQ ID NO 106) |
| hIL2Rg_VHH-15 | CAGGTCCAGCTTCAGGAATCTGGGGGCGGTCTCGTGCAGCCCGGCGGGTCCCTGCGT<br>CTGTCTTGTGCTGCGAGCGGCTTCACGTTCTCAAGTGCCCACATGAGCTGGGTAAGG<br>CAGGCACCGGGCAAGGGGCGCGAGTGGATTGCAAGCATCTATTCAGGCGGGGGCAC<br>ATTCTACGCCGACAGCGTGAAGGGACGTTTTACAATCTCCAGAGATAACGCAAAGA<br>ACACTCTCTACCTCCAACTCAACTCCTTGAAGGCGGAAGATACTGCAATGTATTACT<br>GTGCTACTAACCGTCTTCATTATTACTCTGACGATGACTCCCTGCGGGGGCAGGGTA<br>CACAGGTGACAGTGAGTTCC (SEQ ID NO 107) |
| hIL2Rg_VHH-16 | CAGGTGCAGCTGCAAGAATCTGGTGGAGGGCTGGTCCAGCCTGGGGGCTCCCTGCG<br>CCTCTCATGTGTCGCATCTGGCTTCACCTTCAGCAACGCCCACATGAGCTGGGTTCGC<br>CAAGCCCCTGGGAAGGGCCGGGAGTGGATCTCCAGTATCTATTCCGCGGAAGCAC<br>TTGGTATGCAGACAGCGTCAAAGGACGGTTCACTATTTCTCGTGATAATTCTAAGAA<br>CACCCTGTACCTTCAGCTGAACAGCCTGAAGACCGAGGACACTGCTATGTACTATTG<br>TGCTGAGAATCGCCTGCATTACTATAGCGACGATGACAGTCTGCGCGGACAGGGGA<br>CCCAGGTCACCGTGTCCTCT (SEQ ID NO 108) |
| hIL2Rg_VHH-17 | CAGGTTCAGTTGCAGGAATCAGGAGGCGGTCTGGTGCAGCCTGGGGGCTCTCTGCGT<br>CTCTCCTGCGCCGCTTCCGGCTTCACATTCTCCAACGCCCACATGAGCTGGGTCCGCC<br>AGGCCCCTGGGAAGGGCCGCGAGTGGATCTCCAGTATCTACAGCGGGGGCTCCACT<br>TGGTACGCAGACAGCGTCAAAGGGAGGTTTACCATTAGCCGTGACAATTCTAAGAA<br>CACATTGTATTTGCAGCTGAACTCTCTTAAAACCGAGGACACCGCCATGTACTATTG<br>TGCTGAGAACAGGCTCCACTATTACTCAGACGATGACTCACTTCGCGGGCAGGGAAC<br>CCAGGTCACCGTCTCCTCT (SEQ ID NO 109) |
| hIL2Rg_VHH-18 | CAAGTCCAGCTCCAGGAAAGCGGCGGTGGCCTGGTGCAACCTGGCGGGTCTCTGCGG<br>CTTGTCATGCGCTGCCTCCGGCTTCACCTTCTCATCTTACCCTATGACCTGGGCGCGT<br>CAGGCTCCCGGCAAGGGATTGAGTGGGTGTCTACTATTGCCTCCGACGGTGGCAGC<br>ACGGCCTACGCAGCGTCTGTAGAAGGACGCTTCACAATTAGCAGAGACAACGCAAA<br>ATCTACTTTGTACCTTCAGCTCAACAGCCTGAAGACCGAAGACACAGCTATGTATTA<br>CTGCACAAAAGGCTACGGGGACGGCACGCCAGCGCCTGGACAGGGGACACAGGTG<br>ACCGTATCTTCT (SEQ ID NO 110) |
| hIL2Rg_VHH-19 | CAGGTGCAGTTGCAGGAATCAGGGGGTGGCTCTGTGCAGGCCGGGGGCTCCCTGCG<br>TCTGTCCTGTACTGCGAGCGGCTTCACCTTTGATGACCGCGAGATGAACTGGTATCG<br>CCAGGCTCCGGGGAACGAGTGCGAACTCGTGTCTACAATTAGCTCCGATGGTTCAAC<br>ATACTATGCTGATTCTGTCAAAGGTCGCTTTACCATCTCACAGGACAACGCCAAGAA<br>CACCGTCTACCTCCAGATGGACTCTGTGAAGCCTGAAGATACCGCCGTATACATTG<br>CGCCGCTGACTTTATGATTGCCATTCAGGCTCCGGGTGCTGGATGCTGGGGTCAGGG<br>GACTCAGGTGACCGTGTCTTCA (SEQ ID NO 111) |
| hIL2Rg_VHH-20 | CAAGTGCAGTTGCAGGAAAGCGGCGGTGGGTCCGTGCAAGCCGGAGGTTCTCTCCG<br>CCTGTCTTGCACTGCCTCAGGTTTTACCTTCGACATGATGGCTGGTACAGG<br>CAGGCTCCCGGCAATGAGTGCGAGCTGGTGTCTACGATCTCAAGTGATGGCTCCACC<br>TACTATGCCGATAGCGTAAAAGGAAGGTTTACTATTAGCAGGATAACGCGAAGAA<br>CACGGTGTACCTCCAGATGAACAGTCTCAAGCGGAGGATACTGCCGTGTATTACTG<br>TGCTGCCGAGCCGCGTGGCTATTACTCCAACTACGGTGGCAGACGTGAATGCAATTA<br>CTGGGGACAGGGTACTCAGGTTACCGTGTCCTCT (SEQ ID NO 112) |
| hIL2Rg_VHH-21 | CAGGTTCAACTTCAGGAATCCGGGGGCGGTTCCGTGCAAGCCGGGGGTAGCCTGCG<br>TCTGTCTTGCGTGGCCAGCGGCTATACCTCCTGTATGGGTTGGTTTCGGCAGGCTCCT<br>GGGAAGGAGCGCGAAGCCGTGGCGACCATCTACACACGGGGCCGCAGCATCTATTA<br>CGCTGACAGTGTGAAGGGCCGCTTCACCATCTCCCAGGATAACGCCAAGAATACCCT<br>GTATCTGCAAATGAACTCCCTGAAGCCTGAGGACATCGCCATGTATTCCTGCGCAGC<br>TGGAGGGTACTCATGGTCCGCTGGGTGCGAGTTTAATTATTGGGGCCAAGGAACCCA<br>GGTGACCGTCTCCTCA (SEQ ID NO 113) |

TABLE 2-continued

Nucleic Acid Sequences Encoding IL2RghIL2Rg Binding Molecules

| Name | DNA Sequence |
|---|---|
| hIL2Rg_VHH-22 | CAAGTGCAGCTCCAGGAGTCTGGCGGGGGCCTGGTTCAGCCTGGTGGGTCCCTGCGC<br>CTGTCTTGCACGGCTTCCGGCTTTAGCTTCTCCTCATATCCAATGACCTGGGCACGCC<br>AGGCTCCTGGTAAGGGCCTGGAGTGGGTCTCCACCATCGCCTCTGATGGTGGGTCAA<br>CTGCCTATGCTGCCTCCGTCGAGGGTAGATTCACAATCAGCAGAGACAACGCCAAAT<br>CCACGCTGTACCTGCAACTCAACTCCTTGAAGACCGAGGACACAGCTATGTATTACT<br>GTACCAAAGGCTACGGCGACGGCACTCCTGCTCCCGGACAGGGGACCCAGGTGACT<br>GTGTCTAGC (SEQ ID NO 114) |
| hIL2Rg_VHH-23 | CAGGTCCAACTTCAGGAAAGCGGGGGTGGACTGGTACAGCCAGGGGGCAGTCTGCG<br>CCTGTCCTGTGCCGCAAGCGGGTTTTCTTTCTCCAGTTACCCCATGACCTGGGCTCGC<br>CAAGCACCTGGAAAGGGACTGGAGTGGGTGTCTACTATTGCGTCAGATGGTGGGAG<br>TACGGCTTACGCCGCGAGCGTGGAGGGTCGTTTTACGATCAGTAGGGACAACGCCA<br>AAAGCACTCTGTACCTCCAGCTTAACAGCCTGAAGACCGAGGACACCGCCATGTATT<br>ACTGTACCAAGGGCTACGGAGACGGCACCCCTGCGCCGGGGCAAGGCACCCAGGTG<br>ACCGTAAGTTCA (SEQ ID NO 115) |

In some embodiments, the ILRg is the murine IL2Rg.

In some embodiments, an IL2Rg binding molecule comprises a single domain antibody (sdAb) that specifically binds to the extracellular domain of the mouse or murine IL2Rg (mIL2Rg).

In some embodiments, an IL2Rg binding molecule is a sdAb, the sdAb comprising a set of CDRs corresponding to CDR1, CDR2, and CDR3 as shown in a row of Table 3 below.

In some embodiments, the IL2Rg binding molecule comprises a CDR1, a CDR2, and a CDR3 as described in a row of Table 3 below, in which the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 3 below.

In some embodiments, the IL2Rg binding molecule consists of, optionally consists essentially of, or optionally comprises a single domain antibody (sdAb) having at least 80%, alternatively at least 85%, alternatively at least 90%, alternatively at least 95%, alternatively at least 98%, alternatively at least 99% identity (or being identical except for 1, 2, 3, or 4 amino acids that optionally are conserved substitutions) or 100% identity to a polypeptide sequence of any one of SEQ ID NOS: 116, 120, 124, 128, 132, 136, 140, 144, 148, 152, 156, 160, 164 168 or 172 as shown in Table 3 below.

TABLE 3 mIL2Rg VHHs and CDRs Amino Acid (AA) Sequences

| Name | VHH AA Sequence (CDRs underlined) | VHH SEQ ID | CDR1 AA Seq | CDR1 SEQ ID | CDR2 AA Seq | CDR2 SEQ ID | CDR3 AA Seq | CDR3 SEQ ID |
|---|---|---|---|---|---|---|---|---|
| mIL2Rg_VHH1 | QVQLQESGGGSVLAGGSLRLSCVASGYGYNYIGWFRQTPGKEREGVAVIYTGGGDTYYADSVKGRFTASRDNAKSTLYLQMNSLEPEDTAMYYGVARYCVGSVYACLRGGHDEYAHWGQGTQVTVSS | 116 | YGYNYIG | 117 | VIYTGGGDTYYADSVKG | 118 | SVYACLRGGHDEYAH | 119 |
| mIL2Rg_VHH2 | QVQLQESGGGSVQPGGGSLRLSCAASGSTYANYLMGWFRQAPGKEREGVAAIYSGGGSTYYADSVKGRFTISQDNAKNTLYLQMNSLKPEDTAMYYCAAASAVKGDKGDIVVVVTGTQRMEYDYWGHGTQVTVSS | 120 | STYANYLMG | 121 | AIYSGGGSTYYADSVKG | 122 | ASAVKGDKGDIVVVVTGTQRMEYDY | 123 |
| mIL2Rg_VHH3 | QVQLQESGGGSVQAGASLRLSCSVSGFTFDESVMSWLRQGPGNECDAVAIISSDDNTYYDDSVKGRFTISEDNAKNMVYLQMNSLKPEDTAVYYCAARRRRPVYDSDYELRPRPLCGDFGVWGQGTQVTVSS | 124 | FTFDESVMS | 125 | IISSDDNTYYDSVKG | 126 | RRRRPVYDSDYELRPRPLCGDFGV | 127 |
| mIL2Rg_VHH4 | QVQLQESGGGSVQAGGSLRLSCIGSGLPFDEDDMGWYRQAPGNECELVSSISSDGTAYYADSVKGRFTISRDNAKTVLLQMNSLKPEDTAVYYC | 128 | LPFDEDDMG | 129 | SISSDGTAYYADSVKG | 130 | GVHRQFGGSSSCGDAFYGMDY | 131 |

TABLE 3-continued mIL2Rg VHHs and CDRs Amino Acid (AA) Sequences

| Name | VHH AA Sequence (CDRs underlined) | VHH SEQ ID | CDR1 AA Seq | CDR1 SEQ ID | CDR2 AA Seq | CDR2 SEQ ID | CDR3 AA Seq | CDR3 SEQ ID |
|---|---|---|---|---|---|---|---|---|
| | AAGVHRQFGGSSSCGDAFY GMDYWGKGTQVTVSS | | | | | | | |
| mIL2Rg_VHH5 | QVQLQESGGGSVQAGGSLR LSCVASGDVYGRNSMAWFR QAPGKEREGVAVGYSVVTT TYYADSVKGRFTISEDNDK NTVYLEMNSLKPEDTAMYY CAADGNLWRGLRPSEYTYW GQGTQVTVSS | 132 | DVYGRNS MA | 133 | VGYSVVT TYYADSV KG | 134 | DGNLWRG LRPSEYT Y | 135 |
| mIL2Rg_VHH6 | QVQLQESGGGSVQAGGSLR LSCATSGFPYSRYCMGWFR QAPGKEREGVAAIEPDGST SYADSVKGRFTISQDNAVN TLYLQMNNLKPEDTAMYYC AADERCFYLKDYDLRRPAQ YRYWGQGTQVTVSS | 136 | FPYSRYC MG | 137 | AIEPDGS TSYADSV KG | 138 | DERCFYL KDYDLRR PAQYRY | 139 |
| mIL2Rg_VHH7 | QVQLQESGGGLVQPGGSLR LSCTVSGFTFDESDMGWLR QNPGNECGVVSVITSDDNP YYDDSVKGRFTISEDNAKN MVYLQMNSLKPEDTGVYYC ATRSRQPVYSRDYELRPRP LCGDFGVWGQGTQVTVSS | 140 | FTFDESD MG | 141 | VITSDDN PYYDDSV KG | 142 | RSRQPVY SRDYELR PRPLCGD FGV | 143 |
| mIL2Rg_VHH8 | QVQLQESGGGSVQAGGSLR LSCTASGFTFDDFDMGWYR QAPGNECELVSTISDDGST YYADSVKGRSSISRDNAKN TVYLQMNRLKPEDTGVYYC AAEGALGSKTNCGWVGNFG YWGQGTQVTVSS | 144 | FTFDDFD MG | 145 | TISDDGS TYYADSV KG | 146 | EGALGSK TNCGWVG NFGY | 147 |
| mIL2Rg_VHH9 | QVQLQESGGGSVQAGGSLR LSCAASGFTFDDFDMGWYR QAPGNECELVSTISDDGST YYADSVKGRSSISRDNAKN TVYLQMNSLKPEDTAVYYC AAEGALGSKTNCGWVGNFG YWGQGTQVTVSS | 148 | FTFDDFD MG | 149 | TISDDGS TYYADSV KG | 150 | EGALGSK TNCGWVG NFGY | 151 |
| mIL2Rg_VHH10 | QVQLQESGGGLVQPGGSLR LSCAASGFTFDDFDMGWYR QAPGNECELVSTISDDGST YYADSVKGRSSISRDNAKS TVYLQMNRLKPEDTGVYYC AAEGALGSKTNCGWVGNFG YWGQGTQVTVSS | 152 | FTFDDFD MG | 153 | TISDDGS TYYADSV KG | 154 | EGALGSK TNCGWVG NFGY | 155 |
| mIL2Rg_VHH11 | QVQLQESGGGLVQPGGSLK LSCAASGFTFSDRDMGWYR QAPGNECERVSTISDDGST YYADSVKGRSSISRDNAKN TVYLQMNSLKPEDTAVYYC AAEGALGSKTNCGWVGNFG YWGQGTQVTVSS | 156 | FTFSDRD MG | 157 | TISDDGS TYYADSV KG | 158 | EGALGSK TNCGWVG NFGY | 159 |
| mIL2Rg_VHH12 | QVQLQESGGGSVLAGGSLR LSCVASGYGYNYIGWFRQT PGKEREGVAVIYIGGGDTY YADSVKGRFTASRDNAKST LYLQMNSLEPEDTAMYYCV ARYCVGSVYACLRGGHDEY AHWGQGTQVTVSS | 160 | YGYNYIG | 161 | VIYIGGG DTYYADS VKG | 162 | RYCVGSV YACLRGG HDEYAH | 163 |
| mIL2Rg_VHH13 | QVQLQESGGGSVLAGGSLR LSCVASGYGYNYIGWVRQT PGKEREGVAVIYTGGGDTY YADSVKGRFTADRDNAKST LYLQMNSLEPEDTAMYYCV ARYCVGSVYACLRGGHDEY AHWGQGTQVTVSS | 164 | YGYNYIG | 165 | VIYTGGG DTYYADS VKG | 166 | RYCVGSV YACLRGG HDEYAH | 167 |

TABLE 3-continued mIL2Rg VHHs and CDRs Amino Acid (AA) Sequences

| Name | VHH AA Sequence (CDRs underlined) | VHH SEQ ID | CDR1 AA Seq | CDR1 SEQ ID | CDR2 AA Seq | CDR2 SEQ ID | CDR3 AA Seq | CDR3 SEQ ID |
|---|---|---|---|---|---|---|---|---|
| mIL2Rg_VHH14 | QVQLQESGGGSVQAGGSLR LSCAASGFTFDDFDMGWYR QAPGNECELVSTISDDGST YYANSVKGRSSISRDNAKN MVYLQMNSLKPEDTAVYYC AAEGALGSKTNCGWVGNFG YWGQGTQVTVSS | 168 | FTFDDFD MG | 169 | TISDDGS TYYANSV KG | 170 | EGALGSK TNCGWVG NFGY | 171 |
| mIL2Rg_VHH15 | QVQLQESGGGSVQAGGSLR LSCTASGFTFDDFDMGWYR QAPGNECELVSTISDDGST YYADSVKGRSSISRDNAKN TVYLQMNRLKPEDTGVYYC AAEGALGSKMNCGWVGNFG YWGQGTQVTVSS | 172 | FTFDDFD MG | 173 | TISDDGS TYYADSV KG | 174 | EGALGSK MNCGWVG NFGY | 175 |

The disclosure further provides nucleic acids encoding the IL2Rg binding molecules. Table 4 below provide examples of DNA sequences encoding mIL2Rg binding molecules as described in Table 3 above.

TABLE 4

DNA Sequences Encoding mIL2Rg VHHs

| Name | DNA Sequence | SEQ ID NO |
|---|---|---|
| mIL2Rg_VHH1 | CAGGTGCAACTCCAGGAGTCCGGCGGGGGCTCCGTGCTG GCTGGCGGATCTTTGAGGCTGTCTTGCGTGGCTTCTGGCT ATGGCTATAATTACATCGGCTGGTTCCGTCAGACACCCG GCAAGGAGCGCGAAGGGGTGGCGGTCATTTACACAGGG GGTGGGGACACTTATTACGCCGACTCCGTCAAGGGTAGG TTTACCGCTAGTCGCGATAATGCCAAAAGTACGCTGTAC CTGCAAATGAACAGCTTGGAGCCAGAGGACACCGCCAT GTATTACGGAGTGGCTCGCTACTGTGTGGGCAGTGTGTA CGCTTGCCTGCGCGGAGGCCACGACGAGTACGCACACTG GGGCCAGGGAACCCAGGTGACAGTGTCTAGC | 176 |
| mIL2Rg_VHH2 | CAGGTGCAGCTCCAGGAGTCTGGGGGTGGCAGCGTCCA GCCAGGTGGCTCATTGAGACTGTCTTGTGCTGCATCTGG CTCCACCTACGCTAATTACCTGATGGGATGGTTCAGGCA GGCCCCTGGTAAGGAGCGTGAGGGCGTGGCCGCTATCTA TTTCTGGCGGTGGGTCCACCTACTATGCTGACTCCGTCAA GGGACGCTTCACTATTTCTAAGACAATGCCAAGAACAC TTTGTACTTGCAAATGAACTCACTCAAACCTGAGGACAC CGCGATGTACTATTGCGCAGCGGCATCCGCAGTGAAGGG AGACAAAGGGGATATCGTGGTAGTTGTGACCGGCACCC AGCGTATGGAGTACGACTACTGGGGACATGGCACCCAG GTGACAGTTAGCTCC | 177 |
| mIL2Rg_VHH3 | CAGGTACAGTTGCAGGAGAGTGGTGGGGGTTCCGTCCAG GCCGGTGCCTCTCTTCGCCTCAGTTGTAGCGTGAGCGGTT TCACGTTCGACGAGTCAGTGATGTCCTGGTTGCGCCAGG GTCCCGGCAATGAGTGCGACGCGGTCGCTATTATCAGCT CCGATGACAACACCTATTACGACGATAGCGTGAAAGGCC GCTTTACCATCTCCGAGGACAACGCCAAAAACATGGTGT ATCTGCAAATGAACTCACTGAAGCCGGAAGACACCGCA GTGTACTATTGCGCCGCGCGTCGGCGCAGACCTGTGTAC GATTCCGATTATGAACTCCGGCCACGTCCGCTGTGTGGC GATTTCGGCGTGTGGGCCAGGGGACCCAGGTGACGGTC TCCTCC | 178 |
| mIL2Rg_VHH4 | CAGGTGCAGCTCCAGGAATCTGGCGGGGGCTCTGTGCAG GCTGGTGGCTCCCTTCGCCTGTCCTGTATTGGCTCCGGTC TTCCTTTCGACGAGGATGACATGGGCTGGATCGCCAGG CCCCTGGGAATGAGTGTGAATTGGTCAGCTCAATCTCCA GTGACGGCACCGCCTATTACGCCGATTCCGTCAAGGGAC GCTTCACTATCTCCAGAGACAACGCCAAGAACACTGTGC TGTTGCAGATGAACTCCCTGAAGCCCGAGGATACCGCTG TCTATTACTGCGCAGCCGGGGTCCACAGACAGTTCGGCG GTTCCAGTTCTGCGGCGACGCCTTCTACGGCATGGATT ACTGGGGCAAGGGAACTCAGGTCACAGTGTCTTCC | 179 |

TABLE 4-continued

DNA Sequences Encoding mIL2Rg VHHs

| Name | DNA Sequence | SEQ ID NO |
|---|---|---|
| mIL2Rg_VHH5 | CAGGTTCAGCTTCAGGAGTCCGGCGGGGGCTCCGTACAG<br>GCAGGGGGCTCACTGCGTCTTTCCTGTGTGGCGAGTGGC<br>GACGTGTATGGCCGTAACAGCATGGCTTGGTTCCGGCAG<br>GCACCTGGAAAGGAACGCGAGGGCGTTGCAGTTGGGTA<br>TTCCGTAGTGACAACCACTTACTATGCCGACAGTGTGAA<br>GGGCCGGTTTACGATCTCAGAGGACAACGATAAAAACA<br>CAGTGTACCTGGAGATGAACTCCCTGAAGCCGGAAGAC<br>ACTGCTATGTATTACTGCGCTGCCGATGGCAACCTGTGG<br>CGCGGACTCAGGCCCTCCGAGTACACTTATTGGGGTCAG<br>GGCACCCAGGTGACCGTTTCAAGT | 180 |
| mIL2Rg_VHH6 | CAGGTCCAGCTTCAGGAGTCAGGTGGCGGTAGTGTCCAG<br>GCAGGCGGTAGCCTGCGCCTTAGCTGTGCTACATCCGGC<br>TTCCCTTACTCACGCTATTGTATGGGCTGGTTCAGGCAAG<br>CTCCCGGTAAAGAGCGCGAGGGAGTGGCAGCCATCGAG<br>CCTGACGGGAGCACATCTTATGCTGACTCTGTAAAGGGG<br>CGTTTCACCATCTCTCAGGAACGCCGTTAATACACTG<br>TACTTGCAAATGAATAACCTGAAGCCCGAGGACACAGCT<br>ATGTATTACTGCGCAGCCGACGAGCGTTGCTTCTATTTG<br>AAGGACTATGACCTCAGAAGGCCAGCCCAGTACCGCTAC<br>TGGGGGCAGGGCACCCAGGTTACCGTGTCATCT | 181 |
| mIL2Rg_VHH7 | CAGGTGCAGTTGCAGGAGAGTGGCGGTGGCCTCGTGCA<br>GCCTGGCGGAAGCCTCCGTCTGAGCTGCACTGTGTCCGG<br>CTTCACTTTCGACGAGAGCGACATGGGCTGGCTGAGGCA<br>GAACCCTGGTAACGAGTGCGGCGTTGTGAGTGTCATCAC<br>GTCTGATGACAACCCATACTATGATGACAGCGTCAAGGG<br>CCGCTTTACTATCTCCGAGGATAACGCCAAGAACATGGT<br>GTACCTCCAGATGAACTCACTGAAGCCCGAGGATACCGG<br>CGTTTATTACTGTGCAACCAGGAGCCGTCAGCCTGTGTA<br>CTCACGCGATTACGAGCTGCGGCCCCGCCCCCTCTGTGG<br>AGACTTTGGTGTGTGGGGCCAGGGCACCCAGGTGACTGT<br>TTCCAGC | 182 |
| mIL2Rg_VHH8 | CAGGTGCAGTTGCAGGAGAGTGGAGGGGGCTCAGTGCA<br>GGCTGGCGGGTCCTTGCGTCTGTCTTGCACCGCCTCTGGC<br>TTCACCCTTCGATGACTTCGATATGGGTTGGTATCGCCAG<br>GCTCCAGGGAACGAGTGCGAATTGGTCAGCACTATCAGC<br>GACGATGGCTCAACATATTACGCCGACTCTGTGAAGGGA<br>CGGTCTAGCATTAGCCGGGACAACGCAAAGAACACCGT<br>CTATCTCCAGATGAACCGCTTGAAGCCTGAGGATACCGG<br>AGTCTATTACTGCGCCGCTGAGGGCGCGTTGGGCTCCAA<br>GACTAATTGTGGCTGGGTGGGCAACTTCGGATATTGGGG<br>CCAGGGAACACAGGTTACCGTTTCCAGC | 183 |
| mIL2Rg_VHH9 | CAGGTGCAGTTGCAGGAGTCTGGAGGCGGTTCCGTTCAG<br>GCCGGGGGCTCTCTGCGCCTGTCCTGCGCTGCCTCCGGG<br>TTTACATTTGACGATTTCGATATGGGCTGGTATCGCCAG<br>GCCCCTGGCAACGAGTGCGAACTGGTGTCTACTATCTCC<br>GATGACGGCTCAACCTACTATGCAGACTCCGTAAAGGGC<br>AGATCCAGCATCTCCCGCGACAATGCCAAAAACACTGTG<br>TACCTCCAGATGAACTCCCTCAAGCCTGAGGATACGGCG<br>GTGTACTATTGTGCTGCCGAGGGTGCGCTCGGTAGCAAG<br>ACTAATTGCGGCTGGGTGGGCAACTTCGGGTACTGGGGT<br>CAGGGGACCCAGGTAACCGTGTCTTCT | 184 |
| mIL2Rg_VHH10 | CAGGTGCAGTTGCAGGAAAGCGGTGGGGGCCTGGTGCA<br>GCCCGGAGGCAGCCTGCGCTTGAGCTGCGCTGCCTCTGG<br>CTTCACATTCGATGACTTCGATATGGGCTGGTATCGTCA<br>AGCACCCGGAAACGAGTGCGAGCTGGTGAGTACAATCA<br>GTGATGACGGATCTACCTACTATGCCGACAGCGTCAAGG<br>GAAGATCCAGCATCAGTCGCGACAACGCCAAGAGCACC<br>GTTTACCTCCAGATGAACCGCCTCAAGCCTGAGGACACA<br>GGAGTCTATTACTGTGCTGCGGAGGGGCCTTGGGCAGC<br>AAGACTAACTGTGGATGGGTGGGAAACTTCGGGTATTGG<br>GGTCAGGGTACACAGGTCACAGTGTCTTCA | 185 |
| mIL2Rg_VHH11 | CAAGTTCAGCTTCAGGAAAGTGGGGCGGGCTGGTGCA<br>GCCAGGGGGTTCCCTGAAGCTGAGCTGCGCTGCCTCTGG<br>GTTTACATTCTCTGATCGCGACATGGGCTGGTATCGCCA<br>AGCGCCGGGCAATGAATGCGAAAGAGTGAGTACTATTTC<br>TGACGATGGTTCTACTTACTATGCTGACTCCGTGAAGGG<br>CCGTAGCTCCATTTCCAGGGACAACGCGAAGAACACCGT<br>ATACCTCCAGATGAACTCTCTGAAGCCCGAGGACACCGC<br>TGTGTATTACTGCGCTGCCGAGGGGGCTCTCGGCTCAAA | 186 |

TABLE 4-continued

DNA Sequences Encoding mIL2Rg VHHs

| Name | DNA Sequence | SEQ ID NO |
|---|---|---|
| | GACCAACTGCGGATGGGTCGGTAACTTCGGCTACTGGGG<br>CCAGGGCACCCAAGTGACAGTCTCCTCC | |
| mIL2Rg_VHH12 | CAGGTCCAGTTGCAGGAGAGCGGGGGTGGAAGCGTCCT<br>CGCCGGAGGGAGCCTCCGTTTGAGCTGCGTCGCCTCAGG<br>CTACGGCTACAATTACATCGGATGGTTCAGACAGACGCC<br>TGGTAAAGAGCGGGAAGGCGTCGCCGTGATTTATATCGG<br>TGGCGGAGACACCTATTACGCTGACTCAGTGAAGGGGCG<br>TTTCACCGCAAGCCGGGACAACGCTAAGAGCACCCTGTA<br>CCTCCAGATGAACTCTCTCGAACCTGAGGACACTGCAAT<br>GTATTACTGCGTGGCTCGTTACTGCGTCGGGAGTGTCTA<br>CGCCTGCCTGAGGGGCGGGCATGATGAGTATGCCCACTG<br>GGGACAAGGAACACAGGTGACTGTCTCCAGT | 187 |
| mIL2Rg_VHH13 | CAGGTTCAGCTCCAGGAGTCTGGTGGCGGTTCCGTGCTG<br>GCCGGGGGCTCTCTGCGCCTGTCTTGTGTCGCCTCAGGG<br>TACGGCTATAACTACATTGGCTGGTTCAGACAGACCCCT<br>GGGAAAGAGCGGGAGGGTGTGGCTGTCATTTACACCGG<br>CGGAGGCGACACCTACTATGCCGATTCAGTTAAGGGCAG<br>GTTTACCGCGAGCCGTGACAACGCGAAGTCTACTCTGTA<br>CCTGCAAATGAACAGCCTGGAACCTGAGGATACTGCGAT<br>GTACTATTGTGTGGCCCGGTACTGCGTAGGCTCAGTGTA<br>TGCCTGCCTGCGCGGGGGTCACGACGAGTACGCACACTG<br>GGGACAGGGAACTCAGGTCACCGTGTCTAGC | 188 |
| mIL2Rg_VHH14 | CAGGTGCAACTCCAGGAGTCCGGCGGGGGCTCCGTCCAA<br>GCTGGTGGCTCACTGAGGCTTAGCTGTGCTGCCTCCGGC<br>TTTACTTTCGACGATTTCGACATGGGTTGGTATCGCCAGG<br>CTCCGGGCAATGAGTGCGAGCTGGTCTCTACCATTTCCG<br>ATGACGGCTCTACCTACTATGCCAACAGTGTTAAGGGTA<br>GGTCTTCCATCTCCCGCGACAACGCTAAGAATATGGTGT<br>ACTTGCAGATGAACTCTCTGAAGCCTGAGGACACTGCTG<br>TCTACTATTGCGCTGCCGAAGGTGCCCTGGGCTCAAAGA<br>CTAATTGCGGCTGGGTCGGTAACTTTGGCTACTGGGGTC<br>AGGGGACTCAGGTGACCGTCAGCTCC | 189 |
| mIL2Rg_VHH15 | CAGGTCCAGTTGCAGGAAAGCGGCGGGGGCTCTGTTCAG<br>GCAGGCGGAAGCCTTCGTCTGTCCTGTACTGCCAGTGGT<br>TTCACCTTTGATGACTTTGACATGGGCTGGTATCGGCAA<br>GCCCCCGGAAACGAGTGCGAGCTGGTATCCACCATTTCC<br>GATGACGGGTCCACGTACTATGCTGATAGCGTGAAGGGC<br>AGGTCTTCCATCAGCCGGGACAACGCCAAGAACACAGT<br>GTATTTGCAGATGAACCGCCTCAAGCCAGAAGACACCGG<br>GGTATATTACTGTGCAGCGGAAGGTGCCCTGGGTAGCAA<br>GATGAACTGCGGATGGGTGGGTAATTTTGGATACTGGGG<br>CCAGGGCACGCAGGTTACAGTGTCCAGC | 190 |

In some embodiments, the murine IL2Rg binding molecules are useful as surrogates of the human IL2Rg molecules for evaluating activity in mouse models.

The disclosure further provides recombinant viral and non-viral vectors comprising a nucleic acid encoding the IL2Rg binding molecules of the present disclosure or the CDRs of the IL2Rg binding molecules of the present disclosure.

The disclosure further provides host cells comprising recombinant viral and non-viral vectors comprising a nucleic acid the IL2Rg binding molecules of the present disclosure or the CDRs of the IL2Rg binding molecules of the present disclosure.

The disclosure further provides host cells comprising recombinant viral and non-viral vectors comprising a nucleic acid the IL2Rg binding molecules of the present disclosure or the CDRs of the IL2Rg binding molecules of the present disclosure.

The disclosure further provides pharmaceutical formulations comprising the recombinant viral and non-viral vectors comprising a nucleic acid the IL2Rg binding molecules of the present disclosure and methods of use thereof in the treatment or prevention of diseases, disorders or conditions in a mammalian subject.

The disclosure further kits comprising the IL2Rg binding molecules of the present disclosure.

In another aspect, the present disclosure provides constructs for the targeted delivery of therapeutic agents to a cell expressing the IL2Rg receptor, wherein the IL2Rg binding molecule is conjugated to one or more therapeutic agents, optionally through a chemical or polypeptide linker. The disclosure further provides methods of use of the foregoing in the treatment of disease associated with expression of the IL2Rg in a subject, the method comprising the administration of a therapeutically effective amount of the IL2Rg binding molecule conjugated to the therapeutic agent to a subject in need to treatment, alone or in combination with one or more additional therapeutic agents. In some embodiments, the diseases amenable to treatment are diseases, disorders or conditions associated with signaling from receptor comprising the IL2Rg. In some embodiments, the IL2Rg binding molecules of the present disclosure are useful in the treatment of diseases associated with dysregulated T cell or B cell activity. In some embodiments, the IL2Rg binding molecules of the present disclosure are useful in the treatment of autoimmune disease associated with aberrant cell activity arising from dysregulated signaling in cells expressing the IL2Rg. In some embodiments, the IL2Rg binding molecules of the present disclosure are useful in the treatment of neoplastic diseases associated with aberrant cell activity arising from dysregulated signaling in cells expressing the IL2Rg.

In another aspect, the present disclosure provides constructs for the identification of cells expressing the IL2Rg receptor wherein the IL2Rg binding molecule is conjugated to one or more imaging agents, optionally through a chemical or polypeptide linker. The disclosure further provides methods of use of the foregoing in the identification of cells expressing the IL2Rg receptor in a subject, the method comprising the administration of a effective amount of the IL2Rg binding molecule conjugated to the imaging agent to a subject in need to treatment and evaluating the subject for the presence of the imaging agent that is conjugated to the IL2Rg binding molecule.

In another aspect, the present disclosure provides IL2Rg binding molecules which have been modified for extended duration of action in vivo wherein the IL2Rg binding molecule is conjugated to one or more carrier molecules.

The present disclosure provides IL2Rg binding molecules comprising a polypeptide sequence that specifically binds to the extracellular domain of the IL2Rg and methods of use thereof in the isolation, depletion or enrichment of cells expressing the IL2Rg cells a biological sample.

In some embodiments, the IL2Rg binding molecules of the present disclosure are competitive inhibitors of IL2. In some embodiments, the IL2Rg binding molecules of the present disclosure are useful in inhibiting the activity of IL2 or IL2 muteins, in particular the T cell proliferative and/or activating functions of IL2.

DETAILED DESCRIPTION OF THE INVENTION

Introduction

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this disclosure is not limited to particular method or composition described, as such may, of course, vary.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It will be appreciated that throughout this disclosure reference is made to amino acids according to the single letter or three letter codes. For the reader's convenience, the single and three letter amino acid codes are provided in below:

TABLE 5

Amino Acid Abbreviations

| Name | 3 Letter Abbreviation | 1-letter abbreviation |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g., an assay) or biological or chemical property (e.g., the degree of binding of the molecule to another molecule) or of a physical property of a material or cell (e.g., modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [proliferation]/[mg protein], plaque forming units (pfu), etc. As used herein, the term proliferative activity refers to an activity that promotes cell proliferation and replication, including dysregulated cell division such as that observed in neoplastic diseases, inflammatory diseases, fibrosis, dysplasia, cell transformation, metastasis, and angiogenesis.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g., an a IL2Rg binding molecule or an engineered cell expressing an IL2Rg binding molecule, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, intracranial injection, intratumoral injection, transdermal, transmucosal, iontophoretic delivery, intralymphatic injection, intragastric infusion, intraprostatic injection, intravesical infusion (e.g., bladder), inhalation (e.g respiratory inhalers including dry-powder inhalers), intraocular injection, intraabdominal injection, intralesional injection, intraovarian injection, intracerebral infusion or injection, intracerebroventricular injection (ICVI), and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant (KD), a ratio of the dissociation rate constant between the molecule and its target (Koff) and the association rate constant between the molecule and its target (Kon).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state resulting in a biological response that mimics the effect of the endogenous ligand of the receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that can produce a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or downregulate, e.g., a gene, protein, ligand, receptor, biological pathway including an immune checkpoint pathway, or cell.

Antibody: As used herein, the term "antibody" refers collectively to: (a) a glycosylated or non-glycosylated immunoglobulin that specifically binds to target molecule, and (b) immunoglobulin derivatives thereof, including but not limited to antibody fragments such as single domain antibodies. In some embodiments the immunoglobulin derivative competes with the immunoglobulin from which it was derived for binding to the target molecule. The term antibody is not restricted to immunoglobulins derived from any particular species and includes murine, human, equine, camelids, antibodies of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies, camelized (in the case of VHHs), or molecules comprising binding domains of antibodies (e.g., CDRs) in non-immunoglobulin scaffolds. The term "antibody" should not be construed as limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries. In one embodiment, an "antibody" is a mammalian immunoglobulin of the IgG1, IgG2, IgG3 or IgG4 class. In some embodiments, the antibody is a "full length antibody" comprising variable and constant domains providing binding and effector functions.

The term "single domain antibody" (sdAb) as used herein refers an antibody fragment consisting of a monomeric variable antibody domain that is able to bind specifically to an antigen and compete for binding with the parent antibody from which it is derived. The term "single domain antibody" includes scFv and VHH molecules. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks.

Biological Sample: As used herein, the term "biological sample" or "sample" refers to a sample obtained (or derived) from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, tumor tissue, including immunoglobulin enriched or cell-type specific enriched fractions derived from one or more of such tissues.

IL2Rg cell: The terms "IL2Rg cell", "IL2Rg-expressing cell", "IL2Rg-positive cell" and "IL2Rg+" cell are used interchangeably herein to refer to a cell which expresses and displays the IL2Rg antigen on the extracellular surface of the cell membrane. Similarly, the terms "IL2Rg-negative cell", "IL2Rg-cells" as are used interchangeably herein to describe cells which do not express or display IL2Rg antigen on the cell surface.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., J. Biol. Chem. 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. In the context of the present disclosure, unless otherwise specified, the numbering of the CDR positions is provided according to the Kabat numbering convention.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 35%, alternatively by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Conservative Amino Acid Substitution: As used herein, the term "conservative amino acid substitution" refers to an amino acid replacement that changes a given amino acid to a different amino acid with similar biochemical properties (e.g., charge, hydrophobicity, and size). For example, the amino acids in each of the following groups can be considered as conservative amino acids of each other: (1) hydrophobic amino acids: alanine, isoleucine, leucine, tryptophan, phenylalanine, valine, proline, and glycine; (2) polar amino acids: glutamine, asparagine, histidine, serine, threonine, tyrosine, methionine, and cysteine; (3) basic amino acids: lysine and arginine; and (4) acidic amino acids: aspartic acid and glutamic acid.

Derived From: As used herein in the term "derived from", in the context of an amino acid sequence is meant to indicate that the polypeptide or nucleic acid has a sequence that is based on that of a reference polypeptide or nucleic acid and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological response observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (about 50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect.

Enriched: As used herein in the term "enriched" refers to a sample that is non-naturally manipulated so that a species (e.g., a molecule or cell) of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein (e.g., a cell surface receptor) which is external to of the plasma membrane of a cell. The cell surface protein may be transmembrane protein, a cell surface or membrane associated protein.

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as BLAST 2.0 algorithms, which are described in Altschul et al. (1990) *J. Mol. Biol.* 215: 403-410 and Altschul, et al. (1977) *Nucleic Acids Res.* 25: 3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0). For amino acid sequences, a scoring matrix is used to calculate the cumulative score. Extension of the word hits in each direction are halted when: (a) the cumulative alignment score falls off by the quantity X from its maximum achieved value; the cumulative score goes to zero or below, due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) PNAS(USA) 89:10915-10919).

In An Amount Sufficient Amount to Cause a Response: As used herein the phrase "in an amount sufficient to cause a response" is used in reference to the amount of a test agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

In Need of Treatment: The term "in need of treatment" as used herein refers to a judgment made by a physician or other caregiver with respect to a subject that the subject requires or will potentially benefit from treatment. This judgment is made based on a variety of factors that are in the realm of the physician's or caregiver's expertise.

In Need of Prevention: As used herein the term "in need of prevention" refers to a judgment made by a physician or other caregiver with respect to a subject that the subject requires or will potentially benefit from preventative care. This judgment is made based upon a variety of factors that are in the realm of a physician's or caregiver's expertise.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Intracellular Domain: As used herein the tern "intracellular domain" or its abbreviation "ICD" refers to the portion of a cell surface protein (e.g., a cell surface receptor) which is inside of the plasma membrane of a cell. The ICD may include the entire cytoplasmic portion of a transmembrane protein or membrane associated protein, or intracellular protein.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., *J. Biol. Chem.* 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs2 and 3 in the variable region of an antibody follows Kabat numbering or simply, "Kabat." The positioning of CDR1 in the variable region of an antibody follows a hybrid of Kabat and Chothia numbering schemes.

Ligand: As used herein, the term "ligand" refers to a molecule that specifically binds a receptor and causes a change in the receptor so as to effect a change in the activity of the receptor or a response in cell that expresses that receptor. In one embodiment, the term "ligand" refers to a molecule or complex thereof that can act as an agonist or antagonist of a receptor. As used herein, the tern "ligand" encompasses natural and synthetic ligands. "Ligand" also encompasses small molecules, peptide mimetics of cytokines and antibodies. The complex of a ligand and receptor is termed a "ligand-receptor complex." A ligand may comprise one domain of a polyprotein or fusion protein (e.g., either domain of an antibody/ligand fusion protein).

Modulate: As used herein, the terms "modulate", "modulation" and the like refer to the ability of a test agent to cause a response, either positive or negative or directly or indirectly, in a system, including a biological system, or biochemical pathway. The term modulator includes both agonists (including partial agonists, full agonists and superagonists) and antagonists.

Neoplastic Disease: As used herein, the tern "neoplastic disease" refers to disorders or conditions in a subject arising from cellular hyper-proliferation or unregulated (or dysregulated) cell replication. The term neoplastic disease refers to disorders arising from the presence of neoplasms in the subject. Neoplasms may be classified as: (1) benign (2) pre-malignant (or "pre-cancerous"); and (3) malignant (or "cancerous"). The term "neoplastic disease" includes neoplastic-related diseases, disorders and conditions referring to conditions that are associated, directly or indirectly, with neoplastic disease, and includes, e.g., angiogenesis and precancerous conditions such as dysplasia or smoldering multiple myeloma. Examples of benign disorders arising from dysregulated cell replication include hypertrophic scars such as keloid scars.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally, in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Parent Polypeptide: As used herein, the terms "parent polypeptide" or "parent protein" are used interchangeably to designate the source of a second polypeptide (e.g., a derivative, mutein or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g., glycosylated or PEGylated forms and/or fusion proteins comprising the parent polypeptide).

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Partial agonists can be used to activate receptors to give a desired submaximal response in a subject when inadequate amounts of the endogenous ligand are present, or they can reduce the overstimulation of receptors when excess amounts of the endogenous ligand are present. The maximum response ($E_{max}$) produced by a partial agonist is called its intrinsic activity and may be expressed on a percentage scale where a full agonist produced a 100% response. An partial agonist may have greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the reference polypeptide when evaluated at similar concentrations in a given assay system.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g., antigenic diphtheria or tetanus toxin or toxoid fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof. A course of action to prevent a disease, disorder or condition in a subject is typically applied in the context of a subject who is predisposed to developing a disease, disorder or condition due to genetic, experiential or environmental factors of developing a particular disease, disorder or condition. In certain instances, the terms "prevent", "preventing", "prevention" are also used to refer to the slowing of the progression of a disease, disorder or condition from an existing state to a more deleterious state.

Receptor: As used herein, the term "receptor" refers to a polypeptide having a domain that specifically binds a ligand that binding of the ligand results in a change to at least one biological property of the polypeptide. In some embodiments, the receptor is a cell membrane associated protein that comprises and extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of a cognate ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface receptor that is not associated with any intracellular signaling alone but upon ligand binding facilitates the formation of a heteromultimeric (including heterodimeric, heterotrimeric, etc.) or homomultimeric (including homodimeric, homotrimeric, homotetrameric, etc.) complex that results in a measurable biological effect in the cell such as activation of an intracellular signaling cascade (e.g., the Jak/STAT pathway). In some embodiments, a receptor is a membrane spanning single chain polypeptide comprising ECD, TM and TCD domains wherein the ECD, TM and ICD domains are derived from the same or differing naturally occurring receptor variants or synthetic functional equivalents thereof.

Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of viable cells present in culture as described in Crouch, et al. (1993) J. Immunol. Methods 160: 81-8 or using commercially available assays such as the CellTiter-Glo® 2.0 Cell Viability Assay or CellTiter-Glo® 3D Cell Viability kits commercially available from Promega Corporation, Madison WI 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art.

Significantly Reduced Binding: As used herein, the term "exhibits significantly reduced binding" is used with respect a variant of a first molecule (e.g., a ligand or antibody) which exhibits a significant reduction in the affinity for a second molecule (e.g., receptor or antigen) relative the parent form of the first molecule. With respect to antibody variants, an antibody variant "exhibits significantly reduced binding" if the affinity of the variant antibody for an antigen if the variant binds to the native form of the receptor with and affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent antibody from which the variant was derived. Similarly, with respect to variant ligands, a variant ligand "exhibits significantly reduced binding" if the affinity of the variant ligand binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived. Similarly, with respect to variant receptors, a variant ligand "exhibits significantly reduced binding" if the affinity of the variant receptors binds to a with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent receptor from which the variant receptor was derived.

Small Molecule(s): The term "small molecules" refers to chemical compounds (typically pharmaceutically active compounds) having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. The term "small molecule" is a term well understood to those of ordinary skill in the pharmaceutical arts and is typically used to distinguish organic chemical compounds from biologics.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant between antibody and the antigen is greater than about $10^6$ M, alternatively greater than about $10^8$ M, alternatively greater than about $10^{10}$ M, alternatively greater than about $10^7$ M, greater than about $10^{12}$ M as determined by, e.g., Scatchard analysis (Munsen, et al. (1980) Analyt. Biochem. 107:220-239). In one embodiment where the ligand is an IL2Rg binding sdAb and the receptor comprises an IL2Rg, the IL2Rg binding sdAb specifically binds if the equilibrium dissociation constant of the IL2Rg binding sdAb/IL2Rg ECD is greater than about $10^5$M, alternatively greater than about $10^6$ M, alternatively greater than about $10^7$M, alternatively greater than about $10^8$M, alternatively greater than about 109 M, alternatively greater than about $10^{10}$ M, or alternatively greater than about $10^{11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8K, Biacore 8K+, Biacore S200, Biacore T200 (Cytiva, 100 Results Way, Marlborough MA 01752). In some embodiments, the present disclosure provides molecules (e.g., IL2Rg binding sdAbs) that specifically bind to the hIL2Rg isoform.

As used herein, the binding affinity of an IL2Rg binding molecule for the CD122, the binding affinity may be determined and/or quantified by surface plasmon resonance ("SPR"). In evaluating binding affinity of an IL2Rg binding molecule for the CD122, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough MA as catalog number BR100407), as anti-His tag antibodies (e.g. anti-histidine CM5 chips commercially available from Cytiva, Marlborough MA), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising poly-histidine sequence (e.g., 6×His (SEQ ID NO: 195) or 8×His (SEQ ID NO: 196)) for retention on a chip conjugated with NTA. In some embodiments, the IL2Rg binding molecule may be immobilized on the chip and CD122 (or ECD fragment thereof) be provided in the mobile phase. Alternatively, the CD122 (or ECD fragment thereof) may be immobilized on the chip and the IL2Rg binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of IL2Rg binding molecule for CD122 using SPR, the IL2Rg binding molecule may be derivatized by the C-terminal addition of a poly-His sequence (e.g., 6×His (SEQ ID NO: 195) or 8×His (SEQ ID NO: 196)) and immobilized on the NTA derivatized sensor chip and the hIL2 receptor subunit for which binding affinity is being evaluated is provided in the mobile phase. The means for incorporation of a poly-His sequence into the C-terminus of the IL2Rg binding molecule produced by recombinant DNA technology is well known to those of skill in the relevant art of biotechnology. In some embodiments, the binding affinity of IL2Rg binding molecule for a IL2Rg using SPR substantial accordance with the teaching of the Examples.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95% of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95% of the total content of the composition.

Suffering From: As used herein, the term "suffering from" refers to a determination made by a physician with respect to a subject based on the available objective or subjective information accepted in the field for the identification of a disease, disorder or condition including but not limited to X-ray, CT-scans, conventional laboratory diagnostic tests (e.g., blood count, etc.), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

T-cell: As used herein the term "T-cell" or "T cell" is used in its conventional sense to refer to a lymphocytes that differentiates in the thymus, possess specific cell-surface antigen receptors, and include some that control the initiation or suppression of cell-mediated and humoral immunity and others that lyse antigen-bearing cells. In some embodiments the T cell includes without limitation naïve CD8$^+$ T cells, cytotoxic CD8$^+$ T cells, naïve CD4$^+$ T cells, helper T cells, e.g., $T_H1$, $T_H2$, $T_H9$, $T_H11$, $T_H22$, $T_{FH}$; regulatory T cells, e.g., TRI, Tregs, inducible Tregs; memory T cells, e.g., central memory T cells, effector memory T cells, NKT cells, tumor infiltrating lymphocytes (TILs) and engineered variants of such T-cells including but not limited to CAR-T cells, recombinantly modified TILs and TCR-engineered cells. In some embodiments the T cell is a T cell expressing the IL2Rg isoform referred to interchangeably as IL2Rg cell, IL2Rg+cell, IL2Rg T cell, or IL2Rg+T cell).

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Therapeutically Effective Amount: As used herein to the phrase "therapeutically effective amount" refers to the quantity of an agent when administered to a subject, either alone or as part of a pharmaceutical composition or treatment regimen, in a single dose or as part of a series of doses, provides a positive effect on any quantitative or qualitative symptom, aspect, or characteristic of a disease, disorder or condition. A therapeutically effective amount can be ascertained by measuring relevant physiological effects, and it may be adjusted in connection with a dosing regimen and in response to diagnostic analysis of the subject's condition. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, biomarkers (such as inflammatory cytokines, IFN-γ, granzyme, and the like), reduction in serum tumor markers, improvement in Response Evaluation Criteria In Solid Tumors (RECIST), improvement in Immune-Related Response Criteria (irRC), increase in duration of survival, extended duration of progression free survival, extension of the time to progression, increased time to treatment failure, extended duration of event free survival, extension of time to next treatment, improvement objective response rate, improvement in the duration of response, reduction of tumor burden, complete response, partial response, stable disease, and the like that that are relied upon by clinicians in the field for the assessment of an improvement in the condition of the subject in response to administration of an agent. In one embodiment, a therapeutically effective amount is an amount of an agent when used alone or in combination with another agent provides an provides a positive effect on any quantitative or qualitative symptom, aspect, or characteristic of a disease, disorder or condition and does not result in non-reversible serious adverse events in the course of administration of the agent to the mammalian subject.

Transmembrane Domain: The term "transmembrane domain" or "TM" refers to a polypeptide domain of a membrane spanning polypeptide (e.g., a transmembrane receptor) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treat: The terms "treat", "treating", treatment" and the like refer to a course of action (such as contacting the subject with pharmaceutical composition comprising a IL2Rg binding sdAb alone or in combination with a supplementary agent) that is initiated with respect to a subject in response to a diagnosis that the subject is suffering from a disease, disorder or condition, or a symptom thereof, the course of action being initiated so as to eliminate, reduce, suppress, mitigate, or ameliorate, either temporarily or permanently, at least one of: (a) the underlying causes of such disease, disorder, or condition afflicting a subject; and/or (b) at least one of the symptoms associated with such disease, disorder, or condition. In some embodiments, treating includes a course of action taken with respect to a subject suffering from a disease where the course of action results in the inhibition (e.g., arrests the development of the disease, disorder or condition or ameliorates one or more symptoms associated therewith) of the disease in the subject.

Treg Cell or Regulatory T Cell. The terms "regulatory T cell", "Treg cell", or "Treg" are interchangeably herein to refers to a type of CD4⁺ T cell that can suppress the responses of other T cells including but not limited to effector T cells (Teff). Treg cells are typically characterized by expression of CD4 (CD4+), the CD25 subunit of the IL2 receptor (CD25+), and the transcription factor forkhead box P3 (FOXP3+) (Sakaguchi, Annu Rev Immunol 22, 531-62 (2004). In some instances, the term "conventional CD4⁺ T cells" is used to distinguish non-Treg CD4⁺ T cells from CD4⁺ Tregs.

Variant: The terms "variant", "protein variant" or "variant protein" or "variant polypeptide" are used interchangeably herein to refer to a polypeptide that differs from a parent polypeptide by virtue of at least one amino acid modification, substitution, or deletion. The parent polypeptide may be a naturally occurring or wild-type (WT) polypeptide or may be a modified version of a WT polypeptide. The term variant polypeptide may refer to the polypeptide itself, a composition comprising the polypeptide, or the nucleic acid sequence that encodes it. In some embodiments, the variant polypeptide comprises from about one to about ten, alternatively about one to about eight, alternatively about one to about seven, alternatively about one to about five, alternatively about one to about four, alternatively from about one to about three alternatively from one to two amino acid modifications, substitutions, or deletions, or alternatively a single amino acid amino acid modification, substitution, or deletion compared to the parent polypeptide. A variant may be at least about 99% identical, alternatively at least about 98% identical, alternatively at least about 97% identical, alternatively at least about 95% identical, or alternatively at least about 90% identical to the parent polypeptide from which the variant is derived.

Wild Type: By "wild type" or "WT" or "native" herein is meant an amino acid sequence or a nucleotide sequence that is found in nature, including allelic variations. A wild-type protein, polypeptide, antibody, immunoglobulin, IgG, etc. has an amino acid sequence or a nucleotide sequence that has not been modified by the hand of man.

IL2Rg

The IL2Rg binding molecules of the present disclosure specifically bind to the extracellular domain of the IL2Rg.

Human IL2Rg

The IL2Rg binding molecules of the present disclosure specifically bind to the extracellular domain of the IL2Rg (CD132). In one embodiment, the IL2Rg is the human IL2Rg. The canonical full length IL2Rg (including the signal peptide) is a polypeptide possessing the amino acid sequence:

```
                                              (SEQ ID NO 191)
MLKPSLPFTSLLFLQLPLLGVGLNTTILTPNGNEDTTADFFLTTMPTDS

LSVSTLPLPEVQCFVFNVEYMNCTWNSSSEPQPTNLTLHYWYKNSDNDK

VQKCSHYLFSEEITSGCQLQKKEIHLYQTFVVQLQDPREPRRQATQMLK

LQNLVIPWAPENLTLHKLSESQLELNWNNRFLNHCLEHLVQYRTDWDHS

WTEQSVDYRHKFSLPSVDGQKRYTFRVRSRFNPLCGSAQHWSEWSHPIH

WGSNTSKENPFLFALEAVVISVGSMGLIISLLCVYFWLERTMPRIPTLK

NLEDLVTEYHGNFSAWSGVSKGLAESLQPDYSERLCLVSEIPPKGGALG

EGPGASPCNQHSPYWAPPCYTLKPET.
```

To generate sdAbs against the human IL2Rg, the extracellular domain of the hIL2Rg protein was used as an immunogen. The extracellular domain of the mature (lacking the signal sequence) hIL2Rg possesses the amino acid sequence:

```
                                              (SEQ ID NO: 192)
LNTTILTPNGNEDTTADFFLTTMPTDSLSVSTLPLPEVQCFVFNVEYMN

CTWNSSSEPQPTNLTLHYWYKNSDNDKVQKCSHYLFSEEITSGCQLQKK

EIHLYQTFVVQLQDPREPRRQATQMLKLQNLVIPWAPENLTLHKLSESQ

LELNWNNRFLNHCLEHLVQYRTDWDHSWTEQSVDYRHKFSLPSVDGQKR

YTFRVRSRFNPLCGSAQHWSEWSHPIHWGSNTSKENPFLFALEA
```

For purposes of the present disclosure, the numbering of amino acid residues of the human IL2Rg (hIL2Rg) polypeptides as described herein is made in accordance with the numbering of this canonical sequence (UniProt ID: 31785; SEQ ID NO:191). Amino acids 1-22 of SEQ ID NO: 191 are identified as the signal peptide of hIL2Rg, amino acids 23-262 of SEQ ID NO:191 are identified as the extracellular domain, amino acids 263-283 SEQ ID NO:191 are identified as the transmembrane domain, and amino acids 284-269 of SEQ ID NO:191 are identified as the intracellular domain.

Murine IL2Rg

In one embodiment, the IL2Rg is the murine IL2Rg. The murine CD132 (mCD132) is expressed as a 369 amino acid precursor, the first 22 amino acids comprising a signal sequence which is post-translationally cleaved to provide the mature 353 amino acid protein. Amino acids 23-263 (amino acids 1-214 of the mature protein) correspond to the extracellular domain, amino acids 264-284 (amino acids 242-266 of the mature protein) correspond to the transmembrane domain and amino acids 285-369 (amino acids 263-347 of the mature protein) correspond to the intracellular domain. The canonical full length mIL2Rg precursor protein including the signal sequence is a polypeptide of the amino acid sequence:

(SEQ ID NO: 193)
MLKLLLSPRSFLVLQLLLLRAGWSSKVLMSSANEDIKADLILTSTAPEH

LSAPTLPLPEVQCFVFNIEYMNCTWNSSSEPQATNLTLHYRYKVSDNNT

FQECSHYLFSKEITSGCQIQKEDIQLYQTFVVQLQDPQKPQRRAVQKLN

LQNLVIPRAPENLTLSNLSESQLELRWKSRHIKERCLQYLVQYRSNRDR

SWTELIVNHEPRFSLPSVDELKRYTFRVRSRYNPICGSSQQWSKWSQPV

HWGSHTVEENPSLFALEAVLIPVGTMGLIITLIFVYCWLERMPPIPPIK

NLEDLVTEYQGNFSAWSGVSKGLTESLQPDYSERFCHVSEIPPKGGALG

EGPGGSPCSLHSPYWPPPCYSLKPEA

To generate sdAbs against mIL2Rg, the extracellular domain of the mIL2Rg protein was used as an immunogen. The extracellular domain of the mature (lacking the signal sequence) hIL2Rg possesses the amino acid sequence (amino acids 23-263):

(SEQ ID NO: 194)
WSSKVLMSSANEDIKADLILTSTAPEHLSAPTLPLPEVQCFVFNIEYMN

CTWNSSSEPQATNLTLHYRYKVSDNNTFQECSHYLFSKEITSGCQIQKE

DIQLYQTFVVQLQDPQKPQRRAVQKLNLQNLVIPRAPENLTLSNLSESQ

LELRWKSRHIKERCLQYLVQYRSNRDRSWTELIVNHEPRFSLPSVDELK

RYTFRVRSRYNPICGSSQQWSKWSQPVHWGSHTVEENPSLFALEA

For purposes of the present disclosure, the numbering of amino acid residues of the murine IL2Rg polypeptides as described herein is made in accordance with the numbering of this canonical sequence (UniProt ID: P34902). Amino acids 1-22 of SEQ ID NO:193 are identified as the signal peptide of the IL2Rg, amino acids 23-263 of SEQ ID NO:193 are identified as the extracellular domain, amino acids 264-284 of SEQ ID NO: 193 are identified as the transmembrane domain, and amino acids 285-369 of SEQ ID NO: 193 are identified as the intracellular domain.

IL2Rg Binding Molecules and Single Domain Antibodies

In some embodiments, a IL2Rg binding molecule of the present disclosure is a single domain antibody (sdAb). The present disclosure relates to IL2Rg binding molecules comprising single domain antibodies (sdAbs) that specifically bind to the extracellular domain of the human IL2Rg isoform (hIL2Rg) which are found on all IL2Rg-expressing cells.

A single-domain antibody (sdAb) is an antibody containing a single monomeric variable antibody domain. Like a full-length antibody, sdAbs bind specifically to an antigenic determinant of a protein. hIL2Rg binding VHH single-domain antibodies can be engineered from heavy chain antibodies isolated from Camelidae mammals (e.g., camels, llamas, dromedary, alpaca, and guanaco) immunized with the extracellular domain of hIL2Rg or an immunologically active fragment thereof. Descriptions of sdAbs and VHHs can be found in, e.g., De Greve et al., (2019) Curr Opin Biotechnol. 61:96-101; Ciccarese, et al., (2019) Front Genet. 10:997: Chanier and Chames (2019) *Antibodies* (Basel) 8(1); and De Vlieger, et al. (2018) *Antibodies* (Basel) 8(1). Alternatively, hIL2Rg single domain antibodies may be engineered from heavy chain antibodies isolated from the IgNAR heavy chain antibodies isolated from cartilaginous fishes immunized with the extracellular domain of hIL2Rg or an immunologically active fragment thereof. hIL2Rg binding sdAbs may also be obtained by splitting the dimeric variable domains from immunoglobulin G (IgG) isotypes from other mammalian species including humans, rats, rabbits immunized with the extracellular domain of hIL2Rg or an immunologically active fragment thereof. Although most research into sdAbs is currently based on heavy chain variable domains, sdAbs derived from light chains have also been shown to bind specifically to the target proteins comprising the antigenic immunization sequence. Moller et al., *J Biol Chem*. 285(49):38348-38361, 2010.

In some embodiments, the sdAb is a VHH. A VHH is a type of sdAb that has a single monomeric heavy chain variable antibody domain. Similar to a traditional antibody, a VHH is able to bind specifically to a specific antigen. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains.

The present disclosure provides IL2Rg binding molecules comprising a polypeptide having at least 75%, alternatively 80%, alternatively 90%, alternatively 95%, alternatively 98%, or alternatively 99% or 100% identity to a polypeptide of any one of SEQ ID NOS:1, 5, 9, 13, 17, 21, 25, 29, 33, 37, 41, 45, 49, 53, 57, 61, 65, 69, 73, 77, 81, 85 and 89.

The present disclosure provides IL2Rg binding molecules comprising a polypeptide having at least 75%, alternatively 80%, alternatively 90%, alternatively 95%, alternatively 98%, or alternatively 99% or 100% identity to a polypeptide of any one of SEQ ID NOS: 116, 120, 124, 128, 132, 136, 140, 144, 148, 152, 156, 160, 164, 168, and 172.

The present disclosure provides IL2Rg binding molecules comprising a CDR1, a CDR2, and a CDR3 as described in a row of Table 1 provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 1 provided herein.

The present disclosure provides IL2Rg binding molecules comprising a CDR1, a CDR2, and a CDR3 as described in a row of Table 3 provided herein. In some embodiments, the CDR1, CDR2, and CDR3 can each, independently, comprise at least 90% (e.g., 91%, 92%, 93%, 94%, 95%, 96%, 97%, 98%, 99%, or 100%) sequence identity, or have 0, 1, 2, or 3 amino acid changes, optionally conservative amino acid changes, relative to the sequence described in a row of Table 3 provided herein.

accordance with the foregoing, representative examples of each of the human VHH clonotypes were subjected to analysis of by surface plasmon resonance in substantial accordance with the teaching of Example 5 herein. The results of these SPR studies are summarized in Table 6 below.

TABLE 6 anti-hIL2Rg Mono-Fc VHHs binding to hIL2Rg-his
(Antigen: Sino Biological, Catalog# 10555)

| Ligand | SEQ ID NO | $k_{ON}$ (1/Ms) | $k_{OFF}$ (1/s) | Affinity (nM) | Rmax (RU) | Load (RU) | Calc. Rmax (RU) | Surface Activity |
|---|---|---|---|---|---|---|---|---|
| hIL-2Rg_VHH8 | 30 | 3.66E+05 | 8.12E−04 | 2.2 | 41.6 | 49.3 | 38 | 110% |
| hIL-2Rg_VHH15 | 62 | 9.68E+04 | 2.51E−03 | 26 | 47.1 | 84 | 64 | 73% |
| hIL-2Rg_VHH19 | 73 | 2.85E+06 | 6.93E−03 | 2.4 | 7 | 28 | 21 | 33% |
| hIL-2Rg_VHH20 | 77 | 1.92E+05 | 2.70E−03 | 14.1 | 227 | 103 | 475.4 | 48% |
| hIL-2Rg_VHH21 | 81 | 6.56E+04 | 1.13E−03 | 17.2 | 14.6 | 57.5 | 245.8 | 6% |
| hIL-2Rg_VHH22 | 85 | 5.54E+05 | 3.54E−03 | 6.4 | 39.6 | 47.8 | 37 | 108% |

Experimental

The single domain antibodies of the present disclosure were obtained from camels by immunization with an extracellular domain of a IL2Rg receptor (CD132). IL2Rg VHH molecules of the present disclosure of the present disclosure were generated in substantial accordance with the teaching of the Examples. Briefly, a camel was sequentially immunized with the ECD of the human IL2Rg and mouse IL2Rg over a period several weeks of by the subcutaneous an adjuvanted composition containing a recombinantly produced fusion proteins comprising the extracellular domain of the IL2Rg, the human IgG1 hinge domain and the human IgG1 heavy chain Fc. Following immunization, RNAs extracted from a blood sample of appropriate size VHH-hinge-CH2-CH3 species were transcribed to generate DNA sequences, digested to identify the approximately 400 bp fragment comprising the nucleic acid sequence encoding the VHH domain was isolated. The isolated sequence was digested with restriction endonucleases to facilitate insertion into a phagemid vector for in frame with a sequence encoding a his-tag and transformed into E. coli to generate a phage library. Multiple rounds of biopanning of the phage library were conducted to identify VHHs that bound to the ECD of IL2Rg (human or mouse as appropriate). Individual phage clones were isolated for periplasmic extract ELISA (PE-ELISA) in a 96-well plate format and selective binding confirmed by colorimetric determination. The IL2Rg binding molecules that demonstrated specific binding to the IL2Rg antigen were isolated and sequenced and sequences analyzed to identify VHH sequences, CDRs and identify unique VHH clonotypes. As used herein, the term "clonotypes" refers a collection of binding molecules that originate from the same B-cell progenitor cell, in particular collection of antigen binding molecules that belong to the same germline family, have the same CDR3 lengths, and have 70% or greater homology in CDR3 sequence. The VHH molecules demonstrating specific binding to the hIL2Rg ECD antigen (anti-human IL2Rg VHHs) and the CDRs isolated from such VHHs are provided in Table 1. The VHH molecules demonstrating specific binding to the mIL2Rg ECD antigen (anti-mouse IL2Rg VHHs) and the CDRs isolated from such VHHs are provided in Table 3. Nucleic acid sequences encoding the VHHs of Table 1 and 3 are provided in Tables 2 and 4 respectively.

To more fully characterize the binding properties and evaluate binding affinity of the VHH molecules generated in In As illustrated by the data presented in Tables 6, the hIL2Rg binding molecules generated in accordance with the teaching of present disclosure exhibit specific binding and provided a range of affinities to the extracellular domain of hIL2Rg.

In some instances, due to sequence or structural similarities between the extracellular domains of IL2Rg receptors from various mammalian species, immunization with an antigen derived from a IL2Rg of a first mammalian species (e.g., the hIL2Rg-ECD) may provide antibodies which specifically bind to IL2Rg receptors of one or more additional mammalian species. Such antibodies are termed "cross reactive." For example, immunization of a camelid with a human derived antigen (e.g., the hIL2Rg-ECD) may generate antibodies that are cross-reactive the murine and human receptors. Evaluation of cross-reactivity of antibody with respect to the receptors derived from other mammalian species may be readily determined by the skilled artisan, for example using the methods relating to evaluation of binding affinity and/or specific binding described elsewhere herein such as flow cytometry or SPR. Consequently, the use of the term "human IL2Rg VHH" or "hIL2Rg VHH" merely denotes that the species of the IL2Rg antigen used for immunization of the camelid from which the VHH was derived was the human IL2Rg (e.g., the IL2Rg, ECD, SEQ ID NO: 192 but should not be understood as limiting with respect to the specific binding affinity of the VHH for IL2Rg molecules of other mammalian species. Similarly, the use of the term "mouse IL2Rg VHH" or "mIL2Rg VHH" merely denotes that the species of the IL2Rg antigen used for immunization of the camelid from which the VHH was derived was the murine IL2Rg (e.g., the mIL2Rg ECD, SEQ ID NO:194) but should not be understood as limiting with respect to the specific binding affinity of the VHH for IL2Rg molecules of other mammalian species.

Modified Forms of Single Domain Antibodies

CDR Grafted sdAbs

In some embodiments, the IL2Rg binding sdAb of the present disclosure is a CDR grafted IL2Rg binding sdAb. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. In some embodiments, the present disclosure provides a IL2Rg binding molecule comprising a CDR grafted IL2Rg binding sdAb, said CDR-grafted IL2Rg binding sdAb comprising a set of CDRs1, 2, and 3 as shown in a row of the Table 1A above. In some embodiments, the present disclosure provides a IL2Rg binding molecule comprising a CDR grafted IL2Rg binding sdAb, said CDR-grafted IL2Rg binding sdAb comprising a set of CDRs1, 2, and 3 as shown in a row of the Table 1B above.

Chimeric and Humanized sdAbs

Any framework region can be used with the CDRs as described herein. In some embodiments, the IL2Rg binding sdAb is a chimeric sdAb, in which the CDRs are derived from one species (e.g., camel) and the framework and/or constant regions are derived from another species (e.g., human or mouse). In specific embodiments, the framework regions are human or humanized sequences. Thus, humanized IL2Rg binding sdAbs derived from hIL2Rg binding VHHs are considered within the scope of the present disclosure. The techniques for humanization of camelid single domain antibodies are well known in the art. See, e.g., Vincke, et al. (2009) *General Strategy to Humanize a Camelid Single-domain Antibody and Identification of a Universal Humanized Nanobody Scaffold* J. Biol. Chem. 284(5)3273-3284.

In some embodiments, a VHH described herein can be humanized to contain human framework regions. Examples of human germlines that could be used to create humanized VHHS include, but are not limited to, VH3-23 (e.g., UniProt ID: P01764), VH3-74 (e.g., UniProtID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

Elimination of N-Linked Glycosylation Sites

In some embodiments, it is possible that an amino acid sequence (particularly a CDR sequence) of the IL2Rg binding sdAb may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the N-linked glycosylation motif is disrupted by the incorporation of conservative amino acid substitution of the Asn (N) residue of the N-linked glycosylation. As procaryotic host cells do not provide the mechanism for glycosylation of recombinant proteins, when employing a procaryotic expression system to produce a recombinant IL2Rg binding sdAb the modification of the sequence to eliminate the N-linked glycosylation sites may be obviated.

IL2Rg Binding Molecules Comprising Additional Agents

In some embodiments, a IL2Rg binding molecule operably linked to one or more additional biologically active agents including but not limited to, therapeutic agents, chemically, optically, or radioactively active agents, including combinations thereof. The conjugation of at least one such biologically, chemically, optically, or radioactively active agent confer additional biological or chemical properties to IL2Rg binding sdAb, the combination providing a IL2Rg binding molecule possessing additional or alternative utilities.

For example, the additional agent may be a molecule selected from one or more of: immunomodulatory agents (e.g., immunogens); molecules that improve aqueous solubility (e.g., water soluble polymers and hydrophilic molecules such as sugars); carrier molecules that extend in vivo half-life (e.g., PEGylation, Fc fusions or acylation); generation of antibodies for use in detection assays (e.g., epitope tags), enhance ease of purification (e.g., chelating peptides such as poly-His tags); targeting domains that provide selective targeting IL2Rg binding molecule to a particular cell or tissue type; therapeutic agents (e.g., therapeutic agents including small molecule or polypeptide agents); agents that visibility to optical or electromagnetic sensors (e.g., radionucleotides or fluorescent agents). In some embodiments, the linker is a cleavable linker or a non-cleavable linker. The use of a cleavable linker in a IL2Rg binding molecule as contemplated herein facilitates the release of a therapeutic agent into the intracellular cytoplasm upon internalization of the IL2Rg binding molecule. A non-cleavable linker would allow release upon digestion of the IL2Rg binding molecule of or it could be used with an agent that does not require release from the antibody (e.g., an imaging agent).

In some embodiments, where the IL2Rg binding molecule comprises a IL2Rg binding sdAb in stable association with an additional agent joined via a linker. A linker is a covalent linkage between two elements of a IL2Rg binding molecule (e.g., a hIL2Rg binding VHH and PEG polymer). A linker can be a covalent bond, chemical linker or a peptide linker. Suitable linkers include "flexible linkers" which are generally of sufficient length to permit some movement between the IL2Rg binding sdAb and the linked agent(s). Examples of chemical linkers include aryl acetylene, ethylene glycol oligomers containing 2-10 monomer units, diamines, diacids, amino acids, or combinations thereof. In some embodiments, the linker is a peptide linker. Suitable peptide linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Suitable peptide linkers are known in the art, and include, for example, peptide linkers containing flexible amino acid residues such as glycine and serine. Examples of flexible linkers include glycine polymers $(G)_n$, glycine-serine polymers, glycine-alanine polymers, alanine-serine polymers, and other flexible linkers. Glycine and glycine-serine polymers are relatively unstructured, and therefore can serve as a neutral tether between components. Further examples of flexible linkers include glycine polymers $(G)_n$, glycine-alanine polymers, alanine-serine polymers, glycine-serine polymers. Glycine and glycine-serine polymers are relatively unstructured, and therefore may serve as a neutral tether between components. A multimer (e.g., 1, 2, 3, 4, 5, 6, 7, 8, 9, 10, 10-20, 20-30, or 30-50) of such linker sequences may be linked together to provide flexible linkers that may be used to conjugate a heterologous amino acid sequence to IL2Rg binding sdAbs disclosed herein. In some embodiments the linkers have the formula (GGGS)n (SEQ ID NO: 197), (GGGSG)n (SEQ ID NO: 198), or (GGSG)n (SEQ ID NO: 199), wherein n is an integer selected from 1, 2, 3, 4, 5, 6, 7, 8, 9 and 10.

Immunomodulatory Agents

In some embodiments, a IL2Rg binding molecule of the present disclosure comprises an immunomodulatory agent (immunoconjugates). Immunomodulatory agents that may conjugated to the hIL2Rg binding sdAb of the present disclosure include, but are not limited to, inactivated virus particles, inactivated bacterial toxins such as toxoid from diphtheria, tetanus, cholera, or leukotoxin molecules, inactivated bacteria and dendritic cells. Such immunoconjugates are useful in facilitating an immune response against the IL2Rg or cells expressing the IL2Rg.

Flag Tags

In one embodiment, the present disclosure provides a IL2Rg binding molecule operably linked to an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IL2Rg binding sdAb polypeptide further comprises a C-terminal c-myc epitope tag.

Chelating Peptides

In one embodiment, the present disclosure provides a IL2Rg binding molecule operably linked to one or more transition metal chelating polypeptide sequences. The incorporation of such a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present IL2Rg binding molecule are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present IL2Rg binding molecule are polypeptides comprising 3-6 contiguous histidine residues (SEQ ID NO: 200) such as a six-histidine $(His)_6$ (SEQ ID NO: 195) peptide and are frequently referred to in the art as "His-tags." In addition to providing a purification "handle" for the recombinant proteins or to facilitate immobilization on SPR sensor chips, such the conjugation of the hIL2Rg binding molecule to a chelating peptide facilitates the targeted delivery to IL2Rg expressing cells of transition metal ions as kinetically inert or kinetically labile complexes in substantial accordance with the teaching of Anderson, et al., (U.S. Pat. No. 5,439,829 issued Aug. 8, 1995 and Hale, J. E (1996) Analytical Biochemistry 231(1):46-49. The transition metal ion is a reporter molecule such as a fluorescent compound or radioactive agent, including as radiological imaging or therapeutic agents.

Carrier Molecules

In some embodiments the IL2Rg binding molecule operably linked to one or more carrier molecules. Carrier molecules are typically large, slowly metabolized macromolecules which provide for stabilization and/or extended duration of action in vivo to distinguish such molecules from conventional carrier molecules used in the preparation of pharmaceutical formulations as described below. Examples of in vivo carriers that may be incorporated into IL2Rg binding molecules, but are not limited to: proteins (including but not limited to human serum albumin); fatty acids (acylation); polysaccharides (including but not limited to (N- and O-linked) sugars, sepharose, agarose, cellulose, or cellulose); polypeptides amino acid copolymers, acylation, or polysialylation, an polyethylene glycol (PEG) polymers.

Water Soluble Polymers

In some embodiments, the IL2Rg binding sdAb is conjugated to one or more water-soluble polymers. Examples of water soluble polymers useful in the practice of the present IL2Rg binding molecule include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol, polysaccharides, poly-alpha-hydroxy acid, polyvinyl alcohol (PVA), polyphosphazene, polyoxazolines (POZ), poly (N-acryloylmorpholine), or a combination thereof.

Polyethylene Glycol

In one embodiment, the carrier molecule is a polyethylene glycol ("PEG") polymer. Conjugation of PEG polymers to proteins (PEGylation) is a well-established method for the extension of serum half-life of biological agents. The PEGylated polypeptide may be further referred to as monopegylated, dipegylated, tripegylated (and so forth) to denote a polypeptide comprising one, two, three (or more) PEG moieties attached to the polypeptide, respectively. In some embodiments, the PEG may be covalently attached directly to the sdAb (e.g., through a lysine side chain, sulfhydryl group of a cysteine or N-terminal amine) or optionally employ a linker between the PEG and the sdAb. In some embodiments, a IL2Rg binding molecule comprises more than one PEG molecules each of which is attached to a different amino acid residue. In some embodiments, the sdAb may be modified by the incorporation of non-natural amino acids with non-naturally occurring amino acid side chains to facilitate site specific PEGylation. In other embodiments, cysteine residues may be substituted at one or more positions within the sdAb to facilitate site-specific PEGylation via the cysteine sulfhydryl side chain.

In some instances, the IL2Rg binding molecules of the present disclosure possess an N-terminal glutamine ("1Q") residue. N-terminal glutamine residues have been observed to spontaneously cyclyize to form pyroglutamate (pE) at or near physiological conditions. (See e.g., Liu, et al (2011) J. Biol. Chem. 286(13): 11211-11217). In some embodiments, the formation of pyroglutamate complicates N-terminal PEG conjugation particularly when aldehyde chemistry is used for N-terminal PEGylation. Consequently, when PEGylating the IL2Rg binding molecules of the present disclosure, particularly when aldehyde chemistry is to be employed, the IL2Rg binding molecules possessing an amino acid at position 1 (e.g., 1Q) are substituted at position 1 with an alternative amino acid or are deleted at position 1 (e.g., des-1Q). In some embodiments, the IL2Rg binding molecules of the present disclosure comprise an amino acid substitution selected from the group Q1E and Q1D.

PEGs suitable for conjugation to a polypeptide sequence are generally soluble in water at room temperature, and have the general formula $$R(O-CH_2-CH_2)_nO-R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

A molecular weight of the PEG used in a IL2Rg binding molecule is not restricted to any particular range. The PEG component of a IL2Rg binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the IL2Rg binding molecule, the PEG is a 40 kD branched PEG comprising two 20 kD arms.

The present disclosure also contemplates a IL2Rg binding molecule comprising more than one PEG moiety wherein the PEGs have different sizes values, and thus the various different PEGs are present in specific ratios. For example, in the preparation of a PEGylated IL2Rg binding molecule, some compositions comprise a mixture of mono-, di-, tri-, and quadra-PEGylated sdAb conjugates. In some compositions, the percentage of mono-PEGylated species is 18-25%, the percentage of di-PEGylated species is 50-66%, the percentage of tri-pegylated species is 12-16%, and the percentage of quadra-pegylated species up to 5%. Such complex compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

The PEG can be bound to a IL2Rg binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the sdAb is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin, et al., PCT International Application No. PCT/US2018/045257 filed Aug. 3, 2018 and published Feb. 7, 2019 as International Publication Number WO 2019/028419A1.

The PEG moiety of the of a PEGylated IL2Rg binding molecule may be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

Fc Fusions

In some embodiments, the carrier molecule is a Fc molecule or a monomeric subunit thereof. In some embodiments, the dimeric Fc molecule may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g., an IL2Rg binding sdAb) on a first Fc monomer with a "knob" modification and a second polypeptide on the second Fe monomer possessing a "hole" modification to facilitate the expression of heterodimeric polypeptide conjugates.

Targeting Domains

In some embodiments, the IL2Rg binding molecule operably linked to a targeting domain to facilitate selective binding to particular cell type or tissue expressing a cell surface molecule that specifically binds to such targeting domain, optionally incorporating a linker between the IL2Rg binding sdAb sequence and the sequence of the targeting domain of the fusion protein. In some embodiments of the IL2Rg binding molecule, the IL2Rg binding molecule may be targeted to a particular cell type cell by incorporation of a targeting domain into the structure of the IL2Rg binding molecules. As used herein, the term targeting domain refers to a moiety that specifically binds to a molecule expressed on the surface of a target cell. The targeting domain may be any moiety that specifically binds to one or more cell surface molecules (e.g., T cell receptor) expressed on the surface of a target cell. In some embodiments, the target cell is a T cell. In some embodiments, the target cell is a IL2Rg+T cell.

In some embodiments, the targeting domain is a ligand for a receptor. In some embodiments, the targeting domain is a ligand for a receptor expressed on the surface of a T cell. In some embodiments, the ligand is a cytokine. In some embodiments, the cytokine includes but is not limited to the group consisting interleukins, interferons, and functional derivatives thereof. In some embodiments, the cytokine includes but is not limited to the group consisting IL2, IL3, IL4, IL7, IL9, IL12, IL15, IL18, IL21, IL22, IL23, IL27, IL28, 1L34, and modified versions or fragments thereof that bind to their cognate ligand expressed on the surface of a T-cell. In some embodiments, the cytokine includes but is not limited to the group consisting of interferon alpha, interferon a2b, interferon gamma, or interferon lambda and modified versions or fragments thereof that bind to their cognate ligand expressed on the surface of a T-cell.

In another aspect, the present disclosure provides a multivalent binding molecule, the multivalent binding molecule comprising: (a) a IL2Rg binding molecule and (b) a second binding molecule that specifically binds to the extracellular domain of a second cell surface molecule, wherein the IL2Rg binding molecule and second binding molecule are operably linked, optionally through a chemical or polypeptide linker. In some embodiments, the IL2Rg binding molecules of the present disclosure are useful in the preparation of the multivalent binding molecules described in Gonzalez, et al. PCT/US2018/021301 published as WO 2018/182935 A1 on Oct. 4, 2018. In some aspects, the second binding molecule specifically binds to the extracellular domain of: (i) a component of cytokine receptor that activates the JAK/STAT pathway in the cell; (ii) a receptor tyrosine kinase; or (iii) a TNFR superfamily member. In some embodiments, the second surface molecule is a tyrosine kinase selected from EGFR, ErbB2, ErbB3, ErbB4, InsR, IGF1R, InsRR, PDGFRα, PDGFRβ, CSF1R/Fms, cKit, Flt-3/Flk2, VEGFR1, VEGFR2, VEGFR3, FGFR1, FGFR2, FGFR3, FGFR4, PTK7/CCK4, TrkA, TrkB, TrkC, Ror1, Ror2, MuSK, Met, Ron, Axl, Mer, Tyro3, Tie1, Tie2, EphA1-8, EphA10, EphB1-4, EphB6, Ret, Ryk, DDR1, DDR2, Ros, LMR1, LMR2, LMR3, ALK, LTK, SuRTK106/STYK1. In some embodiments, the second surface molecule is a TNFR superfamily member is selected from TNFR1 (TNFRSF1A), TNFR2 (TNFRSF1B; TNFRSF2), 41-BB (TNFRSF9); AITR (TNFRSF18); BCMA (TNFRSF17), CD27 (TNFRSF7), CD30 (TNFRSF8), CD40 (TNFRSF5), Death Receptor 1 (TNFRSF10C), Death Receptor-3 (TNFRSF25), Death Receptor 4 (TNFRSF10A), Death Receptor 5 (TNFRSF10B), Death Receptor-6 (TNFRSF21), Decoy Receptor-3 (TNFRSF6B), Decoy Receptor 2 (TNFRSF10D), EDAR, Fas (TNFRSF6), HVEM (TNFRSF14), LTBR (TNFRSF3), OX40 (TNFRSF4), RANK (TNFRSF11A), TACI (TNFRSF13B), Troy (TNFRSF19), XEDAR (TNFRSF27), Osteoprotegerin (TNFRSF11B), TWEAK receptor (TNFRSF12A), BAFF Receptor (TNFRSF13C), NGF receptor (TNFRSF16).

In some embodiments, the targeting domain is a polypeptide that specifically binds to a cell surface molecule associated with a tumor cell (e.g., a cognate ligand for a tumor cell receptor) selected from the group consisting of GD2, BCMA, CD19, CD33, CD38, CD70, GD2, IL3Ra2, CD19, mesothelin, Her2, EpCam, Muc1, ROR1, CD133, CEA, EGRFRVIII, PSCA, GPC3, Pan-ErbB and FAP.

In some embodiments, the targeting domain of the IL2Rg binding molecule is an antibody (as defined hereinabove to include molecules such as VHHs, scFvs, etc.) Examples of antibodies that may incorporated as a targeting domain of a IL2Rg binding molecule include but are not limited to the group consisting of: anti-GD2 antibodies, anti-BCMA antibodies, anti-CD19 antibodies, anti-CD33 antibodies, anti-CD38 antibodies, anti-CD70 antibodies, anti-GD2 antibodies and IL3Ra2 antibodies, anti-CD19 antibodies, anti-mesothelin antibodies, anti-Her2 antibodies, anti-EpCam antibodies, anti-Muc1 antibodies, anti-ROR1 antibodies, anti-CD133 antibodies, anti-CEA antibodies, anti-PSMA antibodies, anti-EGRFRVIII antibodies, anti-PSCA antibodies, anti-GPC3 antibodies, anti-Pan-ErbB antibodies, and anti-FAP antibodies.

The antibody or antigen-binding fragment thereof can also be linked to another antibody to form, e.g., a bispecific or a multispecific antibody Labels In some embodiments, IL2Rg binding molecules of the present disclosure comprise a label. In some embodiments, the label is incorporated to facilitate use as imaging agent, diagnostic agent, or for use in cell sorting procedures. The term labels includes but is not limited to fluorescent labels, a biologically active enzyme labels, a radioisotopes (e.g., a radioactive ions), a nuclear magnetic resonance active labels, a luminescent labels, or a magnetic compound. In one embodiment a IL2Rg binding sdAb (e.g., a IL2Rg binding VHH) molecule in stable association (e.g., covalent, coordinate covalent) with an imaging labels. The term imaging labels is used to describe any of a variety of compounds a signature that facilitates identification, tracing and/or localization of the IL2Rg binding sdAb (or its metabolites) using diagnostic procedures. Examples of imaging labels include, but are not limited to, fluorescent compounds, radioactive compounds, and compounds opaque to imaging methods (e.g., X-ray, ultrasound). Examples of radioactive compounds useful as imaging label include but are not limited to Technetium-99m ($^{99m}$Tc), Indium-111 ($^{111}$In), Iodine-131 ($^{131}$I), Iodine-123 ($^{123}$I), Iodine-125 ($^{125}$I), Gallium-67 ($^{67}$Ga), and Lutetium-177 ($^{177}$Lu), phosphorus ($^{32}$P), carbon ($^{14}$C), tritium ($^{3}$H), yttrium ($^{90}$Y), actinium ($^{225}$Ac), astatine ($^{211}$At), rhenium ($^{186}$Re), bismuth ($^{212}$Bi or $^{213}$Bi), and rhodium ($^{188}$Rh)

Therapeutic Agents

In some embodiments, IL2Rg binding molecules of the present disclosure comprise a therapeutic agent. Examples of therapeutic agents include therapeutic small molecule (e.g., chemotherapeutic agents) or biologic therapeutic agents including antibodies, cytoxic or cytostatic compounds, a radioisotope, molecules of plant, fungal, or bacterial origin, or biological proteins (e.g., protein toxins) or particles (e.g., nano-particles or recombinant viral particles, e.g., via a viral coat protein), therapeutic antibodies, chemotherapeutic agents, as described more fully herein.

In some embodiments, the therapeutic agent which may be incorporated into the IL2Rg binding molecules of the present disclosure is short-range radiation emitters, including, for example, short-range, high-energy a-emitters. Examples of such radioisotope include an alpha-emitter, a beta-emitter, a gamma-emitter or a beta/gamma emitter. Radioisotopes useful as therapeutic agents include yttrium 90 ($^{90}$Y), lutetium-177 ($^{177}$Lu), actinium-225 ($^{225}$Ac), astatine-211 ($^{211}$At), rhenium-186 ($^{186}$Re), bismuth-212 ($^{212}$Bi), bismuth-213 ($^{213}$Bi), and rhodium-188 ($^{188}$R).

In some embodiments, the IL2Rg binding molecules comprises a cytotoxic agent (or derivative thereof), such maytansinol or the DM1 maytansinoid), a taxane, or a calicheamicin, *pseudomonas* exotoxin A, deBouganin, ricin toxin, diphtheria toxin, an amatoxin, such as a-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

Synthesis of IL2Rg Binding Molecules:

In some embodiments, the IL2Rg binding molecules of the present disclosure are polypeptides. However, in some embodiments, only a portion of the IL2Rg binding molecule is a polypeptide, for example where the IL2Rg binding molecule comprises a non-peptidyl domain (e.g., a PEG IL2Rg binding sdAb conjugate, a radionucleotide IL2Rg binding sdAb conjugate, or a small molecule IL2Rg binding sdAb conjugate). The following provides guidance to enable the solid phase and recombinant synthesis of the polypeptide portions (domains) of IL2Rg binding molecules of the present disclosure. In those embodiments where only a portion of the IL2Rg binding molecule is a polypeptide, it will be understood that the peptidyl domain(s) of the IL2Rg binding molecule are an intermediate in the process which may undergo further processing to complete the synthesis of the desired IL2Rg binding molecules. The polypeptide domains of IL2Rg binding molecules may be produced by conventional methodology for the construction of polypeptides including recombinant or solid phase syntheses as described in more detail below.

Chemical Synthesis

In addition to generating mutant polypeptides via expression of nucleic acid molecules that have been altered by recombinant molecular biological techniques, polypeptide domains of IL2Rg binding molecules can be chemically synthesized. Chemically synthesized polypeptides are routinely generated by those of skill in the art. Chemical synthesis includes direct synthesis of a peptide by chemical means of the polypeptide domains of IL2Rg binding molecules exhibiting the properties described. This method can incorporate both natural and unnatural amino acids at desired positions that facilitate linkage of particular molecules (e.g., PEG).

In some embodiments, the polypeptide domains of IL2Rg binding molecules of the present disclosure may be prepared by chemical synthesis. The chemical synthesis of the polypeptide domains of IL2Rg binding molecules may proceed via liquid-phase or solid-phase. Solid-phase peptide synthesis (SPPS) allows the incorporation of unnatural amino acids and/or peptide/protein backbone modification. Various forms of SPPS are available for synthesizing the polypeptide domains of IL2Rg binding molecules of the present disclosure are known in the art (e.g., Ganesan A. (2006) Mini Rev. Med. Chem. 6:3-10; and Camarero J. A. et al., (2005) Protein Pept Lett. 12:723-8). In the course of chemical synthesis, the alpha functions and any reactive side chains may protected with acid-labile or base-labile groups that are stable under the conditions for linking amide bonds but can readily be cleaved without impairing the peptide chain that has formed.

In the solid phase synthesis, either the N-terminal or C-terminal amino acid may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the peptide is cleaved from the support material while simultaneously cleaving the side chain protecting groups. The peptide obtained can be purified by various chromatographic methods including but not limited to hydrophobic adsorption chromatography, ion exchange chromatography, distribution chromatography, high pressure liquid chromatography (HPLC) and reversed-phase HPLC.

Recombinant Production

Alternatively, polypeptide domains of IL2Rg binding molecules of the present disclosure may be produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation.

Synthesis of Nucleic Acid Sequences Encoding the IL2Rg Binding Molecule

In some embodiments, the polypeptide domains of IL2Rg binding molecules produced by recombinant methods using a nucleic acid sequence encoding the polypeptide domains of IL2Rg binding molecule (or fusion protein comprising the polypeptide domains of IL2Rg binding molecule). The nucleic acid sequence encoding the desired polypeptide domains of IL2Rg binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of the polypeptide domains of IL2Rg binding molecule) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the polypeptide domains of IL2Rg binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the polypeptide domains of the IL2Rg binding molecule may be obtained from various commercial sources that provide custom synthesis of nucleic acid sequences. Amino acid sequence variants of the HUMAN IL2Rg binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion can be made to arrive at the final construct, provided that the final construct possesses the desired biological activity as defined herein.

Methods for constructing a DNA sequence encoding the polypeptide domains of IL2Rg binding molecule and expressing those sequences in a suitably transformed host include, but are not limited to, using a PCR-assisted mutagenesis technique. Mutations that consist of deletions or additions of amino acid residues to polypeptide domains of IL2Rg binding molecule can also be made with standard recombinant techniques. In the event of a deletion or addition, the nucleic acid molecule encoding polypeptide domains of IL2Rg binding molecules optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A polypeptide domain of IL2Rg binding molecules of the present disclosure may be produced recombinantly not only directly, but also as a fusion polypeptide with a heterologous polypeptide, e.g., a signal sequence or other polypeptide having a specific cleavage site at the N-terminus or C-terminus of the mature IL2Rg binding molecule. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the IL2Rg binding molecule (i.e. the hIL2Rg or mIL2Rg signal sequence). The inclusion of a signal sequence depends on whether it is desired to secrete the IL2Rg binding molecule from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type IL-2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as *Saccharomyces cerevisiae*, the alpha mating factor secretion signal sequence may be employed to achieve extracellular secretion of the IL2Rg binding molecule into the culture medium as described in Singh, U.S. Pat. No. 7,198,919 B1.

In the event the polypeptide domain of IL2Rg binding molecules to be expressed is to be expressed as a chimera (e.g., a fusion protein comprising a IL2Rg binding molecule and a heterologous polypeptide sequence), the chimeric protein can be encoded by a hybrid nucleic acid molecule comprising a first sequence that encodes all or part of the polypeptide domains of IL2Rg binding molecule and a second sequence that encodes all or part of the heterologous polypeptide. For example, polypeptide domains of IL2Rg binding molecules described herein may be fused to a hexa-histidine tag (SEQ ID NO: 195) to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the polypeptide domains of IL2Rg binding molecule. For example, the N-terminus may be linked to a targeting domain and the C-terminus linked to a hexa-histidine tag (SEQ ID NO: 195) purification handle.

The complete amino acid sequence of the polypeptide domain of IL2Rg binding molecule (or fusion/chimera) to be expressed can be used to construct a back-translated gene. A DNA oligomer containing a nucleotide sequence coding for the polypeptide domain of IL2Rg binding molecules can be synthesized. For example, several small oligonucleotides coding for portions of the desired polypeptide can be synthesized and then ligated. The individual oligonucleotides typically contain 5' or 3' overhangs for complementary assembly.

In some embodiments, the nucleic acid sequence encoding the polypeptide domain of the IL2Rg binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g., Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

In some embodiments, the nucleic acid sequence encoding the polypeptide domain of the IL2Rg binding molecule is a DNA sequence provided in Table 2. In some embodiments, the nucleic acid sequence encoding the polypeptide domain of the IL2Rg binding molecule is a DNA sequence provided in Table 4.

Expression Vectors

Once assembled (by synthesis, site-directed mutagenesis or another method), the nucleic acid sequence encoding polypeptide domains of IL2Rg binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors. To facilitate efficient expression of the recombinant polypeptide, the nucleic acid sequence encoding the polypeptide sequence to be expressed is operably linked to transcriptional and translational regulatory control sequences that are functional in the chosen expression host.

Expression vectors typically contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors for polypeptide domain of IL2Rg binding molecules of the present disclosure contain a regulatory sequence that is recognized by the host organism and is operably linked to nucleic acid sequence encoding the polypeptide domains of IL2Rg binding molecule. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject IL2Rg binding molecule, particularly as regards potential secondary structures.

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context. Proper assembly of the expression vector can be confirmed by nucleotide sequencing, restriction mapping, and expression of a biologically active polypeptide in a suitable host.

Host Cells

The present disclosure further provides prokaryotic or eukaryotic cells that contain and express a nucleic acid molecule that encodes a polypeptide domains of IL2Rg binding molecule. A cell of the present disclosure is a transfected cell, i.e., a cell into which a nucleic acid molecule, for example a nucleic acid molecule encoding a polypeptide domains of IL2Rg binding molecule, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this IL2Rg binding molecule, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant polypeptide domains of IL2Rg binding molecule or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerevisiae* include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The polypeptide domains of IL2Rg binding molecule can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, the recombinant polypeptide domains of IL2Rg binding molecule may be glycosylated or unglycosylated depending on the host organism used to produce the IL2Rg binding molecule. If bacteria are chosen as the host then the polypeptide domains of IL2Rg binding molecule produced will be aglycosylated. Eukaryotic cells, on the other hand, will glycosylate the recombinant polypeptide domains of IL2Rg binding molecule.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection

The expression constructs of the can be introduced into host cells to thereby produce the recombinant polypeptide domains of IL2Rg binding molecule disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins

Recombinantly-produced IL2Rg binding polypeptides can be recovered from the culture medium as a secreted polypeptide if a secretion leader sequence is employed. Alternatively, the IL2Rg binding polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification

Various purification steps are known in the art and find use, e.g., affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g., gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The recombinant polypeptide domains of IL2Rg binding molecule produced by the transformed host can be purified according to any suitable method. IL2Rg binding molecules can be isolated from inclusion bodies generated in *E. coli*, or from conditioned medium from either mammalian or yeast cultures producing a given IL2Rg binding molecule sing cation exchange, gel filtration, and or reverse phase liquid chromatography.

The substantially purified forms of the recombinant polypeptides can be used, e.g., as therapeutic agents, as described herein.

The biological activity of the recombinant polypeptide domains of IL2Rg binding molecule produced in accordance with the foregoing can be confirmed by a IL2Rg binding using procedures well known in the art including but not limited to competition ELISA, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493:323-343 (2009) with instrumentation commercially available from GE Healthcare Bio-Sciences such as the Biacore 8+, Biacore S200, Biacore T200 (GE Healthcare Bio-Sciences, 100 Results Way, Marlborough MA 01752)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

Methods of Use

Use of CD132 Binding Molecules as Inhibitors of IL2 Function

As previously discussed, CD132 is a receptor subunit shared among the "common-gamma chain" family of cytokine receptors including IL2, IL-4, IL-7, IL-9, IL-15, and IL21. As such, the molecules of the present disclosure are useful as general inhibitors of the common gamma chain family of cytokines and provide therapeutic utility as immunosuppressive agents in the treatment of disease states caused by unwanted immune response such as graft-versus-host disease. The use of monoclonal antibodies against CD132 as inhibitors of the common gamma chain family of cytokines are known in the literature and are disclosed as useful in the treatment of chronic graft versus host disease, liver and lung fibrosis and pulmonary dysfunction. See, e.g. Hechinger, et al (2015) Blood 125(3):570-580.

As previously discussed, it is well established that IL2 has significant beneficial effects, particularly in the treatment of cancers and enhancing the immune response. However, as previously noted, HD-IL2 therapy is associated with significant toxicity. Consequently, in some instances in combination with the administration of an IL2 agonist, in particular extended-release forms of IL2 such Fc fusions and PEGylated versions of IL2, in the event of excess IL2 toxicity, the administration of an IL2 inhibitor may mitigate the toxic effects of IL2 function. In some embodiments, the compositions of the present disclosure are useful as competitive inhibitors of IL2 agonists and find utility in the mitigation of IL2 related toxicities.

In some embodiments, compositions comprising IL2Rg binding molecules are useful in the treatment of a human diseases including autoimmune and inflammatory diseases, infectious diseases and neoplastic diseases. In one embodiment, the present disclosure provides a method of modulating the activity of cells expressing the IL2Rg by the administration of a IL2Rg binding molecule to a subject in an amount sufficient to interfere with the activity of receptors comprising the of IL2Rg. The present disclosure further provides a method of modulating the activity of cells expressing the IL2Rg in a mixed population of cells comprising contacting said population of cells, in vivo and/or ex vivo, with a IL2Rg binding molecule or complex of the present disclosure to in an amount sufficient to interfere with the activity of receptors comprising the IL2Rg. In some embodiments, the IL2Rg binding molecules of the present disclosure are inhibitors of the activity of receptors of which IL2Rg forms a subunit (e.g., the high and intermediate affinity IL2 receptors).

In another embodiment, the compositions of the present disclosure are useful as CD132 inhibitors in the restoration of immunological tolerance in autoimmune disease. Yuan, et al (JCI Insight (2018) 3(2):e96600) describe the use of CD132 binding molecules for the selective ablation of pathogenic NK cells and memory phenotype CD8+ T cells from pancreatic islets; the suppression of IFN-γ production in islet immune cells and inhibition of the conversion of islet Th17 cells into diabetogenic Th1 cells and thus are useful in the treatment of type-1 diabetes. Yuan, et al further describe the use of CD132 inhibitors in combination with IL-33 in the ablation of pathogenic cells and promotion of Treg abundancy and function.

Use of CD132 Binding Molecules as Targeting Domains for IL2 Ligands

In some embodiments the compositions of the present disclosure may be conjugated to therapeutic agents for the targeted delivery of such therapeutic agent to T cells expressing the CD132 receptor. In one embodiment, the therapeutic agent is an IL2 species such as wild-type human IL2, IL2 muteins, including IL2 agonist muteins and IL2 antagonist muteins.

Inhibition of IL2 Receptor Activity

In one embodiment, the present disclosure provides a method of modulating the activity of the IL2 receptor on cells expressing the IL2R by the administration of a IL2Rg binding molecule to a subject in an amount sufficient to interfere with the activity of the IL2 receptor. The present disclosure further provides a method of modulating the activity of cells expressing the IL2Rg in a mixed population of cells comprising contacting said population of cells, in vivo and/or ex vivo, with a IL2Rg binding molecule or complex of the present disclosure to in an amount sufficient to interfere with the activity of receptors comprising the IL2Rg.

Autoimmune and Inflammatory Diseases

In some embodiments, compositions comprising IL2Rg binding molecules are useful in the treatment of a human diseases including autoimmune and inflammatory diseases, infectious diseases and neoplastic diseases. In one embodiment, the present disclosure provides a method of modulating the activity of cells expressing the IL2Rg by the administration of a IL2Rg binding molecule to a subject in an amount sufficient to interfere with the activity of receptors comprising the of IL2Rg. The present disclosure further provides a method of modulating the activity of cells expressing the IL2Rg in a mixed population of cells comprising contacting said population of cells, in vivo and/or ex vivo, with a IL2Rg binding molecule or complex of the present disclosure to in an amount sufficient to interfere with the activity of receptors comprising the IL2Rg. In some embodiments, the IL2Rg binding molecules of the present disclosure are inhibitors of the activity of receptors of which IL2Rg forms a subunit (e.g., the high and intermediate affinity IL2 receptors).

In one embodiment the present disclosure provides a method of treating a T cell mediated autoimmune disease, the method comprising the administration of a IL2Rg binding molecule to a subject in an amount effective to inhibit a T-cell mediated immune response. IL2Rg binding molecules of the present disclosure specifically bind to the ECD of the IL2Rg, either alone or associated with other molecules, and are useful in modulating the function of the cells expressing the IL2Rg isoform and are useful in the treatment or prevention of diseases, disorders or conditions associated with inflammation or autoimmunity where immunological memory is involved in the cause, maintenance or exacerbation of the disease, disorder or condition.

Diseases amenable to treatment with an IL2Rg binding molecule (including pharmaceutically acceptable formulations comprising an IL2Rg binding molecules and/or the nucleic acid molecules that encode them including recombinant viruses encoding such an IL2Rg binding molecules) of the present disclosure include inflammatory or autoimmune diseases including but not limited to, organ rejection, graft versus host disease, autoimmune thyroid disease, multiple sclerosis, allergy, asthma, neurodegenerative diseases including Alzheimer's disease, systemic lupus erythramatosis (SLE), autoinflammatory diseases, inflammatory bowel disease (IBD), Crohn's disease, diabetes including Type 1 or type 2 diabetes, inflammation, autoimmune disease, atopic diseases, paraneoplastic autoimmune diseases, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity Enthesopathy Arthropathy Syndrome), juvenile dennatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter's syndrome, SEA Syndrome (Seronegativity, Enthesopathy, Arthropathy Syndrome).

Other examples of proliferative and/or differentiative disorders amenable to treatment with IL2Rg binding molecules (including pharmaceutically acceptable formulations comprising IL2Rg binding molecules and/or the nucleic acid molecules that encode them including recombinant viruses encoding such IL2Rg binding molecules) of the present disclosure include, but are not limited to, skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of inflammatory or autoimmune skin disorders include psoriasis, psoriatic arthritis, dermatitis (eczema), for example, exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

The compositions of the present disclosure (including pharmaceutically acceptable formulations comprising IL2Rg binding molecules and/or the nucleic acid molecules that encode them including recombinant viruses encoding such IL2Rg binding molecules) can also be administered to a patient who is suffering from (or may suffer from) psoriasis or psoriatic disorders. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidennal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, plaque psoriasis, moderate to severe plaque psoriasis, psoriasis vulgaris, eruptive psoriasis, psoriatic erythroderma, generalized pustular psoriasis, annular pustular psoriasis, or localized pustular psoriasis.

Combination with Supplementary Therapeutic Agents

The present disclosure provides for the use of the IL2Rg binding molecules of the present disclosure in combination with one or more additional active agents ("supplementary agents"). Such further combinations are referred to interchangeably as "supplementary combinations" or "supplementary combination therapy" and those therapeutic agents that are used in combination with IL2Rg binding molecules of the present disclosure are referred to as "supplementary agents." As used herein, the term "supplementary agents" includes agents that can be administered or introduced separately, for example, formulated separately for separate administration (e.g., as may be provided in a kit) and/or therapies that can be administered or introduced in combination with the IL2Rg binding molecules.

As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g., IL2Rg binding molecule) is considered to be administered in combination with a second agent (e.g., a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g., nivolumab or pembrolizumab) are typically administered by IV infusion every two weeks or every three weeks while the IL2Rg binding molecules of the present disclosure are typically administered more frequently, e.g., daily, BID, or weekly. However, the administration of the first agent (e.g., pembrolizumab) provides a therapeutic effect over an extended time and the administration of the second agent (e.g., an IL2Rg binding molecule) provides its therapeutic effect while the therapeutic effect of the first agent remains ongoing such that the second agent is considered to be administered in combination with the first agent, even though the first agent may have been administered at a point in time significantly distant (e.g., days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the IL2Rg binding molecule and the supplementary agent(s) are administered or applied sequentially, e.g., where one agent is administered prior to one or more other agents. In other embodiments, the IL2Rg binding molecule and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Supplemental Agents Useful in the Treatment of Inflammatory or Autoimmune Disorders In some embodiments, the method further comprises administering of the IL2Rg binding molecule of the present disclosure in combination with one or more supplementary agents selected from the group consisting of a corticosteroid, a Janus kinase inhibitor, a calcineurin inhibitor, a mTor inhibitor, an IMDH inhibitor, a biologic, a vaccine, and a therapeutic antibody. In certain embodiments, the therapeutic antibody is an antibody that binds a protein selected from the group consisting of BLyS, CD11a, CD20, CD25, CD3, CD52, IgE, IL12/IL23, IL17a, IL1$\beta$, IL4R$\alpha$, IL5, IL6R, integrin-$\alpha4\beta7$, RANKL, TNF$\alpha$, VEGF-A, and VLA-4.

In some embodiments, the supplementary agent is one or more agents selected from the group consisting of corticosteroids (including but not limited to prednisone, budesonide, prednilisone), Janus kinase inhibitors (including but not limited to tofacitinib (Xeljanz®), calcineurin inhibitors (including but not limited to cyclosporine and tacrolimus), mTor inhibitors (including but not limited to sirolimus and everolimus), IMDH inhibitors (including but not limited to azathioprine, leflunomide and mycophenolate), biologics such as abatcept (Orencia®) or etanercept (Enbrel®), and therapeutic antibodies.

Examples of therapeutic antibodies that may be administered as supplementary agents in combination with the IL2Rg binding molecules of the present disclosure in the treatment of autoimmune disease include but are not limited to anti-CD25 antibodies (e.g. daclizumab and basiliximab), anti-VLA-4 antibodies (e.g. natalizumab), anti-CD52 antibodies (e.g. alemtuzumab), anti-CD20 antibodies (e.g. rituximab, ocrelizumab), anti-TNF antibodies (e.g. infliximab, and adalimumab), anti-IL6R antibodies (e.g. tocilizumab), anti-TNF$\alpha$ antibodies (e.g. adalimumab (Humira®), golimumab, and infliximab), anti-integrin-$\alpha4\beta7$ antibodies (e.g. vedolizumab), anti-IL17a antibodies (e.g. brodalumab or secukinumab), anti-IL4Ra antibodies (e.g. dupilumab), anti-RANKL antibodies, IL6R antibodies, anti-IL18 antibodies (e.g. canakinumab), anti-CD11a antibodies (e.g. efalizumab), anti-CD3 antibodies (e.g. muramonab), anti-IL5 antibodies (e.g. mepolizumab, reslizumab), anti-BLyS antibodies (e.g. belimumab); and anti-IL12/IL23 antibodies (e.g ustekinumab).

Many therapeutic antibodies have been approved for clinical use against autoimmune disease. Examples of antibodies approved by the United States Food and Drug Administration (FDA) for use in the treatment of autoimmune diseases in a subject suffering therefrom that may be administered as supplementary agents in combination with the IL2Rg binding molecules of the present disclosure (and optionally additional supplementary agents) for the treatment of the indicated autoimmune disease are provided in Table 7 below:

TABLE 7

Antibodies Useful as Supplmentary Agents In the Treatment of Autoimmune and Inflammatory Disease

| Name | Target | Therapeutic Indication |
|---|---|---|
| efalizumab | CD11a | Psoriasis |
| belimumab | BLyS | Systemic lupus erythematosus |
| ocrelizumab | CD20 | Multiple sclerosis |
| rituximab | CD20 | Multiple sclerosis |
| basiliximab | CD25 | Transplantation rejection |
| daclizumab | CD25 | Transplantation rejection |
| muromonab | CD3 | Transplantation rejection |
| alemtuzumab | CD52 | Multiple sclerosis |
| omalizumab | IgE | Asthma |
| ustekinumab | IL12/IL23 | Plaque psoriasis |
| brodalumab | IL17a | Psoriasis, psoriatic arthritis, ankylosing spondylitis |
| secukinumab | IL17a | Psoriasis, psoriatic arthritis, ankylosing spondylitis |
| ixekizumab | IL17a | Psoriasis, psoriatic arthritis, ankylosing spondylitis |
| canakinumab | IL1$\beta$ | Cryopyrin-associated periodic syndrome, tumor necrosis factor receptor associated periodic syndrome, hyperimmunoglobulin D syndrome, mevalonate kinase deficiency, familial Mediterranean fever, rheumatoid arthritis |
| dupilumab | IL4R$\alpha$ | Asthma, dermatitis |
| mepolizumab | IL5 | Asthma |
| reslizumab | IL5 | Asthma |
| tocilizumab | IL6R | Rheumatoid arthritis |
| vedolizumab | Integrin-$\alpha4\beta7$ | Ulcerative colitis, Crohn's disease |
| denosumab | RANKL | Osteoporosis |
| certolizumab | TNFa | Chron's disease, rheumatoid arthritis |
| golimumab | TNFa | Rheumatoid arthritis, psoriatic arthritis, ankylosing spondylitis |

TABLE 7-continued

Antibodies Useful as Supplmentary Agents In the
Treatment of Autoimmune and Inflammatory Disease

| Name | Target | Therapeutic Indication |
| --- | --- | --- |
| adalimumab | TNFα | Rheumatoid arthritis, juvenile idiopathic arthritis, psoriatic arthritis, ankylosing spondylitis, Crohn's disease, plaque psoriasis |
| infliximab | TNFα | Crohn's disease, ulcerative colitis, rheumatoid arthritis, ankylosing spondylitis, psoriatic arthritis, plaque psoriasis |
| ranibizumab | VEGF-A | Neovascular age-related macular degeneration, macular edema |
| natalizumab | VLA-4 | Multiple sclerosis, relapsing rultiple sclerosis, Crohn's disease |

The foregoing antibodies of Table 7 useful as supplementary agents in the practice of the methods of the present disclosure may be administered alone or in the form of any antibody drug conjugate (ADC) comprising the antibody, linker, and one or more drugs (e.g. 1, 2, 3, 4, 5, 6, 7, or 8 drugs) or in modified form (e.g. PEGylated).

Isolation, Enrichment or Depletion of IL2Rg+ Cells from a Biological Sample

In one embodiment, the present disclosure provides a method of use of the IL2Rg binding molecules of the present disclosure useful in a process for in the isolation, enrichment, or depletion of IL2Rg+ cells from a biological sample comprising IL2Rg+ cells. The biological sample may comprise cells of blood origin such as P1BMC, T cells, B cells of cell culture origin or of tissue origin such as brain or bone marrow. Processes suitable for the isolation, enrichment or depletion of IL2Rg+ cells comprise centrifugation, filtration, magnetic cell sorting and fluorescent cell sorting by techniques well known in the art. The present disclosure further provides a method for the treatment of a subject suffering from a disease, disorder or condition by the administration of a therapeutically effective amount of a cell product enriched or depleted of IL2Rg+ cells through the use of a IL2Rg binding molecule as described herein.

In one embodiment, the sorting procedure employs a IL2Rg binding molecule comprising a fluorescent label for use in FACS isolation or depletion of IL2Rg+ cells from a sample. The fluorescent label may be attached to the sdAb of the IL2Rg binding molecule directly (e.g., by chemical conjugation optionally employing a linker) or indirectly (e.g., by biotinylation of the sdAb and binding of the biotinylated antibody to a streptavidin fluorochrome conjugate). Such fluorescently labelled IL2Rg+ cells may be separated from a mixed cell population using conventional FACS technology.

In an alternative embodiment, the selection procedure employs IL2Rg binding molecules of the present disclosure (e.g., a IL2Rg binding VHH) conjugated to magnetic particles which provide magnetic labeling of the IL2Rg+ cells for use in magnetic cell separation procedures. In one embodiment the method comprises: (a) conjugation of one or more IL2Rg binding molecule of the present disclosure (e.g., a IL2Rg binding VHH) to a magnetic particle; (b) creating a mixture by contacting the biological sample with a quantity of the magnetic particles conjugated to IL2Rg binding molecule; (c) subjecting to a magnetic field such that the magnetically labelled IL2Rg+ cells are retained; (d) removing the non-magnetically labelled cells from the mixture; and (e) removal of the magnetic field enabling isolation of the IL2Rg+ cells.

The cell selection procedure (e.g., FACS or magnetic separation) results in two products: (a) a population of cells depleted of IL2Rg+ cells and (b) a population of cells enriched for IL2Rg+ cells. Each of these populations may be further processed by convention procedures to identify particular IL2Rg+ or IL2Rg– cell subsets which may be useful in research, diagnostic or clinical applications. For example, isolation of specific IL2Rg+ T cell subsets that also express one or more of CD4, CD8, CD19, CD25, and CD62L, further iterations of the using one or more antibodies that specifically bind to CD4, CD8, CD19, CD25, and CD62L antigens respectively by FACS or magnetic field separation by techniques well known in the art.

In one embodiment of the IL2Rg binding molecule a humanized antibody or fragment thereof as disclosed herein may be used for depletion of IL2Rg-expressing cells from a biological sample comprising IL2Rg-expressing cells such peripheral blood or lymphoid tissue which may optionally be further processed for further isolation of IL2Rg+ naïve T cell subsets, isolation human IL2Rg+ memory T cells from a population of CD4+ or CD8+ cells, or isolation of human IL2RgRA+ naïve T cells from presorted CD4+ or CD8+ cells by depletion of IL2Rg+ cells. In one embodiment, the IL2Rg binding molecule provides a method of generating a population of cells enriched for naïve Tregs from a biological sample, the method comprising depleting IL2Rg+ cells using a IL2Rg binding molecule of the present disclosure as described above, optionally further comprising the steps of depleting CD8+ and/or CD19+ cells. The IL2Rg+ depleted cell population may optionally be further expanded in vitro for particular cell types to in the preparation of a cell product comprising a therapeutically effective amount of the IL2Rg+ depleted cell product which may be administered to a subject suffering from a disease, disorder or condition.

The IL2Rg+ enriched cell population may optionally be further expanded in vitro to in the preparation of a cell product comprising a therapeutically effective amount of the IL2Rg+

Formulations

The present disclosure further provides pharmaceutically acceptable formulations of the IL2Rg binding molecules of the present disclosure. The preferred formulation depends on the intended mode of administration and therapeutic application. Pharmaceutical dosage forms of the IL2Rg binding molecules described herein comprise physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of polypeptides include polysaccharides such as sodium carboxymethylcellulose or methylcellulose, polyvinylpyrrolidone, polyacrylates, polyoxyethylene-polyoxypropylene-block polymers, PEG, polymeric amino acids, amino acid copolymers, and lipid aggregates (such as oil droplets or liposomes).

The pharmaceutical compositions may also comprise pharmaceutically acceptable, non-toxic carriers, excipients, stabilizers, or diluents, which are defined as vehicles commonly used to formulate pharmaceutical compositions for animal or human administration. The diluent is selected so as not to affect the biological activity of the combination. Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Formulations to be used for in vivo administration are typically sterile. Sterilization of the compositions of the present disclosure may readily accomplished by filtration through sterile filtration membranes.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (Langer, Science 249: 1527, 1990 and Hanes, Advanced Drug Delivery Reviews 28: 97-119, 1997). The agents of this disclosure can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Vector Delivery of Polypeptide IL2Rg Binding Molecules

In those embodiments where the IL2Rg binding molecule is a polypeptide, such IL2Rg binding molecules may also be delivered to a subject through the administration of a recombinant vectors comprising a nucleic acid sequence encoding the peptidyl IL2Rg binding molecule operably linked to an expression control sequence in the cells of the tissues of the subject.

Expression vectors may be viral vectors or non-viral vectors. The term "nonviral vector" refers to an autonomously replicating, extrachromosomal circular DNA molecule, distinct from the normal genome and nonessential for cell survival under nonselective conditions capable of effecting the expression of an coding sequence in the target cell. Plasmids are examples of non-viral vectors. In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, magnetic fields (electroporation)

In one embodiment, a non-viral vector may be provided in a non-viral delivery system. Non-viral delivery systems are typically complexes to facilitate transduction of the target cell with a nucleic acid cargo wherein the nucleic acid is complexed with agents such as cationic lipids (DOTAP, DOTMA), surfactants, biologicals (gelatin, chitosan), metals (gold, magnetic iron) and synthetic polymers (PLG, PEI, PAMAM). Numerous embodiments of non-viral delivery systems are well known in the art including lipidic vector systems (Lee et al. (1997) Crit Rev Ther Drug Carrier Syst. 14:173-206); polymer coated liposomes (Marin et al., U.S. Pat. No. 5,213,804, issued May 25, 1993; Woodle, et al., U.S. Pat. No. 5,013,556, issued May 7, 1991); cationic liposomes (Epand et al., U.S. Pat. No. 5,283,185, issued Feb. 1, 1994; Jessee, J. A., U.S. Pat. No. 5,578,475, issued Nov. 26, 1996; Rose et al, U.S. Pat. No. 5,279,833, issued Jan. 18, 1994; Gebeyehu et al., U.S. Pat. No. 5,334,761, issued Aug. 2, 1994).

In another embodiment, the expression vector may be a viral vector. As used herein, the term viral vector is used in its conventional sense to refer to any of the obligate intracellular parasites having no protein-synthesizing or energy-generating mechanism and generally refers to any of the enveloped or non-enveloped animal viruses commonly employed to deliver exogenous transgenes to mammalian cells. A viral vector may be replication competent (e.g., substantially wild-type), conditionally replicating (recombinantly engineered to replicate under certain conditions) or replication deficient (substantially incapable of replication in the absence of a cell line capable of complementing the deleted functions of the virus). The viral vector can possess certain modifications to make it "specifically replicating," i.e. that it replicates preferentially in certain cell types or phenotypic cell states, e.g., cancerous. Viral vector systems useful in the practice of the instant IL2Rg binding molecule include, for example, naturally occurring or recombinant viral vector systems. Examples of viruses useful in the practice of the present IL2Rg binding molecule include recombinantly modified enveloped or non-enveloped DNA and RNA viruses. For example, viral vectors can be derived from the genome of human or bovine adenoviruses, vaccinia virus, lentivirus, herpes virus, adeno-associated virus, human immunodeficiency virus, sindbis virus, and retroviruses (including but not limited to Rous sarcoma virus), and hepatitis B virus. Typically, genes of interest are inserted into such vectors to allow packaging of the gene construct, typically with accompanying viral genomic sequences, followed by infection of a sensitive host cell resulting in expression of the gene of interest (e.g., a targeting antigen).

The expression vector may encode one or more polypeptides in addition to the targeting antigen. When expressing multiple polypeptides as in the practice of the present IL2Rg binding molecule, each polypeptide may be operably linked to an expression control sequence (monocistronic) or multiple polypeptides may be encoded by a polycistronic construct where multiple polypeptides are expressed under the control of a single expression control sequence. In one embodiment, the expression vector encoding the targeting antigen may optionally further encode one or more immunological modulators. Examples of immunological modulators useful in the practice of the present IL2Rg binding molecule include but are not limited to cytokines. Examples of such cytokines are interleukins including but not limited to one more or of IL-1, IL-2, IL-3, IL-4, IL-12, TNF-alpha, interferon alpha, interferon alpha-2b, interferon-beta, interferon-gamma, GM-CSF, MIP1-alpha, MIP1-beta, MIP3-alpha, TGF-beta and other suitable cytokines capable of modulating immune response. The expressed cytokines can be directed for intracellular expression or expressed with a signal sequence for extracellular presentation or secretion.

The expression vector may optionally provide an additional expression cassette comprising a nucleic acid sequence encoding a "rescue" gene. A "rescue gene" is a nucleic acid sequence, the expression of which renders the cell susceptible to killing by external factors or causes a toxic condition in the cell such that the cell is killed. Providing a rescue gene enables selective cell killing of transduced cells. Thus, the rescue gene provides an additional safety precaution when said constructs are incorporated into the cells of a mammalian subject to prevent undesirable spreading of transduced cells or the effects of replication competent vector systems. In one embodiment, the rescue gene is the thymidine kinase (TK) gene (see e.g., Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir.

Dosage

The present disclosure further provides the administration of therapeutically or prophylactically effective dose of IL2Rg binding molecule or a recombinant vector or cell comprising a nucleic acid sequence encoding a polypeptide IL2Rg binding molecule to a subject suffering from or at risk of developing, respectively, a disease, disorder or condition. The dosage of the pharmaceutical composition comprising the IL2Rg binding molecules, vector or cell depends on factors including the route of administration, the disease to be treated, and physical characteristics, e.g., age, weight, general health, of the subject. Typically, the amount of a IL2Rg binding molecule contained within a single dose may be an amount that effectively prevents, delays, or treats the disease without inducing significant toxicity. A pharmaceutical composition of the disclosure may include a dosage of a IL2Rg binding molecule described herein ranging from 0.01 to 500 mg/kg (e.g., from 0.01 to 450 mg, from 0.01 to 400 mg, from 0.01 to 350 mg, from 0.01 to 300 mg, from 0.01 to 250 mg, from 0.01 to 200 mg, from 0.01 to 150 mg, from 0.01 to 100 mg, from 0.01 to 50 mg, from 0.01 to 10 mg, from 0.01 to 1 mg, from 0.1 to 500 mg/kg, from 1 to 500 mg/kg, from 5 to 500 mg/kg, from 10 to 500 mg/kg, from 50 to 500 mg/kg, from 100 to 500 mg/kg, from 150 to 500 mg/kg, from 200 to 500 mg/kg, from 250 to 500 mg/kg, from 300 to 500 mg/kg, from 350 to 500 mg/kg, from 400 to 500 mg/kg, or from 450 to 500 mg/kg) and, in a more specific embodiment, about 1 to about 100 mg/kg (e.g., about 1 to about 90 mg/kg, about 1 to about 80 mg/kg, about 1 to about 70 mg/kg, about 1 to about 60 mg/kg, about 1 to about 50 mg/kg, about 1 to about 40 mg/kg, about 1 to about 30 mg/kg, about 1 to about 20 mg/kg, about 1 to about 10 mg/kg, about 10 to about 100 mg/kg, about 20 to about 100 mg/kg, about 30 to about 100 mg/kg, about 40 to about 100 mg/kg, about 50 to about 100 mg/kg, about 60 to about 100 mg/kg, about 70 to about 100 mg/kg, about 80 to about 100 mg/kg, or about 90 to about 100 mg/kg). In some embodiments, a pharmaceutical composition of the disclosure may include a dosage of a binding protein described herein ranging from 0.01 to 20 mg/kg (e.g., from 0.01 to 15 mg/kg, from 0.01 to 10 mg/kg, from 0.01 to 8 mg/kg, from 0.01 to 6 mg/kg, from 0.01 to 4 mg/kg, from 0.01 to 2 mg/kg, from 0.01 to 1 mg/kg, from 0.01 to 0.1 mg/kg, from 0.01 to 0.05 mg/kg, from 0.05 to 20 mg/kg, from 0.1 to 20 mg/kg, from 1 to 20 mg/kg, from 2 to 20 mg/kg, from 4 to 20 mg/kg, from 6 to 20 mg/kg, from 8 to 20 mg/kg, from 10 to 20 mg/kg, from 15 to 20 mg/kg). The dosage may be adapted by the physician in accordance with conventional factors such as the extent of the disease and different parameters of the subject.

A pharmaceutical composition containing a IL2Rg binding molecule described herein can be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines. A course of therapy may be a single dose or in multiple doses over a period of time. In some embodiments, a single dose is used. In some embodiments, two or more split doses administered over a period of 1, 2, 3, 4, 5, 6, 7, 8, 9, 10, 11, 12, 13, 14, 21, 28, 30, 60, 90, 120 or 180 days are used. Each dose administered in such split dosing protocols may be the same in each administration or may be different. Multi-day dosing protocols over time periods may be provided by the skilled artisan (e.g., physician) monitoring the administration, taking into account the response of the subject to the treatment including adverse effects of the treatment and their modulation as discussed above.

For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In some embodiments the condition to be treated is a chronic condition (e.g., a chronic infection, i.e., an infection that is not cleared by the host immune system within a period of up to 1 week, 2 weeks, etc.). In some cases, chronic condition involve integration of pathogen genetic elements into the host genome, e.g., retroviruses, lentiviruses, Hepatitis B virus, etc. In other cases, chronic infections, for example certain intracellular bacteria or protozoan pathogens, result from a pathogen cell residing within a host cell. Additionally, in some embodiments, the infection is in a latent stage, as with herpes viruses or human papilloma viruses. In such instances, the course of therapy may involve the administration of the IL2Rg binding molecule over an extended period of time including continued administration in the substantial absence of the symptoms of the chronic condition to prevent recurrence of the chronic conditions or symptoms thereof.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Routes of Administration

Administration of a IL2Rg binding molecules described herein may be achieved through any of a variety of art recognized methods including but not limited to the topical, intravascular injection (including intravenous or intraarterial infusion), intradermal injection, subcutaneous injection, intramuscular injection, intraperitoneal injection, intracranial injection, intratumoral injection, intranodal injection, transdermal, transmucosal, iontophoretic delivery, intralymphatic injection (Senti and Kundig (2009) *Current Opinions in Allergy and Clinical Immunology* 9(6):537-543), intragastric infusion, intraprostatic injection, intravesical infusion (e.g., bladder), respiratory inhalers including nebulizers, intraocular injection, intraabdominal injection, intralesional injection, intraovarian injection, intracerebral infusion or injection, intracerebroventricular injection (ICVI), and the like. Administration to the subject may be achieved by intravenous, as a bolus or by continuous infusion over a period of time. Examples of parenteral routes of administration include, for example, intravenous, intradermal, subcutaneous, transdermal (topical), transmucosal, and rectal administration. The IL2Rg binding molecule can be administered once, continuously, such as by continuous pump, or at periodic (e.g., daily, bi-weekly, monthly) intervals over a period of time can occur over the period of one week, two weeks, one month, two months, three months or more. Desired time intervals of multiple doses of the IL2Rg binding molecule may be determined by one of skill in the art.

As described hereinabove, the compositions of the present disclosure may be used in combination with one or more additional therapeutically effective agents. As used herein, the term "in combination with" when used in reference to the administration of multiple agents to a subject refers to the administration of a first agent at least one additional (i.e. second, third, fourth, fifth, etc.) supplementary agent to a subject. For purposes of the present disclosure, one agent (e.g., a IL2Rg binding molecule) is considered to be administered in combination with a supplementary agent if the biological effect resulting from the administration of the first agent persists in the subject at the time of administration of the supplementary agent such that the therapeutic effects of the first agent and second agent overlap. The administration of the first agent may provide a therapeutic effect over an extended time and the administration of the supplementary agent provides its therapeutic effect while the therapeutic effect of the first agent remains ongoing such that the supplementary agent is considered to be administered in combination with the first agent, even though the first agent may have been administered at a point in time significantly distant (e.g., days or weeks) from the time of administration of the supplementary agent. In one embodiment, one agent is considered to be administered in combination with a supplementary agent if the first and second agents are administered simultaneously (within 30 minutes of each other), contemporaneously or sequentially. In some embodiments, a first agent is deemed to be administered "contemporaneously" with a supplementary agent if first and supplementary agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a supplementary agent are co-formulated in single pharmaceutically acceptable formulation and the co-formulation is administered to a subject. In certain embodiments, first agent and the supplementary agent(s) are administered or applied sequentially, e.g., where one agent is administered prior to one or more other agents. In other embodiments, the first agent and the supplementary agent(s) are administered simultaneously, for example where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Kits

The present disclosure also contemplates kits comprising pharmaceutical compositions of IL2Rg binding molecules. In some embodiments, the kit further comprises supplementary pharmaceutical compositions comprising supplementary agents as discussed above for use in combination therapy with IL2Rg binding molecules. The kits are generally in the form of a physical structure housing various components, as described below, and can be utilized, for example, in practicing the methods described above. A kit may comprise a IL2Rg binding molecule in the form of a pharmaceutical composition suitable for administration to a subject that is ready for use or in a form or requiring preparation for example, thawing, reconstitution or dilution prior to administration. When the IL2Rg binding molecule is in a form that requires reconstitution by a user, the kit may also comprise a sterile container providing a reconstitution medium comprising buffers, pharmaceutically acceptable excipients, and the like. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL2Rg binding molecule or kit comprising) in compliance with governmental regulations (e.g., HIPAA) are provided.

EXAMPLES

The following examples are put forth so as to provide those of ordinary skill in the art with a complete disclosure and description of how to make and use the present IL2Rg binding molecule, and are not intended to limit the scope of what the inventors regard as their IL2Rg binding molecule nor are they intended to represent that the experiments below were performed and are all of the experiments that can be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for. Variations of the particularly described procedures employed may become apparent to individuals or skill in the art and it is expected that those skilled artisans may employ such variations as appropriate. Accordingly, it is intended that the IL2Rg binding molecule be practiced otherwise than as specifically described herein, and that the invention includes all modifications and equivalents of the subject matter recited in the claims appended hereto as permitted by applicable law.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; µg=microgram; mg=milligram; g=gram; kg=kilogram; dl or dL=deciliter; µl or µL=microliter; ml or mL=milliliter; l or L=liter; pM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-hydroxysuccinimide; HSA=human serum albumin; MSA=mouse serum albumin; DMEM=Dulbeco's Modification of Eagle's Medium; GC=genome copy; EDTA=ethylenediaminetetraacetic acid; PBMCs=primary peripheral blood mononuclear cells; FBS=fetal bovine serum; FCS=fetal calf serum; HEPES=4-(2-hydroxyethyl)-1piperazineethanesulfonic acid; LPS=lipopolysaccharide; ATCC=American Type Culture Collection Example 1. Camel Immunization The VHH was obtained by immunization of a camel with the extracellular domain (amino acids 23-369) of the human IL2Rg polypeptide, UNIPROT Reference P31785. A synthetic DNA sequence encoding the antigen was inserted into the pFUSE_hIgG1_Fc2 vector (Generay Biotechnology) and transfected into the HEK293F mammalian cell host cell for expression. The antigen is expressed as an Fc fusion protein which is purified using Protein A chromatography. The antigen was diluted with 1×PBS (antigen total about 1 mg). The quality was estimated by SDS-PAGE to ensure the purity was sufficient (>80%) for immunization. The camel was acclimated at the facility for at least 7 days before immunization. The immunization with the antigen was conducted using once weekly administration of the antigen over a period of 7 weeks. For the initial immunization, the immunogen was prepared as follows: 10 mL of complete Freund's Adjuvant (CFA) was added into mortar, then 10 mL antigen in 1×PBS was slowly added into the mortar with the pestle grinding and sample ground until the antigen was emulsified until milky white and hard to disperse. For the subsequent six immunizations (weeks 2-7) in the immunization protocol, immunogen was prepared as above except that Incomplete Freund's Adjuvant (IFA) was used in place of CFA. At least six sites on the camel were injected subcutaneously with approximately 2 ml of the emulsified antigen for a total of approximately 10 mL per camel. When injecting the antigen, the needle is maintained in the in the subcutaneous space for approximately 10 to 15 seconds after each injection to avoid leakage of the emulsion.

Example 2. Phage Library Construction

A blood sample was collected from the camel three days following the last injection in the immunization protocol. RNA was extracted from blood and transcribed to cDNA. The approximately 900 bp reverse transcribed sequences encoding the VH-CH1-hinge-CH2-CH3 constructs were isolated from the approximately desired 700 bp fragments encoding the VHH-hinge-CH2-CH3 species. The purified approximately 700 bp fragments were amplified by nested PCR. The amplified sequences were digested using Pst1 and Not1. The approximately 400 bp PST1/Not1 digested fragments were inserted into a Pst1/Not1 digested pMECS phagemid vector such that the sequence encoding the VHH was in frame with a DNA sequence encoding a HA/His sequence. The PCR generated sequences and the vector of pMECS phagemid were digested with Pst I and Not I, subsequently, ligated to pMECS/Nb recombinant. After ligation, the products were transformed into *Escherichia coli* (*E. coli*) TG1 cells by electroporation. The transformants were enriched in growth medium, followed by transfer to 2YT+ 2% glucose agar plates.

Example 3: Isolation of Antigen Specific VHHs

Bio-panning of the phage library was conducted to identify VHHs that bind IL2Rg. A 96-well plate was coated with IL2Rg and the phage library was incubated in each well to allow phage-expressing IL2Rg reactive VHH to bind to the IL2Rg on the plate. Non-specifically bound phage were washed off and the specifically bound phage isolated. After the selection, the enriched phage library expressing IL2Rg reactive VHH were amplified in TG1 cells. The aforementioned bio-panning process was repeated for 2-3 rounds to enrich the library for VHH selective for IL2Rg.

Example 4: Identification of Antibodies Exhibiting Specific Binding to IL2Rg

Upon completion of the biopanning of Example 3, three 96-well plates of individual phage clones were isolated in order to perform periplasmic extract ELISA (PE-ELISA) on IL2Rg coated plates to identify positive VHH binders that selectively bound IL2Rg. A 96-well plate was coated with IL2Rg and PBS under the same conditions. Next, wells were blocked at 37° C. for 1 h. Then, 100 µl of extracted antibodies was added to each well and incubated for 1 h. Subsequently, 100 µl of anti-tag polyclonal antibody conjugated to HRP was added to each well and incubated at 37° C. for 1 h. Plates were developed with TMB substrate. The reaction was stopped by the addition of $H_2SO_4$. Absorbance at 450 nm was read on a microtiter plate reader. Antibodies with absorbance of the antigen-coated well at least threefold greater than PBS-coated control are VHHs that specifically bind to IL2Rg. Positive clones were sequenced, and sequences analyzed to identify unique clonotypes.

Example 5 Evaluation of Binding Affinity Via Surface Plasmon Resonance

One representative example from each clonotype generated in accordance with Examples 1-3 was selected for evaluation of binding via SPR as follows. Evaluation of binding affinity of the IL2Rb binding molecules for CD122 corresponding to SEQ ID NOS: 30, 62, 73, 77, 81 and 85 was conducted using surface plasmon resonance (SPR) in substantial accordance with the following procedure. All experiments were conducted in 10 mM Hepes, 150 mM NaCl, 0.05% (v/v) Polysorbate 20 (PS20) and 3 mM EDTA (HBS-EP+ buffer) on a Biacore T200 instrument equipped with a Protein A derivatized sensor chip (Cytiva). Mono-Fc VHH ligands were flowed at 5 µl/min for variable time ranging from 18 to 300 seconds, reaching the capture loads listed in the tables below. Following ligand capture, injections of a 2-fold dilution series of the extracellular domain of the IL2Rb-receptor modified to incorporate a C-terminal poly-His sequence, typically comprising at least five concentrations between 1 µM and 1 nM, were performed in either high performance or single cycle kinetics mode. Surface regeneration was achieved by flowing 10 mM glycine-HCl, pH 1.5 (60 seconds, 50 µL/min). Buffer-subtracted sensograms were processed with Biacore T200 Evaluation Software and globally fit with a 1:1 Langmuir binding model (bulk shift set to zero) to extract kinetics and affinity constants ($k_a$, $k_d$, $K_D$). $R_{MAX}$<100 RU indicates surface density compatible with kinetics analysis. Calculated $R_{max}$ values were generated using the equation: $R_{max}$=Load (RU)×valency of ligand×(Molecular weight of analyte/Molecular weight of ligand). Surface activity was defined as the ratio of experimental/calculated $R_{max}$. The results of these binding affinity experiments are provided in Table 6.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

The invention claimed is:

1. An IL2Rg binding molecule that specifically binds to the extracellular domain of IL2Rg, wherein the IL2Rg binding molecule comprises a single domain antibody (sdAb), and wherein the sdAb comprises a complementary determining region 1 (CDR1), a CDR2, and a CDR3 as shown in a row of the table below:

| CDR1 | CDR2 | CDR3 |
|---|---|---|
| FTFDDSDMG (SEQ ID NO: 2) | TISSDGSTYYADSVKG (SEQ ID NO: 3) | DFMIAIQAPGAGC (SEQ ID NO: 4) |
| FSFSSYPMT (SEQ ID NO: 6) | TIASDGGSTAYAASVEG (SEQ ID NO: 7) | GYGDGTPA (SEQ ID NO: 8) |
| FTFDDREMN (SEQ ID NO: 10) | TISSDGSTYYADSVKG (SEQ ID NO: 11) | DFMIAIQAPGAGC (SEQ ID NO: 12) |
| FTFDDSDMG (SEQ ID NO: 14) | TISSDGNTYYTDSVKG (SEQ ID NO: 15) | EPRGYYSNYGGRRECNY (SEQ ID NO: 16) |
| FSFSSYPMT (SEQ ID NO: 18) | TIASDGGSTAYAASVEG (SEQ ID NO: 19) | GYGDGTPA (SEQ ID NO: 20) |
| FTFSNAHMS (SEQ ID NO: 22) | SIYSGGSTWYADSVKG (SEQ ID NO: 23) | NRLHYYSDDDSL (SEQ ID NO: 24) |
| FTFDDREMN (SEQ ID NO: 26) | TISSDGSTYYADSVKG (SEQ ID NO: 27) | DFMIAIQAPGAGC (SEQ ID NO: 28) |
| YTFSSYCMG (SEQ ID NO: 30) | ALGGGSTYYADSVKG (SEQ ID NO 31) | AWVACLEFGGSWYDLARYKH (SEQ ID NO 32) |
| FTFDDSDMG (SEQ ID NO 34) | TISSDGSTYYADSVKG (SEQ ID NO 35) | EPRGYYSNYGGRRECNY (SEQ ID NO 36) |
| SIYSSAYIG (SEQ ID NO 38) | GIYTRDGSTAYADSVKG (SEQ ID NO 39) | GRRTKSYVYIFRPEEYNY (SEQ ID NO 40) |
| FTFSSAHMS (SEQ ID NO 42) | SIYSGGGTFYADSVKG (SEQ ID NO 43) | NRLHYYSDDDSL (SEQ ID NO 44) |
| FTFSNAHMS (SEQ ID NO 46) | SIYSGGSTWYADSVKG (SEQ ID NO 47) | NRLHYYSDDDSL (SEQ ID NO 48) |
| FIFDDSDMG (SEQ ID NO 50) | TISSDGSTYYADSVKG (SEQ ID NO 51) | EPRGYYSNYGGRRECNY (SEQ ID NO 52) |
| FTADDSDMG (SEQ ID NO 54) | TISSDGSTYYADSVKG (SEQ ID NO 55) | EPRGYYSNYGGRRECNY (SEQ ID NO 56) |
| FTFSSAHMS (SEQ ID NO 58) | SIYSGGGTFYADSVKG (SEQ ID NO 59) | NRLHYYSDDDSL (SEQ ID NO 60) |
| FTFSNAHMS (SEQ ID NO 62) | SIYSGGSTWYADSVKG (SEQ ID NO 63) | NRLHYYSDDDSL (SEQ ID NO 64) |
| FTFSNAHMS (SEQ ID NO 66) | SIYSGGSTWYADSVKG (SEQ ID NO 67) | NRLHYYSDDDSL (SEQ ID NO 68 |
| FTFSSYPMT (SEQ ID NO 70) | TIASDGGSTAYAASVEG (SEQ ID NO 71) | GYGDGTPA (SEQ ID NO 72) |
| FTFDDREMN (SEQ ID NO 74) | TISSDGSTYYADSVKG (SEQ ID NO 75) | DFMIAIQAPGAGC (SEQ ID NO 76) |
| FTFDDSDMG (SEQ ID NO 78) | TISSDGSTYYADSVKG (SEQ ID NO 79) | EPRGYYSNYGGRRECNY (SEQ ID NO 80) |
| YTSCMG (SEQ ID NO 82) | TIYTRGRSIYYADSVKG (SEQ ID NO 83) | GGYSWSAGCEFNY (SEQ ID NO 84) |
| FSFSSYPMT (SEQ ID NO 86) | TIASDGGSTAYAASVEG (SEQ ID NO 87) | GYGDGTPA (SEQ ID NO 88) |
| FSFSSYPMT (SEQ ID NO 90) | TIASDGGSTAYAASVEG (SEQ ID NO 91) | GYGDGTPA (SEQ ID NO 92). |

2. The IL2Rg binding molecule of claim 1, wherein the sdAb has at least 95% amino acid sequence identity to a polypeptide sequence of any one of SEQ ID NOS: 1, 5, 9, 13, 17, 21, 25, 29, 33, 37, 41, 45, 49, 53, 57, 61, 65, 69, 73, 77, 81, 85, or 89.

3. An IL2Rg binding molecule that specifically binds to the extracellular domain of IL2Rg, wherein the IL2Rg binding molecule comprises a single domain antibody (sdAb), and wherein the sdAb comprises a complementary determining region 1 (CDR1), a CDR2, and a CDR3 as shown in a row of the table below:

| CDR1 AA Seq | CDR1 SEQ ID | CDR2 AA Seq | CDR2 SEQ ID | CDR3 AA Seq | CDR3 SEQ ID |
|---|---|---|---|---|---|
| STYANYLMG | 121 | AIYSGGGSTYYADSVKG | 122 | ASAVKGDKGDIVVVVTGTQRMEYDY | 123 |
| FTFDESVMS | 125 | IISSDDNTYYDDSVKG | 126 | RRRRPVYDSDYELRPRPLCGDFGV | 127 |
| LPFDEDDMG | 129 | SISSDGTAYYADSVKG | 130 | GVHRQFGGSSSCGDAFYGMDY | 131 |
| DVYGRNSMA | 133 | VGYSVVTTTYYADSVKG | 134 | DGNLWRGLRPSEYTY | 135 |
| FPYSRYCMG | 137 | AIEPDGSTSYADSVKG | 138 | DERCFYLKDYDLRRPAQYRY | 139 |

-continued

| CDR1 AA Seq | CDR1 SEQ ID | CDR2 AA Seq | CDR2 SEQ ID | CDR3 AA Seq | CDR3 SEQ ID |
|---|---|---|---|---|---|
| FTFDESDMG | 141 | VITSDDNPYYDDSVKG | 142 | RSRQPVYSRDYELRPRPLCGDFGV | 143 |
| FTFDDFDMG | 145 | TISDDGSTYYADSVKG | 146 | EGALGSKTNCGWVGNFGY | 147 |
| FTFDDFDMG | 149 | TISDDGSTYYADSVKG | 150 | EGALGSKTNCGWVGNFGY | 151 |
| FTFDDFDMG | 153 | TISDDGSTYYADSVKG | 154 | EGALGSKTNCGWVGNFGY | 155 |
| FTFSDRDMG | 157 | TISDDGSTYYADSVKG | 158 | EGALGSKTNCGWVGNFGY | 159 |
| YGYNYIG | 161 | VIYIGGGDTYYADSVKG | 162 | RYCVGSVYACLRGGHDEYAH | 163 |
| YGYNYIG | 165 | VIYTGGGDTYYADSVKG | 166 | RYCVGSVYACLRGGHDEYAH | 167 |
| FTFDDFDMG | 169 | TISDDGSTYYANSVKG | 170 | EGALGSKTNCGWVGNFGY | 171 |
| FTFDDFDMG | 173 | TISDDGSTYYADSVKG | 174 | EGALGSKMNCGWVGNFGY | 175. |

4. The IL2Rg binding molecule of claim 3, wherein the sdAb has at least 95% amino acid sequence identity to a polypeptide sequence of any one of SEQ ID NOS: 116, 120, 124, 128, 132, 136, 140, 144, 148, 152, 156, 160, 164 168, or 172.

5. The IL2Rg binding molecule of claim 1, wherein the sdAb is humanized or otherwise comprises CDRs grafted onto a heterologous framework.

6. The IL2Rg binding molecule of claim 1, further comprising one or more of a labeling agent, an imaging agent, and a therapeutic agent.

7. A method for isolating, depleting, or enriching IL2Rg+ cells in a biological sample, comprising contacting the biological sample with the IL2Rg binding molecule of claim 1.

8. A nucleic acid sequence encoding the IL2Rg binding molecule of claim 1.

9. A recombinant viral or non-viral vector comprising a nucleic acid of claim 8.

10. A host cell comprising a nucleic acid of claim 8.

11. A pharmaceutical formulations comprising the viral or non-viral vector of claim 9.

12. A kit comprising the IL2Rg binding molecule of claim 1.

13. The IL2Rg binding molecule of claim 1, wherein the sdAb comprises the CDR1, the CDR2, and the CDR3 of SEQ ID NOS:86, 87, and 88, respectively.

14. The IL2Rg binding molecule of claim 13, wherein the sdAb has at least 95% amino acid sequence identity to a polypeptide sequence of SEQ ID NO:85.

15. The IL2Rg binding molecule of claim 1, wherein the sdAb comprises the CDR1, the CDR2, and the CDR3 of SEQ ID NOS:74, 75, and 76, respectively.

16. The IL2Rg binding molecule of claim 15, wherein the sdAb has at least 95% amino acid sequence identity to a polypeptide sequence of SEQ ID NO:73.

17. The IL2Rg binding molecule of claim 1, wherein the sdAb comprises the CDR1, the CDR2, and the CDR3 of SEQ ID NOS:78, 79, and 80, respectively.

18. The IL2Rg binding molecule of claim 17, wherein the sdAb has at least 95% amino acid sequence identity to a polypeptide sequence of SEQ ID NO:77.

19. The nucleic acid sequence of claim 8, encoding the IL2Rg binding molecule comprising the sdAb having the CDR1, the CDR2, and the CDR3 of SEQ ID NOS:86, 87, and 88, respectively.

20. The nucleic acid sequence of claim 8, encoding the IL2Rg binding molecule comprising the sdAb having the CDR1, the CDR2, and the CDR3 of SEQ ID NOS:74, 75, and 76, respectively.

21. The nucleic acid sequence of claim 8, encoding the IL2Rg binding molecule comprising the sdAb having the CDR1, the CDR2, and the CDR3 of SEQ ID NOS:78, 79, and 80, respectively.

22. The IL2Rg binding molecule of claim 1, wherein the sdAb is linked to a second binding molecule that specifically binds to the extracellular domain of a second cell surface molecule.

* * * * *

UNITED STATES PATENT AND TRADEMARK OFFICE
CERTIFICATE OF CORRECTION

| | | |
|---|---|---|
| PATENT NO. | : 12,077,594 B2 | Page 1 of 1 |
| APPLICATION NO. | : 18/006525 | |
| DATED | : September 3, 2024 | |
| INVENTOR(S) | : Kastelein et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 109 days.

Signed and Sealed this
Fifth Day of November, 2024

Katherine Kelly Vidal
*Director of the United States Patent and Trademark Office*

SEQUENCE LISTING

```
<160> NUMBER OF SEQ ID NOS: 200

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Asp Asp Ser
            20                  25                  30

Asp Met Gly Trp Tyr Arg Gln Ala Pro Gly Asn Glu Cys Asp Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asp Ser Val Lys Pro Glu Asp Thr Ala Val Tyr Tyr Cys Ala
                85                  90                  95

Ala Asp Phe Met Ile Ala Ile Gln Ala Pro Gly Ala Gly Cys Trp Gly
            100                 105                 110

Gln Gly Thr Gln Val Thr Val Ser Ser
        115                 120

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Thr Phe Asp Asp Ser Asp Met Gly
1               5

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 3

Thr Ile Ser Ser Asp Gly Ser Thr Tyr Tyr Ala Asp Ser Val Lys Gly
1               5                   10                  15

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Phe Met Ile Ala Ile Gln Ala Pro Gly Ala Gly Cys
1               5                   10

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Gly Gly Ser Val Pro Ala Gly Gly
1               5                   10                  15

Ser Leu Lys Leu Ser Cys Ala Ala Ser Gly Phe Ser Phe Ser Ser Tyr
                20                  25                  30

Pro Met Thr Trp Ala Arg Gln Ala Pro Gly Lys Gly Leu Glu Trp Val
            35                  40                  45

Ser Thr Ile Ala Ser Asp Gly Gly Ser Thr Ala Tyr Ala Ala Ser Val
        50                  55                  60

Glu Gly Arg Phe Thr Ile Ser Arg Asp Asn Ala Lys Ser Thr Leu Tyr
65                  70                  75                  80

Leu Gln Leu Asn Ser Leu Lys Thr Glu Asp Thr Ala Met Tyr Tyr Cys
                85                  90                  95

Thr Lys Gly Tyr Gly Asp Gly Thr Pro Ala Pro Gly Asn Gly Thr Gln
            100                 105                 110

Val Thr Val Ser Ser
        115

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Ser Phe Ser Ser Tyr Pro Met Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Thr Ile Ala Ser Asp Gly Gly Ser Thr Ala Tyr Ala Ala Ser Val Glu
1               5                   10                  15

Gly

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Tyr Gly Asp Gly Thr Pro Ala
1               5

<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Gly Gly Ser Val Gln Thr Gly Gly
1               5                   10                  15

Ser Leu Arg Leu Ser Cys Thr Ala Ser Gly Phe Thr Phe Asp Asp Arg
            20                  25                  30

Glu Met Asn Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asp Ser Val Lys Pro Glu Asp Thr Ala Val Tyr Tyr Cys Ala
                85                  90                  95

Ala Asp Phe Met Ile Ala Ile Gln Ala Pro Gly Ala Gly Cys Trp Gly
            100                 105                 110

Gln Gly Thr Gln Val Thr Val Ser Ser
        115                 120

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Thr Phe Asp Asp Arg Glu Met Asn
1               5

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

```
Thr Ile Ser Ser Asp Gly Ser Thr Tyr Tyr Ala Asp Ser Val Lys Gly
1               5                   10                  15
```

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Asp Phe Met Ile Ala Ile Gln Ala Pro Gly Ala Gly Cys
1               5                   10
```

<210> SEQ ID NO 13
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Ser
            20                  25                  30

Asp Met Gly Trp Tyr Arg Gln Ala Pro Gly Asn Glu Cys Glu Leu Val
        35                  40                  45

Ser Thr Ile Ser Ser Asp Gly Asn Thr Tyr Tyr Thr Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Gly Pro Glu Asp Thr Ala Val Tyr Tyr Cys Ala
                85                  90                  95

Ala Glu Pro Arg Gly Tyr Tyr Ser Asn Tyr Gly Gly Arg Arg Glu Cys
            100                 105                 110

Asn Tyr Trp Gly Gln Gly Thr Gln Val Thr Val Ser Ser
        115                 120                 125
```

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Phe Thr Phe Asp Asp Ser Asp Met Gly
1               5
```

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Thr Ile Ser Ser Asp Gly Asn Thr Tyr Tyr Thr Asp Ser Val Lys Gly
```

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Pro Arg Gly Tyr Tyr Ser Asn Tyr Gly Gly Arg Arg Glu Cys Asn
1               5                   10                  15

Tyr

<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Ser Phe Ser Ser Tyr
            20                  25                  30

Pro Met Thr Trp Ala Arg Gln Ala Pro Gly Lys Gly Leu Glu Trp Val
        35                  40                  45

Ser Thr Ile Ala Ser Asp Gly Gly Ser Thr Ala Tyr Ala Ala Ser Val
    50                  55                  60

Glu Gly Arg Phe Thr Ile Ser Arg Asp Asn Ala Lys Ser Thr Leu Tyr
65                  70                  75                  80

Leu Gln Leu Asn Ser Leu Lys Thr Glu Asp Thr Ala Met Tyr Tyr Cys
                85                  90                  95

Thr Lys Gly Tyr Gly Asp Gly Thr Pro Ala Pro Gly Gln Gly Thr Gln
            100                 105                 110

Val Thr Val Ser Ser
        115

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Phe Ser Phe Ser Ser Tyr Pro Met Thr
1               5

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Ile Ala Ser Asp Gly Gly Ser Thr Ala Tyr Ala Ala Ser Val Glu

-continued

```
1               5                   10                  15
Gly

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Tyr Gly Asp Gly Thr Pro Ala
1               5

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Glu Ser Gly Gly Gly Ala Val Gln Ala Gly Gly
1               5                   10                  15

Ser Leu Arg Leu Ser Cys Ala Ala Ser Gly Phe Thr Phe Ser Asn Ala
            20                  25                  30

His Met Ser Trp Val Arg Gln Ala Pro Gly Lys Gly Arg Glu Trp Ile
        35                  40                  45

Ser Ser Ile Tyr Ser Gly Gly Ser Thr Trp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Glu Asn Arg Leu His Tyr Tyr Ser Asp Asp Asp Ser Leu Arg Gly Gln
            100                 105                 110

Gly Thr Gln Val Thr Val Ser Ser
        115                 120

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Thr Phe Ser Asn Ala His Met Ser
1               5

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ile Tyr Ser Gly Gly Ser Thr Trp Tyr Ala Asp Ser Val Lys Gly
```

```
<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Arg Leu His Tyr Tyr Ser Asp Asp Asp Ser Leu
1               5                   10

<210> SEQ ID NO 25
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asp Asp Arg
            20                  25                  30

Glu Met Asn Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asp Ser Val Lys Pro Glu Asp Thr Ala Val Tyr Tyr Cys Ala
                85                  90                  95

Ala Asp Phe Met Ile Ala Ile Gln Ala Pro Gly Ala Gly Cys Trp Gly
            100                 105                 110

Gln Gly Thr Gln Val Thr Val Ser Ser
        115                 120

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Thr Phe Asp Asp Arg Glu Met Asn
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Ile Ser Ser Asp Gly Ser Thr Tyr Tyr Ala Asp Ser Val Lys Gly
1               5                   10                  15
```

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Phe Met Ile Ala Ile Gln Ala Pro Gly Ala Gly Cys
1               5                   10

<210> SEQ ID NO 29
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Phe Ser Ser Tyr
            20                  25                  30

Cys Met Gly Trp Phe Arg Gln Ala Pro Gly Lys Glu Arg Glu Gly Val
        35                  40                  45

Ala Ala Leu Gly Gly Gly Ser Thr Tyr Tyr Ala Asp Ser Val Lys Gly
    50                  55                  60

Arg Phe Thr Ile Ser Gln Asp Asn Ala Lys Asn Thr Leu Tyr Leu Gln
65                  70                  75                  80

Met Asn Ser Leu Lys Pro Glu Asp Thr Ala Met Tyr Tyr Cys Ala Ala
                85                  90                  95

Ala Trp Val Ala Cys Leu Glu Phe Gly Gly Ser Trp Tyr Asp Leu Ala
            100                 105                 110

Arg Tyr Lys His Trp Gly Gln Gly Thr Gln Val Thr Val Ser Ser
        115                 120                 125

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Thr Phe Ser Ser Tyr Cys Met Gly
1               5

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Leu Gly Gly Gly Ser Thr Tyr Tyr Ala Asp Ser Val Lys Gly
1               5                   10                  15

<210> SEQ ID NO 32

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Trp Val Ala Cys Leu Glu Phe Gly Gly Ser Trp Tyr Asp Leu Ala
1               5                   10                  15

Arg Tyr Lys His
            20

<210> SEQ ID NO 33
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Ser
            20                  25                  30

Asp Met Gly Trp Tyr Arg Gln Ala Pro Gly Gly Glu Cys Glu Leu Val
        35                  40                  45

Thr Ile Ser Ser Asp Gly Ser Thr Tyr Ala Asp Ser Val Lys Gly
    50                  55                  60

Arg Phe Thr Ile Ser Gln Asp Asn Ala Lys Asn Thr Val Tyr Leu Gln
65                  70                  75                  80

Met Asn Ser Leu Lys Pro Glu Asp Thr Ala Val Tyr Tyr Cys Ala Ala
                85                  90                  95

Glu Pro Arg Gly Tyr Tyr Ser Asn Tyr Gly Gly Arg Arg Glu Cys Asn
            100                 105                 110

Tyr Trp Gly Gln Gly Thr Gln Val Thr Val Ser Ser
        115                 120

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Thr Phe Asp Asp Ser Asp Met Gly
1               5

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Ile Ser Ser Asp Gly Ser Thr Tyr Tyr Ala Asp Ser Val Lys Gly
1               5                   10                  15
```

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

```
Glu Pro Arg Gly Tyr Tyr Ser Asn Tyr Gly Gly Arg Arg Glu Cys Asn
1               5                   10                  15

Tyr
```

<210> SEQ ID NO 37
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Ser Ile Tyr Ser Ser Ala
            20                  25                  30

Tyr Ile Gly Trp Phe Arg Gln Ala Pro Gly Lys Lys Arg Glu Gly Val
        35                  40                  45

Ala Gly Ile Tyr Thr Arg Asp Gly Ser Thr Ala Tyr Ala Asp Ser Val
    50                  55                  60

Lys Gly Arg Phe Thr Ile Ser Gln Asp Ser Ala Lys Lys Thr Val Tyr
65                  70                  75                  80

Leu Gln Met Asn Ser Leu Lys Pro Glu Asp Thr Ala Met Tyr Tyr Cys
                85                  90                  95

Ala Ala Gly Arg Arg Thr Lys Ser Tyr Val Tyr Ile Phe Arg Pro Glu
            100                 105                 110

Glu Tyr Asn Tyr Trp Gly Gln Gly Thr Gln Val Thr Val Ser Ser
        115                 120                 125
```

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

```
Ser Ile Tyr Ser Ser Ala Tyr Ile Gly
1               5
```

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

```
Gly Ile Tyr Thr Arg Asp Gly Ser Thr Ala Tyr Ala Asp Ser Val Lys
1               5                   10                  15

Gly
```

```
<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Arg Arg Thr Lys Ser Tyr Val Tyr Ile Phe Arg Pro Glu Glu Tyr
1               5                   10                  15

Asn Tyr

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Ser Ser Ala
            20                  25                  30

His Met Ser Trp Val Arg Gln Ala Pro Gly Lys Gly Arg Glu Trp Ile
        35                  40                  45

Ala Ser Ile Tyr Ser Gly Gly Thr Phe Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Thr Asn Arg Leu His Tyr Tyr Ser Asp Asp Ser Leu Arg Gly Gln
            100                 105                 110

Gly Thr Gln Val Thr Val Ser Ser
        115                 120

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Thr Phe Ser Ser Ala His Met Ser
1               5

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ile Tyr Ser Gly Gly Gly Thr Phe Tyr Ala Asp Ser Val Lys Gly
1               5                   10                  15
```

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asn Arg Leu His Tyr Tyr Ser Asp Asp Asp Ser Leu
1               5                   10

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Ser Asn Ala
            20                  25                  30

His Met Ser Trp Val Arg Gln Ala Pro Gly Lys Gly Arg Glu Trp Ile
        35                  40                  45

Ser Ser Ile Tyr Ser Gly Gly Ser Thr Trp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Glu Asn Arg Leu His Tyr Tyr Ser Asp Asp Asp Ser Leu Arg Gly Gln
            100                 105                 110

Gly Thr Gln Val Thr Val Ser Ser
        115                 120

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Phe Thr Phe Ser Asn Ala His Met Ser
1               5

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Ile Tyr Ser Gly Gly Ser Thr Trp Tyr Ala Asp Ser Val Lys Gly
1               5                   10                  15

```
<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asn Arg Leu His Tyr Tyr Ser Asp Asp Asp Ser Leu
1               5                   10

<210> SEQ ID NO 49
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Glu Ser Gly Gly Gly Ser Val Gln Ala Gly Gly
1               5                   10                  15

Ser Leu Arg Leu Ser Cys Thr Ala Ser Arg Phe Ile Phe Asp Asp Ser
            20                  25                  30

Asp Met Gly Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Glu Pro Arg Gly Tyr Tyr Ser Asn Tyr Gly Gly Arg Arg Glu Cys
            100                 105                 110

Asn Tyr Trp Gly Gln Gly Thr Gln Val Thr Val Ser Ser
        115                 120                 125

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Phe Ile Phe Asp Asp Ser Asp Met Gly
1               5

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ile Ser Ser Asp Gly Ser Thr Tyr Tyr Ala Asp Ser Val Lys Gly
1               5                   10                  15

<210> SEQ ID NO 52
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Pro Arg Gly Tyr Tyr Ser Asn Tyr Gly Gly Arg Arg Glu Cys Asn
1               5                  10                  15

Tyr

<210> SEQ ID NO 53
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Gln Glu Ser Gly Gly Gly Ser Val Gln Ala Gly Gly
1               5                  10                  15

Ser Leu Lys Leu Ser Cys Thr Val Ser Gly Phe Thr Ala Asp Asp Ser
            20                  25                  30

Asp Met Gly Trp Tyr Arg Gln Gly Pro Gly Asn Glu Cys Glu Leu Val
        35                  40                  45

Thr Ile Ser Ser Asp Gly Ser Thr Tyr Tyr Ala Asp Ser Val Lys Gly
    50                  55                  60

Arg Phe Thr Ile Ser Gln Asp Asn Ala Lys Asn Thr Val Tyr Leu Gln
65                  70                  75                  80

Met Asn Ser Leu Lys Pro Glu Asp Thr Ala Val Tyr Tyr Cys Ala Ala
                85                  90                  95

Glu Pro Arg Gly Tyr Tyr Ser Asn Tyr Gly Gly Arg Arg Glu Cys Asn
            100                 105                 110

Tyr Trp Gly Gln Gly Thr Gln Val Thr Val Ser Ser
        115                 120

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Phe Thr Ala Asp Asp Ser Asp Met Gly
1               5

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Ile Ser Ser Asp Gly Ser Thr Tyr Tyr Ala Asp Ser Val Lys Gly
1               5                  10                  15

<210> SEQ ID NO 56
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Pro Arg Gly Tyr Tyr Ser Asn Tyr Gly Gly Arg Arg Glu Cys Asn
1               5                   10                  15

Tyr

<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

His Met Ser Trp Val Arg Gln Ala Pro Gly Lys Gly Arg Glu Trp Ile
        35                  40                  45

Ala Ser Ile Tyr Ser Gly Gly Thr Phe Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Ser Leu Lys Ala Glu Asp Thr Ala Met Tyr Tyr Cys Ala
                85                  90                  95

Thr Asn Arg Leu His Tyr Tyr Ser Asp Asp Asp Ser Leu Arg Gly Gln
            100                 105                 110

Gly Thr Gln Val Thr Val Ser Ser
        115                 120

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Phe Thr Phe Ser Ser Ala His Met Ser
1               5

<210> SEQ ID NO 59
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Ile Tyr Ser Gly Gly Gly Thr Phe Tyr Ala Asp Ser Val Lys Gly
1               5                   10                  15

<210> SEQ ID NO 60
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asn Arg Leu His Tyr Tyr Ser Asp Asp Asp Ser Leu
1               5                   10

<210> SEQ ID NO 61
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Glu Ser Gly Gly Gly Leu Val Gln Pro Gly Gly
1               5                   10                  15

Ser Leu Arg Leu Ser Cys Val Ala Ser Gly Phe Thr Phe Ser Asn Ala
            20                  25                  30

His Met Ser Trp Val Arg Gln Ala Pro Gly Lys Gly Arg Glu Trp Ile
        35                  40                  45

Ser Ser Ile Tyr Ser Gly Gly Ser Thr Trp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Glu Asn Arg Leu His Tyr Tyr Ser Asp Asp Asp Ser Leu Arg Gly Gln
            100                 105                 110

Gly Thr Gln Val Thr Val Ser Ser
        115                 120

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Phe Thr Phe Ser Asn Ala His Met Ser
1               5

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Ile Tyr Ser Gly Gly Ser Thr Trp Tyr Ala Asp Ser Val Lys Gly
1               5                   10                  15

<210> SEQ ID NO 64
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 64

Asn Arg Leu His Tyr Tyr Ser Asp Asp Ser Leu
1               5                   10

<210> SEQ ID NO 65
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ala
            20                  25                  30

His Met Ser Trp Val Arg Gln Ala Pro Gly Lys Gly Arg Glu Trp Ile
        35                  40                  45

Ser Ser Ile Tyr Ser Gly Gly Ser Thr Trp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Leu Asn Ser Leu Lys Thr Glu Asp Thr Ala Met Tyr Tyr Cys Ala
                85                  90                  95

Glu Asn Arg Leu His Tyr Tyr Ser Asp Asp Ser Leu Arg Gly Gln
            100                 105                 110

Gly Thr Gln Val Thr Val Ser Ser
        115                 120

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Thr Phe Ser Asn Ala His Met Ser
1               5

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Ile Tyr Ser Gly Gly Ser Thr Trp Tyr Ala Asp Ser Val Lys Gly
1               5                   10                  15

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 68

Asn Arg Leu His Tyr Tyr Ser Asp Asp Asp Ser Leu
1               5                   10

<210> SEQ ID NO 69
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Thr Trp Ala Arg Gln Ala Pro Gly Lys Gly Leu Glu Trp Val
        35                  40                  45

Ser Thr Ile Ala Ser Asp Gly Gly Ser Thr Ala Tyr Ala Ala Ser Val
    50                  55                  60

Glu Gly Arg Phe Thr Ile Ser Arg Asp Asn Ala Lys Ser Thr Leu Tyr
65                  70                  75                  80

Leu Gln Leu Asn Ser Leu Lys Thr Glu Asp Thr Ala Met Tyr Tyr Cys
                85                  90                  95

Thr Lys Gly Tyr Gly Asp Gly Thr Pro Ala Pro Gly Gln Gly Thr Gln
            100                 105                 110

Val Thr Val Ser Ser
        115

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Phe Thr Phe Ser Ser Tyr Pro Met Thr
1               5

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Ile Ala Ser Asp Gly Gly Ser Thr Ala Tyr Ala Ala Ser Val Glu
1               5                   10                  15

Gly

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Gly Tyr Gly Asp Gly Thr Pro Ala
1               5

<210> SEQ ID NO 73
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Arg
            20                  25                  30

Glu Met Asn Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asp Ser Val Lys Pro Glu Asp Thr Ala Val Tyr Tyr Cys Ala
                85                  90                  95

Ala Asp Phe Met Ile Ala Ile Gln Ala Pro Gly Ala Gly Cys Trp Gly
            100                 105                 110

Gln Gly Thr Gln Val Thr Val Ser Ser
        115                 120

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe Thr Phe Asp Asp Arg Glu Met Asn
1               5

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Ile Ser Ser Asp Gly Ser Thr Tyr Tyr Ala Asp Ser Val Lys Gly
1               5                   10                  15

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Phe Met Ile Ala Ile Gln Ala Pro Gly Ala Gly Cys
1               5                   10

<210> SEQ ID NO 77
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Ser
            20                  25                  30

Asp Met Gly Trp Tyr Arg Gln Ala Pro Gly Asn Glu Cys Glu Leu Val
        35                  40                  45

Ser Thr Ile Ser Ser Asp Gly Ser Thr Tyr Tyr Ala Asp Ser Val Lys
    50                  55                  60

Gly Arg Phe Thr Ile Ser Gln Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Glu Pro Arg Gly Tyr Tyr Ser Asn Tyr Gly Gly Arg Arg Glu Cys
            100                 105                 110

Asn Tyr Trp Gly Gln Gly Thr Gln Val Thr Val Ser Ser
        115                 120                 125

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Phe Thr Phe Asp Asp Ser Asp Met Gly
1               5

<210> SEQ ID NO 79
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Ile Ser Ser Asp Gly Ser Thr Tyr Tyr Ala Asp Ser Val Lys Gly
1               5                   10                  15

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Glu Pro Arg Gly Tyr Tyr Ser Asn Tyr Gly Gly Arg Arg Glu Cys Asn
1               5                   10                  15

Tyr

<210> SEQ ID NO 81
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Gln Glu Ser Gly Gly Gly Ser Val Gln Ala Gly Gly
1               5                   10                  15

Ser Leu Arg Leu Ser Cys Val Ala Ser Gly Tyr Thr Ser Cys Met Gly
            20                  25                  30

Trp Phe Arg Gln Ala Pro Gly Lys Glu Arg Glu Ala Val Ala Thr Ile
        35                  40                  45

Tyr Thr Arg Gly Arg Ser Ile Tyr Tyr Ala Asp Ser Val Lys Gly Arg
    50                  55                  60

Phe Thr Ile Ser Gln Asp Asn Ala Lys Asn Thr Leu Tyr Leu Gln Met
65                  70                  75                  80

Asn Ser Leu Lys Pro Glu Asp Ile Ala Met Tyr Ser Cys Ala Ala Gly
                85                  90                  95

Gly Tyr Ser Trp Ser Ala Gly Cys Glu Phe Asn Tyr Trp Gly Gln Gly
            100                 105                 110

Thr Gln Val Thr Val Ser Ser
        115

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Tyr Thr Ser Cys Met Gly
1               5

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Ile Tyr Thr Arg Gly Arg Ser Ile Tyr Tyr Ala Asp Ser Val Lys
1               5                   10                  15

Gly

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Gly Tyr Ser Trp Ser Ala Gly Cys Glu Phe Asn Tyr
1               5                   10

<210> SEQ ID NO 85
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Ser Phe Ser Ser Tyr
            20                  25                  30

Pro Met Thr Trp Ala Arg Gln Ala Pro Gly Lys Gly Leu Glu Trp Val
        35                  40                  45

Ser Thr Ile Ala Ser Asp Gly Gly Ser Thr Ala Tyr Ala Ala Ser Val
    50                  55                  60

Glu Gly Arg Phe Thr Ile Ser Arg Asp Asn Ala Lys Ser Thr Leu Tyr
65                  70                  75                  80

Leu Gln Leu Asn Ser Leu Lys Thr Glu Asp Thr Ala Met Tyr Tyr Cys
                85                  90                  95

Thr Lys Gly Tyr Gly Asp Gly Thr Pro Ala Pro Gly Gln Gly Thr Gln
            100                 105                 110

Val Thr Val Ser Ser
        115

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Phe Ser Phe Ser Ser Tyr Pro Met Thr
1               5

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Ile Ala Ser Asp Gly Gly Ser Thr Ala Tyr Ala Ala Ser Val Glu
1               5                   10                  15

Gly

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Tyr Gly Asp Gly Thr Pro Ala
1               5

<210> SEQ ID NO 89
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Pro Met Thr Trp Ala Arg Gln Ala Pro Gly Lys Gly Leu Glu Trp Val
        35                  40                  45

Ser Thr Ile Ala Ser Asp Gly Gly Ser Thr Ala Tyr Ala Ala Ser Val
    50                  55                  60

Glu Gly Arg Phe Thr Ile Ser Arg Asp Asn Ala Lys Ser Thr Leu Tyr
65                  70                  75                  80

Leu Gln Leu Asn Ser Leu Lys Thr Glu Asp Thr Ala Met Tyr Tyr Cys
                85                  90                  95

Thr Lys Gly Tyr Gly Asp Gly Thr Pro Ala Pro Gly Gln Gly Thr Gln
            100                 105                 110

Val Thr Val Ser Ser
        115

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe Ser Phe Ser Ser Tyr Pro Met Thr
1               5

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr Ile Ala Ser Asp Gly Gly Ser Thr Ala Tyr Ala Ala Ser Val Glu
1               5                   10                  15

Gly

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Tyr Gly Asp Gly Thr Pro Ala
1               5

<210> SEQ ID NO 93
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
caggtccagc tccaggagag cggggcggt tctgtgcaag ccggaggctc attgagactc      60
tcatgcgctg caagtggttt taccttcgat gacagcgata tgggatggta tcgtcaggct    120
ccgggcaatg agtgtgatct ggtctccact atctcctctg atggttccac atactatgct    180
gactctgtca aggggcgctt taccatctcc aagataatg ccaagaacac cgtgtacctt     240
cagatggatt cagttaagcc cgaggacaca gccgtctatt actgcgctgc ggattttatg    300
attgccatcc aagctcccgg agcgggatgc tggggccagg gaacccaggt cactgtgagc    360
agt                                                                  363

<210> SEQ ID NO 94
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
caggtgcagt tgcaggagtc cggcggggt tctgtgccag cgggtgggag cctcaagctc      60
tcctgtgccg cttccggctt ctcattctcc tcttacccta tgacctgggc acgccaagcg    120
cccggcaagg gactggaatg ggtgtccacc attgcttccg atggcggtag tacagcctac    180
gccgcgtcag tggagggtcg gttcacgatc agcgggaca acgcgaagag cacactctac     240
ctccagctga actctctgaa gaccgaggac accgccatgt actattgcac aaagggctac    300
ggcgacggca ccccggcacc cggccagggc acccaggtga cagtctcttc c              351

<210> SEQ ID NO 95
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
caggtgcagt tgcaggaaag tggtggaggg agtgtgcaga ctgggggctc tctccgcctc      60
agctgcacag cctctggatt taccttcgat gatcgcgaga tgaactggta tcgccaggct    120
ccgggaaacg agtgcgaact ggtgtctaca atcagttctg acgggtccac ctattacgct    180
gatagtgtca agggccgctt cactatctct caggacaacg cgaagaacac cgtttacttg    240
cagatggata gcgtgaagcc tgaagataca gcggtgtatt actgcgctgc cgactttatg    300
attgccatcc aggcaccggg ggcggggtgt tggggacagg gaactcaggt gactgtgtcc    360
tcc                                                                  363

```
<210> SEQ ID NO 96
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
caggttcaac tccaagagag tggtggcgga agcgtgcagg cgggcggttc tctgcgtctg      60
agttgcactg ccagcggatt taccttcgac gattccgaca tgggatggta cagacaggcc     120
cctggtaacg agtgcgaact cgtgagtact atcagctccg acggcaacac ctattacacc     180
gattctgtga agggcaggtt caccatctcc caggacaacg ctaagaacac tgtgtacctg     240
caaatgaata gcctgggacc cgaggacaca gcggtctatt actgcgcggc agagccgcgc     300
ggctattaca gcaactacgg cggtagacgc gagtgcaact actgggggca ggggacgcaa     360
gtgactgtct cctcc                                                       375

<210> SEQ ID NO 97
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
caagtgcagc ttcaggagtc cggggtggc agcgtccagg ctgggggcag cttgcgcctg       60
tcttgcgctg cgtctgggtt cagctttagc tcctacccta tgacctgggc tagacaggcc    120
cccggcaagg ggctggagtg ggtgagtaca atcgcctccg acggaggtag tacggcctac    180
gcagcgtccg tcgagggtcg cttcaccatc agccgggata acgctaagtc caccctgtac    240
cttcagctca attctctcaa aacggaggat accgccatgt actattgcac caagggatat    300
ggcgacggca ccccagctcc tggacagggc acacaggtca ccgttagctc c              351

<210> SEQ ID NO 98
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
caggtccagc ttcaggagtc tggcgggggc gcagtacagg caggggggttc tctgcgtctg     60 tcctgcgccg cgtccggctt tactttcagc aacgcacaca tgagttgggt gcgccaagcg    120
cccggcaagg gccgggaatg gatcagtagc atctacagtg gaggcagcac atggtacgcc    180
gactctgtta agggtcgttt tacgatctct cgtgacaact ccaagaacac tttgtacctc    240
cagctcaatt ctctcaagac cgaggacacc gcgatgtact attgtgccga gaacaggctg    300
cactactatt ccgacgatga ctctctcagg ggccagggaa ctcaagttac cgtgtccagc    360

<210> SEQ ID NO 99
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 99

```
caagtgcagc tccaagagag tggtggcggg ctggttcagc caggggcag cttgagactc    60 tcctgcgcag cttcaggctt taccttcgat gaccgtgaga tgaactggta tcgtcaggcc   120
ccaggcaacg agtgtgagct ggttagcacg atttcttccg acggttccac ctattacgcc   180
gactctgtga agggacgttt cactatctcc caggacaatg ccaagaacac cgtgtacctc   240
cagatggaca gcgtgaagcc ggaggatact gctgtgtatt actgcgctgc cgactttatg   300
atcgccatcc aggcccctgg cgcgggttgc tggggccagg gcactcaggt gaccgtgtct   360
tcc                                                                 363
```

<210> SEQ ID NO 100
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 100

```
caagtgcaac tgcaagagtc cggcggtgga tctgtgcagg ccggaggcag cctgcggctg    60
agctgtgtag cttccgggta tacctttagc tcatactgta tgggctggtt tcgtcaggcc   120
cccggtaagg agcgcgaggg cgtggccgct cttggtggag gctccaccta ttacgccgat   180
tccgtgaagg gcaggtttac tatctcccag gacaacgcga gaatacgct ctatctccag    240 atgaatagcc tgaagcccga ggatacagct atgtattact gtgctgccgc ttgggtagcc   300
tgcctggagt tcggtggctc ctggtacgat ctggcacggt acaaacattg ggggcagggc   360
acccaggtca ccgtgtctag c                                             381
```

<210> SEQ ID NO 101
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
caggtccagt tgcaggaatc tggggcggt tccgtacaag caggtggctc ccttcggttg     60
agctgtaccg catccggctt tactttcgac gatagcgata tgggctggta tcgtcaggcc   120 ccaggggcg agtgcgagct ggttacaatc tcctctgacg gcagtaccta ttacgcagac    180
tccgtcaagg gcaggttcac tatcagtcag gacaatgcaa agaacactgt gtatctccag   240
atgaactctc tgaagccaga agatactgcc gtgtattact cgctgcgga accgagaggc    300 tattactcta attatggcgg gcgtcgggag tgtaattatt ggggacaggg aacccaggtg   360
accgtgtcct cc                                                       372
```

<210> SEQ ID NO 102
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
caggtgcagc tccaggagag tggcggaggc tccgtgcagg ctgggggctc tctgcgtctg    60
```

```
agctgtgccg caagcggtag catttacagc tctgcctaca tcgggtggtt tcgtcaagcg    120
ccgggcaaaa agcgcgaagg cgtggccgga atctacacgc gcgatggctc caccgcttat    180
gctgacagcg ttaagggacg ttttacgatc agccaggact ctgccaaaaa gactgtgtat    240
ctccagatga actccctgaa acctgaggac acagccatgt attactgcgc cgctggccgc    300
cgtacaaaga gctatgttta catctttcgc cccgaagagt acaactactg gggccaggga    360
acccaagtga ctgtgtccag t                                              381
```

<210> SEQ ID NO 103
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
caggttcagt tgcaggagtc cggcggaggc agcgtgcagg ccggaggctc cttgcgcttg    60
tcctgtgcgg cttctggctt caccttctca tctgctcaca tgagttgggt gcgtcaggcc    120
ccagggaaag gtcgcgagtg gattgcctcc atctacagcg gtgggggcac tttttatgcg    180
gacagcgtga agggccgctt taccatcagc cgtgacaacg ctaagaacac cctgtatctc    240
caactcaatt ccctcaagac cgaggataca gcgatgtact attgtgcaac caaccgcctt    300
cactattact ccgacgatga cagcctgcgc ggacagggga cccaggtgac ggtgtccagc    360
```

<210> SEQ ID NO 104
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
caggtgcaac tccaggaaag tggcggaggc tcagtgcagg caggtggctc tctccgcctt    60
tcctgcgctg ccagcggatt caccttctct aacgctcaca tgagctgggt tcgtcaggct    120
cccggcaaag gccgtgaatg gattagctcc atctatagtg gcggaagtac ttggtacgca    180
gatagcgtca agggccgctt cactattagt cgggataact ccaagaacac tctgtacctc    240
cagctgaact cattgaaaac cgaggacacg gctatgtact attgtgctga aacaggctg    300 cactattact ccgacgatga ctctctgagg ggtcagggca cccaggtgac cgtcagctcc    360
```

<210> SEQ ID NO 105
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
caggtccaac tccaggagtc cggcggaggc agcgtgcagg ctggaggctc tctccgcctg    60
agctgcacag cttccagatt catcttcgat gactccgaca tgggctggta tcgccaggct    120
ccagggaacg agtgcgaact ggtgagcacc atctcttcag acggtagcac ctattacgcc    180
gacagtgtga agggcgcttt caccatcctc cgcgacaatg ctaaaaatac ggtgtatctc    240
cagatgaact ccctcaaacc ggaggacaca gctgtatatt actgtgctgc ggaaccacgg    300
```

```
ggctactata gcaactatgg tggaaggcgc gagtgcaact actggggtca gggcacacag    360
gtgacggttt cctcc                                                     375
```

<210> SEQ ID NO 106
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
caggtgcagc tccaggagag cggcggtggc tccgtgcagg ctggtggcag cctgaagctg    60
tcctgcaccg tgagtggctt cacagccgac gattctgata tgggctggta tcgccaaggc   120
cccggcaatg agtgcgagct ggtaaccatt agctcagacg gctctacata ctatgccgat   180
tctgttaagg gccgctttac tatctcacag gataatgcca agaacacagt gtacttgcag   240
atgaactctc tgaaaccgga agacacagct gtgtattact gtgctgcgga gcctagaggg   300
tattacagca attacggggg ccggagagag tgtaactatt gggggcaggg cacccaagtg   360
accgtttcct cc                                                       372
```

<210> SEQ ID NO 107
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
caggtccagc ttcaggaatc tgggggcggt ctcgtgcagc ccggcgggtc cctgcgtctg    60
tcttgtgctg cgagcggctt cacgttctca agtgcccaca tgagctgggt aaggcaggca   120
ccgggcaagg ggcgcgagtg gattgcaagc atctattcag gcggggggcac attctacgcc  180 gacagcgtga agggacgttt taatctccc agagataacg caaagaacac tctctacctc    240
caactcaact ccttgaaggc ggaagatact gcaatgtatt actgtgctac taaccgtctt   300
cattattact ctgacgatga ctccctgcgg gggcagggta caggtgac agtgagttcc    360
```

<210> SEQ ID NO 108
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

```
caggtgcagc tgcaagaatc tggtggaggg ctggtccagc ctgggggctc cctgcgcctc    60
tcatgtgtcg catctggctt caccttcagc aacgcccaca tgagctgggt tcgccaagcc   120
cctgggaagg gccgggagtg gatctccagt atctattccg gcggaagcac ttggtatgca   180
gacagcgtca aaggacggtt cactattcct cgtgataatt ctaagaacac cctgtacctt   240
cagctgaaca gcctgaagac cgaggacact gctatgtact attgtgctga gaatcgcctg   300
cattactata gcgacgatga cagtctgcgc ggacagggga cccaggtcac cgtgtcctct   360
```

<210> SEQ ID NO 109
<211> LENGTH: 360
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 109

```
caggttcagt tgcaggaatc aggaggcggt ctggtgcagc ctgggggctc tctgcgtctc    60
tcctgcgccg cttccggctt cacattctcc aacgcccaca tgagctgggt ccgccaggcc   120
cctgggaagg gccgcgagtg gatctccagt atctacagcg ggggctccac ttggtacgca   180
gacagcgtca aagggaggtt taccattagc cgtgacaatt caagaacac attgtatttg    240 cagctgaact ctcttaaaac cgaggacacc gccatgtact attgtgctga aacaggctc    300 cactattact cagacgatga ctcacttcgc gggcagggaa cccaggtcac cgtctcctct   360
```

<210> SEQ ID NO 110
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110

```
caagtccagc tccaggaaag cggcggtggc ctggtgcaac ctggcgggtc tctgcgcttg    60
tcatgcgctg cctccggctt caccttctca tcttacccta tgacctgggc gcgtcaggct   120
cccggcaagg gattggagtg ggtgtctact attgcctccg acggtggcag cacggcctac   180
gcagcgtctg tagaaggacg cttcacaatt agcagagaca cgcaaaatc tactttgtac    240 cttcagctca acagcctgaa gaccgaagac acagctatgt attactgcac aaaaggctac   300
ggggacggca cgccagcgcc tggacagggg acacaggtga ccgtatcttc t             351
```

<210> SEQ ID NO 111
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
caggtgcagt tgcaggaatc aggggggtggc tctgtgcagg ccggggggctc cctgcgtctg    60 tcctgtactg cgagcggctt caccttttgat gaccgcgaga tgaactggta tcgccaggct   120
ccggggaacg agtgcgaact cgtgtctaca attagctccg atggttcaac atactatgct   180
gattctgtca aagtcgcctt taccatctca caggacaacg ccaagaacac cgtctacctc    240
cagatggact ctgtgaagcc tgaagatacc gccgtatact attgcgccgc tgactttatg   300
attgccattc aggctccggg tgctggatgc tggggtcagg ggactcaggt gaccgtgtct   360
tca                                                                  363
```

<210> SEQ ID NO 112
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
caagtgcagt tgcaggaaag cggcggtggg tccgtgcaag ccggaggttc tctccgcctg    60
```

```
tcttgcactg cctcaggttt taccttcgac gattccgata tgggctggta caggcaggct    120
cccggcaatg agtgcgagct ggtgtctacg atctcaagtg atggctccac ctactatgcc    180
gatagcgtaa aaggaaggtt tactattagc caggataacg cgaagaacac ggtgtacctc    240
cagatgaaca gtctcaagcc ggaggatact gccgtgtatt actgtgctgc cgagccgcgt    300
ggctattact ccaactacgg tggcagacgt gaatgcaatt actggggaca gggtactcag    360
gttaccgtgt cctct                                                     375
```

<210> SEQ ID NO 113
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
caggttcaac ttcaggaatc cggggggcggt tccgtgcaag ccggggggtag cctgcgtctg    60 tcttgcgtgg ccagcggcta tacctcctgt atgggttggt tcggcaggc tcctgggaag    120 gagcgcgaag ccgtggcgac catctacaca cggggccgca gcatctatta cgctgacagt    180
gtgaagggcc gcttcaccat ctcccaggat aacgccaaga ataccctgta tctgcaaatg    240
aactccctga agcctgagga catcgccatg tattcctgcg cagctggagg gtactcatgg    300
tccgctgggt gcgagtttaa ttattggggc caaggaaccc aggtgaccgt ctcctca      357
```

<210> SEQ ID NO 114
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
caagtgcagc tccaggagtc tggcggggggc ctggttcagc ctggtgggtc cctgcgcctg    60
tcttgcacgg cttccggctt tagcttctcc tcatatccaa tgacctgggc acgccaggct    120
cctggtaagg gcctggagtg ggtctccacc atcgcctctg atggtgggtc aactgcctat    180
gctgcctccg tcgagggtag attcacaatc agcagagaca cgccaaatc cacgctgtac    240 ctgcaactca actccttgaa gaccgaggac acagctatgt attactgtac caaaggctac    300
ggcgacggca ctcctgctcc cggacagggg acccaggtga ctgtgtctag c             351
```

<210> SEQ ID NO 115
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
caggtccaac ttcaggaaag cggggggtgga ctggtacagc cagggggcag tctgcgcctg    60
tcctgtgccg caagcgggtt ttctttctcc agttaccccca tgacctgggc tcgccaagca    120
cctggaaagg gactgagtg ggtgtctact attgcgtcag atggtgggag tacggcttac    180
gccgcgagcg tggagggtcg ttttacgatc agtagggaca cgccaaaag cactctgtac    240 ctccagctta acagcctgaa gaccgaggac accgccatgt attactgtac caagggctac    300
```
ggagacggca ccctgcgcc ggggcaaggc acccaggtga ccgtaagttc a                351

<210> SEQ ID NO 116
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Gln Val Gln Leu Gln Glu Ser Gly Gly Gly Ser Val Leu Ala Gly Gly
1               5                   10                  15

Ser Leu Arg Leu Ser Cys Val Ala Ser Gly Tyr Gly Tyr Asn Tyr Ile
            20                  25                  30

Gly Trp Phe Arg Gln Thr Pro Gly Lys Glu Arg Glu Gly Val Ala Val
        35                  40                  45

Ile Tyr Thr Gly Gly Gly Asp Thr Tyr Tyr Ala Asp Ser Val Lys Gly
    50                  55                  60

Arg Phe Thr Ala Ser Arg Asp Asn Ala Lys Ser Thr Leu Tyr Leu Gln
65                  70                  75                  80

Met Asn Ser Leu Glu Pro Glu Asp Thr Ala Met Tyr Tyr Gly Val Ala
                85                  90                  95

Arg Tyr Cys Val Gly Ser Val Tyr Ala Cys Leu Arg Gly Gly His Asp
            100                 105                 110

Glu Tyr Ala His Trp Gly Gln Gly Thr Gln Val Thr Val Ser Ser
        115                 120                 125
```

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Tyr Gly Tyr Asn Tyr Ile Gly
1               5
```

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Val Ile Tyr Thr Gly Gly Gly Asp Thr Tyr Tyr Ala Asp Ser Val Lys
1               5                   10                  15

Gly
```

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Val Tyr Ala Cys Leu Arg Gly Gly His Asp Glu Tyr Ala His
1               5                   10                  15

<210> SEQ ID NO 120
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Gln Glu Ser Gly Gly Gly Ser Val Gln Pro Gly Gly
1               5                   10                  15

Ser Leu Arg Leu Ser Cys Ala Ala Ser Gly Ser Thr Tyr Ala Asn Tyr
                20                  25                  30

Leu Met Gly Trp Phe Arg Gln Ala Pro Gly Lys Glu Arg Glu Gly Val
            35                  40                  45

Ala Ala Ile Tyr Ser Gly Gly Gly Ser Thr Tyr Tyr Ala Asp Ser Val
        50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Ala Ser Ala Val Lys Gly Asp Lys Gly Asp Ile Val Val Val
            100                 105                 110

Val Thr Gly Thr Gln Arg Met Glu Tyr Asp Tyr Trp Gly His Gly Thr
        115                 120                 125

Gln Val Thr Val Ser Ser
    130

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Thr Tyr Ala Asn Tyr Leu Met Gly
1               5

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Ile Tyr Ser Gly Gly Gly Ser Thr Tyr Tyr Ala Asp Ser Val Lys
1               5                   10                  15

Gly

<210> SEQ ID NO 123
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 123

Ala Ser Ala Val Lys Gly Asp Lys Gly Asp Ile Val Val Val Thr
1               5                   10                  15

Gly Thr Gln Arg Met Glu Tyr Asp Tyr
            20                  25

<210> SEQ ID NO 124
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gln Val Gln Leu Gln Glu Ser Gly Gly Gly Ser Val Gln Ala Gly Ala
1               5                   10                  15

Ser Leu Arg Leu Ser Cys Ser Val Ser Gly Phe Thr Phe Asp Glu Ser
            20                  25                  30

Val Met Ser Trp Leu Arg Gln Gly Pro Gly Asn Glu Cys Asp Ala Val
        35                  40                  45

Ala Ile Ile Ser Ser Asp Asp Asn Thr Tyr Tyr Asp Ser Val Lys
    50                  55                  60

Gly Arg Phe Thr Ile Ser Glu Asp Asn Ala Lys Asn Met Val Tyr Leu
65                  70                  75                  80

Gln Met Asn Ser Leu Lys Pro Glu Asp Thr Ala Val Tyr Tyr Cys Ala
                85                  90                  95

Ala Arg Arg Arg Arg Pro Val Tyr Asp Ser Asp Tyr Glu Leu Arg Pro
            100                 105                 110

Arg Pro Leu Cys Gly Asp Phe Gly Val Trp Gly Gln Gly Thr Gln Val
        115                 120                 125

Thr Val Ser Ser
    130

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Phe Thr Phe Asp Glu Ser Val Met Ser
1               5

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ile Ile Ser Ser Asp Asp Asn Thr Tyr Tyr Asp Ser Val Lys Gly
1               5                   10                  15

<210> SEQ ID NO 127
<211> LENGTH: 24
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 127

Arg Arg Arg Arg Pro Val Tyr Asp Ser Asp Tyr Glu Leu Arg Pro Arg
1               5                   10                  15

Pro Leu Cys Gly Asp Phe Gly Val
            20

<210> SEQ ID NO 128
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Val Gln Leu Gln Glu Ser Gly Gly Gly Ser Val Gln Ala Gly Gly
1               5                   10                  15

Ser Leu Arg Leu Ser Cys Ile Gly Ser Gly Leu Pro Phe Asp Glu Asp
            20                  25                  30

Asp Met Gly Trp Tyr Arg Gln Ala Pro Gly Asn Glu Cys Glu Leu Val
        35                  40                  45

Ser Ser Ile Ser Ser Asp Gly Thr Ala Tyr Tyr Ala Asp Ser Val Lys
50                  55                  60

Gly Arg Phe Thr Ile Ser Arg Asp Asn Ala Lys Asn Thr Val Leu Leu
65                  70                  75                  80

Gln Met Asn Ser Leu Lys Pro Glu Asp Thr Ala Val Tyr Tyr Cys Ala
                85                  90                  95

Ala Gly Val His Arg Gln Phe Gly Gly Ser Ser Ser Cys Gly Asp Ala
            100                 105                 110

Phe Tyr Gly Met Asp Tyr Trp Gly Lys Gly Thr Gln Val Thr Val Ser
        115                 120                 125

Ser

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Leu Pro Phe Asp Glu Asp Asp Met Gly
1               5

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Ile Ser Ser Asp Gly Thr Ala Tyr Tyr Ala Asp Ser Val Lys Gly
1               5                   10                  15
```

```
<210> SEQ ID NO 131
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Val His Arg Gln Phe Gly Gly Ser Ser Cys Gly Asp Ala Phe
1               5                   10                  15

Tyr Gly Met Asp Tyr
            20

<210> SEQ ID NO 132
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Gln Glu Ser Gly Gly Ser Val Gln Ala Gly Gly
1               5                   10                  15

Ser Leu Arg Leu Ser Cys Val Ala Ser Gly Asp Val Tyr Gly Arg Asn
                20                  25                  30

Ser Met Ala Trp Phe Arg Gln Ala Pro Gly Lys Glu Arg Glu Gly Val
            35                  40                  45

Ala Val Gly Tyr Ser Val Val Thr Thr Thr Tyr Ala Asp Ser Val
        50                  55                  60

Lys Gly Arg Phe Thr Ile Ser Glu Asp Asn Asp Lys Asn Thr Val Tyr
65                  70                  75                  80

Leu Glu Met Asn Ser Leu Lys Pro Glu Asp Thr Ala Met Tyr Tyr Cys
                85                  90                  95

Ala Ala Asp Gly Asn Leu Trp Arg Gly Leu Arg Pro Ser Glu Tyr Thr
            100                 105                 110

Tyr Trp Gly Gln Gly Thr Gln Val Thr Val Ser Ser
        115                 120

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asp Val Tyr Gly Arg Asn Ser Met Ala
1               5

<210> SEQ ID NO 134
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Val Gly Tyr Ser Val Val Thr Thr Tyr Tyr Ala Asp Ser Val Lys
1               5                   10                  15
```

Gly

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Gly Asn Leu Trp Arg Gly Leu Arg Pro Ser Glu Tyr Thr Tyr
1               5                   10                  15

<210> SEQ ID NO 136
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Gln Glu Ser Gly Gly Ser Val Gln Ala Gly Gly
1               5                   10                  15

Ser Leu Arg Leu Ser Cys Ala Thr Ser Gly Phe Pro Tyr Ser Arg Tyr
            20                  25                  30

Cys Met Gly Trp Phe Arg Gln Ala Pro Gly Lys Glu Arg Glu Gly Val
        35                  40                  45

Ala Ala Ile Glu Pro Asp Gly Ser Thr Ser Tyr Ala Asp Ser Val Lys
    50                  55                  60

Gly Arg Phe Thr Ile Ser Gln Asp Asn Ala Val Asn Thr Leu Tyr Leu
65                  70                  75                  80

Gln Met Asn Asn Leu Lys Pro Glu Asp Thr Ala Met Tyr Tyr Cys Ala
                85                  90                  95

Ala Asp Glu Arg Cys Phe Tyr Leu Lys Asp Tyr Asp Leu Arg Arg Pro
            100                 105                 110

Ala Gln Tyr Arg Tyr Trp Gly Gln Gly Thr Gln Val Thr Val Ser Ser
        115                 120                 125

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Phe Pro Tyr Ser Arg Tyr Cys Met Gly
1               5

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ile Glu Pro Asp Gly Ser Thr Ser Tyr Ala Asp Ser Val Lys Gly
1               5                   10                  15

<210> SEQ ID NO 139
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Glu Arg Cys Phe Tyr Leu Lys Asp Tyr Asp Leu Arg Arg Pro Ala
1               5                   10                  15

Gln Tyr Arg Tyr
            20

<210> SEQ ID NO 140
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Val Gln Leu Gln Glu Ser Gly Gly Gly Leu Val Gln Pro Gly Gly
1               5                   10                  15

Ser Leu Arg Leu Ser Cys Thr Val Ser Gly Phe Thr Phe Asp Glu Ser
            20                  25                  30

Asp Met Gly Trp Leu Arg Gln Asn Pro Gly Asn Glu Cys Gly Val Val
        35                  40                  45

Ser Val Ile Thr Ser Asp Asp Asn Pro Tyr Tyr Asp Asp Ser Val Lys
    50                  55                  60

Gly Arg Phe Thr Ile Ser Glu Asp Asn Ala Lys Asn Met Val Tyr Leu
65                  70                  75                  80

Gln Met Asn Ser Leu Lys Pro Glu Asp Thr Gly Val Tyr Tyr Cys Ala
                85                  90                  95

Thr Arg Ser Arg Gln Pro Val Tyr Ser Arg Asp Tyr Glu Leu Arg Pro
            100                 105                 110

Arg Pro Leu Cys Gly Asp Phe Gly Val Trp Gly Gln Gly Thr Gln Val
        115                 120                 125

Thr Val Ser Ser
    130

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Phe Thr Phe Asp Glu Ser Asp Met Gly
1               5

<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Val Ile Thr Ser Asp Asp Asn Pro Tyr Tyr Asp Asp Ser Val Lys Gly
1               5                   10                  15
```

<210> SEQ ID NO 143
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

```
Arg Ser Arg Gln Pro Val Tyr Ser Arg Asp Tyr Glu Leu Arg Pro Arg
1               5                   10                  15

Pro Leu Cys Gly Asp Phe Gly Val
            20
```

<210> SEQ ID NO 144
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

```
Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Phe
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Asn Thr Val Tyr Leu
65                  70                  75                  80

Gln Met Asn Arg Leu Lys Pro Glu Asp Thr Gly Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125
```

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

```
Phe Thr Phe Asp Asp Phe Asp Met Gly
1               5
```

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 146

Thr Ile Ser Asp Asp Gly Ser Thr Tyr Tyr Ala Asp Ser Val Lys Gly
1               5                   10                  15

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Glu Gly Ala Leu Gly Ser Lys Thr Asn Cys Gly Trp Val Gly Asn Phe
1               5                   10                  15

Gly Tyr

<210> SEQ ID NO 148
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gln Val Gln Leu Gln Glu Ser Gly Gly Ser Val Gln Ala Gly Gly
1               5                   10                  15

Ser Leu Arg Leu Ser Cys Ala Ala Ser Gly Phe Thr Phe Asp Asp Phe
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Phe Thr Phe Asp Asp Phe Asp Met Gly
1               5

<210> SEQ ID NO 150
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 150

Thr Ile Ser Asp Asp Gly Ser Thr Tyr Tyr Ala Asp Ser Val Lys Gly
1               5                   10                  15

<210> SEQ ID NO 151
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Glu Gly Ala Leu Gly Ser Lys Thr Asn Cys Gly Trp Val Gly Asn Phe
1               5                   10                  15

Gly Tyr

<210> SEQ ID NO 152
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Asp Asp Phe
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Ser Thr Val Tyr Leu
65                  70                  75                  80

Gln Met Asn Arg Leu Lys Pro Glu Asp Thr Gly Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Phe Thr Phe Asp Asp Phe Asp Met Gly
1               5

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 154

Thr Ile Ser Asp Asp Gly Ser Thr Tyr Tyr Ala Asp Ser Val Lys Gly
1               5                   10                  15

<210> SEQ ID NO 155
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Glu Gly Ala Leu Gly Ser Lys Thr Asn Cys Gly Trp Val Gly Asn Phe
1               5                   10                  15

Gly Tyr

<210> SEQ ID NO 156
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Thr Phe Ser Asp Arg
            20                  25                  30

Asp Met Gly Trp Tyr Arg Gln Ala Pro Gly Asn Glu Cys Glu Arg Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Phe Thr Phe Ser Asp Arg Asp Met Gly
1               5

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 158

Thr Ile Ser Asp Asp Gly Ser Thr Tyr Tyr Ala Asp Ser Val Lys Gly
1               5                   10                  15

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Glu Gly Ala Leu Gly Ser Lys Thr Asn Cys Gly Trp Val Gly Asn Phe
1               5                   10                  15

Gly Tyr

<210> SEQ ID NO 160
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Gln Glu Ser Gly Gly Ser Val Leu Ala Gly Gly
1               5                   10                  15

Ser Leu Arg Leu Ser Cys Val Ala Ser Gly Tyr Gly Tyr Asn Tyr Ile
                20                  25                  30

Gly Trp Phe Arg Gln Thr Pro Gly Lys Glu Arg Glu Gly Val Ala Val
            35                  40                  45

Ile Tyr Ile Gly Gly Gly Asp Thr Tyr Tyr Ala Asp Ser Val Lys Gly
        50                  55                  60

Arg Phe Thr Ala Ser Arg Asp Asn Ala Lys Ser Thr Leu Tyr Leu Gln
65                  70                  75                  80

Met Asn Ser Leu Glu Pro Glu Asp Thr Ala Met Tyr Tyr Cys Val Ala
                85                  90                  95

Arg Tyr Cys Val Gly Ser Val Tyr Ala Cys Leu Arg Gly Gly His Asp
            100                 105                 110

Glu Tyr Ala His Trp Gly Gln Gly Thr Gln Val Thr Val Ser Ser
        115                 120                 125

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Tyr Gly Tyr Asn Tyr Ile Gly
1               5

<210> SEQ ID NO 162
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 162

Val Ile Tyr Ile Gly Gly Gly Asp Thr Tyr Tyr Ala Asp Ser Val Lys
1               5                   10                  15

Gly

<210> SEQ ID NO 163
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Arg Tyr Cys Val Gly Ser Val Tyr Ala Cys Leu Arg Gly Gly His Asp
1               5                   10                  15

Glu Tyr Ala His
            20

<210> SEQ ID NO 164
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gln Val Gln Leu Gln Glu Ser Gly Gly Gly Ser Val Leu Ala Gly Gly
1               5                   10                  15

Ser Leu Arg Leu Ser Cys Val Ala Ser Gly Tyr Gly Tyr Asn Tyr Ile
            20                  25                  30

Gly Trp Phe Arg Gln Thr Pro Gly Lys Glu Arg Glu Gly Val Ala Val
        35                  40                  45

Ile Tyr Thr Gly Gly Gly Asp Thr Tyr Tyr Ala Asp Ser Val Lys Gly
    50                  55                  60

Arg Phe Thr Ala Ser Arg Asp Asn Ala Lys Ser Thr Leu Tyr Leu Gln
65                  70                  75                  80

Met Asn Ser Leu Glu Pro Glu Asp Thr Ala Met Tyr Tyr Cys Val Ala
                85                  90                  95

Arg Tyr Cys Val Gly Ser Val Tyr Ala Cys Leu Arg Gly Gly His Asp
            100                 105                 110

Glu Tyr Ala His Trp Gly Gln Gly Thr Gln Val Thr Val Ser Ser
        115                 120                 125

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Tyr Gly Tyr Asn Tyr Ile Gly
1               5

<210> SEQ ID NO 166
<211> LENGTH: 17
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 166

Val Ile Tyr Thr Gly Gly Asp Thr Tyr Tyr Ala Asp Ser Val Lys
1               5                   10                  15

Gly

<210> SEQ ID NO 167
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Tyr Cys Val Gly Ser Val Tyr Ala Cys Leu Arg Gly Gly His Asp
1               5                   10                  15

Glu Tyr Ala His
            20

<210> SEQ ID NO 168
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Val Gln Leu Gln Glu Ser Gly Gly Gly Ser Val Gln Ala Gly Gly
1               5                   10                  15

Ser Leu Arg Leu Ser Cys Ala Ala Ser Gly Phe Thr Phe Asp Asp Phe
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asn Ser Val Lys
    50                  55                  60

Gly Arg Ser Ser Ile Ser Arg Asp Asn Ala Lys Asn Met Val Tyr Leu
65                  70                  75                  80

Gln Met Asn Ser Leu Lys Pro Glu Asp Thr Ala Val Tyr Tyr Cys Ala
                85                  90                  95

Ala Glu Gly Ala Leu Gly Ser Lys Thr Asn Cys Gly Trp Val Gly Asn
            100                 105                 110

Phe Gly Tyr Trp Gly Gln Gly Thr Gln Val Thr Val Ser Ser
        115                 120                 125

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Phe Thr Phe Asp Asp Phe Asp Met Gly
1               5

<210> SEQ ID NO 170
<211> LENGTH: 16

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Thr Ile Ser Asp Asp Gly Ser Thr Tyr Tyr Ala Asn Ser Val Lys Gly
1               5                   10                  15

<210> SEQ ID NO 171
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Glu Gly Ala Leu Gly Ser Lys Thr Asn Cys Gly Trp Val Gly Asn Phe
1               5                   10                  15

Gly Tyr

<210> SEQ ID NO 172
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gln Val Gln Leu Gln Glu Ser Gly Gly Gly Ser Val Gln Ala Gly Gly
1               5                   10                  15

Ser Leu Arg Leu Ser Cys Thr Ala Ser Gly Phe Thr Phe Asp Asp Phe
            20                  25                  30

Asp Met Gly Trp Tyr Arg Gln Ala Pro Gly Asn Glu Cys Glu Leu Val
        35                  40                  45

Ser Thr Ile Ser Asp Asp Gly Ser Thr Tyr Tyr Ala Asp Ser Val Lys
    50                  55                  60

Gly Arg Ser Ser Ile Ser Arg Asp Asn Ala Lys Asn Thr Val Tyr Leu
65                  70                  75                  80

Gln Met Asn Arg Leu Lys Pro Glu Asp Thr Gly Val Tyr Tyr Cys Ala
                85                  90                  95

Ala Glu Gly Ala Leu Gly Ser Lys Met Asn Cys Gly Trp Val Gly Asn
            100                 105                 110

Phe Gly Tyr Trp Gly Gln Gly Thr Gln Val Thr Val Ser Ser
        115                 120                 125

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Phe Thr Phe Asp Asp Phe Asp Met Gly
1               5

<210> SEQ ID NO 174
<211> LENGTH: 16

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Thr Ile Ser Asp Asp Gly Ser Thr Tyr Tyr Ala Asp Ser Val Lys Gly
1               5                   10                  15

<210> SEQ ID NO 175
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Glu Gly Ala Leu Gly Ser Lys Met Asn Cys Gly Trp Val Gly Asn Phe
1               5                   10                  15

Gly Tyr

<210> SEQ ID NO 176
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176
caggtgcaac tccaggagtc cggcgggggc tccgtgctgg ctggcggatc tttgaggctg     60
tcttgcgtgg cttctggcta tggctataat tacatcggct ggttccgtca gacacccggc    120
aaggagcgcg aagggtggc ggtcatttac acaggggtg gggacactta ttacgccgac      180
tccgtcaagg gtaggtttac cgctagtcgc gataatgcca aaagtacgct gtacctgcaa    240
atgaacagct tggagccaga ggacaccgcc atgtattacg gagtggctcg ctactgtgtg    300
ggcagtgtgt acgcttgcct gcgcggaggc cacgacgagt acgcacactg gggccaggga    360
acccaggtga cagtgtctag c                                              381

<210> SEQ ID NO 177
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
caggtgcagc tccaggagtc tgggggtggc agcgtccagc aggtggctc attgagactg       60 tcttgtgctg catctggctc cacctacgct aattacctga tgggatggtt caggcaggcc    120
cctggtaagg agcgtgaggg cgtggccgct atctattctg gcggtgggtc cacctactat    180
gctgactccg tcaagggacg cttcactatt tctcaagaca atgccaagaa cactttgtac    240
ttgcaaatga actcactcaa acctgaggac accgcgatgt actattgcgc agcggcatcc    300
gcagtgaagg gagacaaagg ggatatcgtg gtagttgtga ccggcaccca gcgtatggag    360
tacgactact ggggacatgg cacccaggtg acagttagct cc                       402

<210> SEQ ID NO 178

```
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
caggtacagt tgcaggagag tggtgggggt tccgtccagg ccggtgcctc tcttcgcctc    60
agttgtagcg tgagcggttt cacgttcgac gagtcagtga tgtcctggtt gcgccagggt   120
cccggcaatg agtgcgacgc ggtcgctatt atcagctccg atgacaacac ctattacgac   180
gatagcgtga aaggccgctt taccatctcc gaggacaacg ccaaaaacat ggtgtatctg   240
caaatgaact cactgaagcc ggaagacacc gcagtgtact attgcgccgc gcgtcggcgc   300
agacctgtgt acgattccga ttatgaactc cggccacgtc cgctgtgtgg cgatttcggc   360
gtgtggggcc aggggaccca ggtgacggtc tcctcc                             396

<210> SEQ ID NO 179
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
caggtgcagc tccaggaatc tggcgggggc tctgtgcagg ctggtggctc ccttcgcctg    60
tcctgtattg gctccggtct tcctttcgac gaggatgaca tgggctggta tcgccaggcc   120
cctgggaatg agtgtgaatt ggtcagctca atctccagtg acggcaccgc ctattacgcc   180
gattccgtca agggacgctt cactatctcc agagacaacg ccaagaacac tgtgctgttg   240
cagatgaact ccctgaagcc cgaggatacc gctgtctatt actgcgcagc cggggtccac   300
agacagttcg gcggttccag ttcctgcggc gacgccttct acggcatgga ttactggggc   360
aagggaactc aggtcacagt gtcttcc                                       387

<210> SEQ ID NO 180
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
caggttcagc ttcaggagtc cggcggggc tccgtacagg caggggctc actgcgtctt     60 tcctgtgtgg cgagtggcga cgtgtatggc cgtaacagca tggcttggtt ccggcaggca   120
cctggaaagg aacgcgaggg cgttgcagtt gggtattccg tagtgacaac cacttactat   180
gccgacagtg tgaagggccg gtttacgatc tcagaggaca cgataaaaa cacagtgtac    240 ctggagatga actccctgaa gccggaagac actgctatgt attactgcgc tgccgatggc   300
aacctgtggc gcggactcag gccctccgag tacacttatt ggggtcaggg cacccaggtg   360
accgtttcaa gt                                                       372

<210> SEQ ID NO 181
<211> LENGTH: 384
<212> TYPE: DNA
<213> ORGANISM: Artificial Sequence
<220> FEATURE:
```

<223> OTHER INFORMATION: Description of Artificial Sequence: Synthetic
     polynucleotide

<400> SEQUENCE: 181

| caggtccagc ttcaggagtc aggtggcggt agtgtccagg caggcggtag cctgcgcctt | 60 |
| agctgtgcta catccggctt cccttactca cgctattgta tgggctggtt caggcaagct | 120 |
| cccggtaaag agcgcgaggg agtggcagcc atcgagcctg acgggagcac atcttatgct | 180 |
| gactctgtaa aggggcgttt caccatctct caggacaacg ccgttaatac actgtacttg | 240 |
| caaatgaata acctgaagcc cgaggacaca gctatgtatt actgcgcagc cgacgagcgt | 300 |
| tgcttctatt tgaaggacta tgacctcaga aggccagccc agtaccgcta ctgggggcag | 360 |
| ggcacccagg ttaccgtgtc atct | 384 |

<210> SEQ ID NO 182
<211> LENGTH: 396
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 182

| caggtgcagt tgcaggagag tggcggtggc ctcgtgcagc ctggcggaag cctccgtctg | 60 |
| agctgcactg tgtccggctt cactttcgac gagagcgaca tgggctggct gaggcagaac | 120 |
| cctggtaacg agtgcggcgt tgtgagtgtc atcacgtctg atgacaaccc atactatgat | 180 |
| gacagcgtca agggccgctt tactatctcc gaggataacg ccaagaacat ggtgtacctc | 240 |
| cagatgaact cactgaagcc cgaggatacc ggcgtttatt actgtgcaac caggagccgt | 300 |
| cagcctgtgt actcacgcga ttacgagctg cggccccgcc ccctctgtgg agactttggt | 360 |
| gtgtggggcc agggcaccca ggtgactgtt tccagc | 396 |

<210> SEQ ID NO 183
<211> LENGTH: 378
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 183

| caggtgcagt tgcaggagag tggaggggggc tcagtgcagg ctggcgggtc cttgcgtctg | 60 |
| tcttgcaccg cctctggctt caccttcgat gacttcgata tgggttggta tcgccaggct | 120 |
| ccagggaacg agtgcgaatt ggtcagcact atcagcgacg atggctcaac atattacgcc | 180 |
| gactctgtga agggacggtc tagcattagc cgggacaacg caaagaacac cgtctatctc | 240 |
| cagatgaacc gcttgaagcc tgaggatacc ggagtctatt actgcgccgc tgagggcgcg | 300 |
| ttgggctcca agactaattg tggctgggtg ggcaacttcg atattgggg ccagggaaca | 360 |
| caggttaccg tttccagc | 378 |

<210> SEQ ID NO 184
<211> LENGTH: 378
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 184

```
caggtgcagt tgcaggagtc tggaggcggt tccgttcagg ccgggggctc tctgcgcctg      60
tcctgcgctg cctccgggtt tacatttgac gatttcgata tgggctggta tcgccaggcc     120
cctggcaacg agtgcgaact ggtgtctact atctccgatg acggctcaac ctactatgca     180
gactccgtaa agggcagatc cagcatctcc cgcgacaatg ccaaaaacac tgtgtacctc     240
cagatgaact ccctcaagcc tgaggatacg gcggtgtact attgtgctgc cgagggtgcg     300
ctcggtagca agactaattg cggctgggtg ggcaacttcg ggtactgggg tcaggggacc     360
caggtaaccg tgtcttct                                                   378
```

<210> SEQ ID NO 185
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185

```
caggtgcagt tgcaggaaag cggtgggggc ctggtgcagc ccggaggcag cctgcgcttg      60
agctgcgctg cctctggctt cacattcgat gacttcgata tgggctggta tcgtcaagca     120
cccggaaacg agtgcgagct ggtgagtaca atcagtgatg acggatctac ctactatgcc     180
gacagcgtca agggaagatc cagcatcagt cgcgacaacg ccaagagcac cgtttacctc     240
cagatgaacc gcctcaagcc tgaggacaca ggagtctatt actgtgctgc ggaggggggcc     300 ttgggcagca agactaactg tggatgggtg ggaaacttcg ggtattgggg tcaggagtaca     360 caggtcacag tgtcttca                                                   378
```

<210> SEQ ID NO 186
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 186

```
caagttcagc ttcaggaaag tggggcgggg ctggtgcagc caggggggttc cctgaagctg      60 agctgcgctg cctctgggtt tacattctct gatcgcgaca tgggctggta tcgccaagcg     120
ccgggcaatg aatgcgaaag agtgagtact atttctgacg atggttctac ttactatgct     180
gactccgtga agggccgtag ctccatttcc agggacaacg cgaagaacac cgtataacctc     240 cagatgaact ctctgaagcc cgaggacacc gctgtgtatt actgcgctgc cgagggggct     300
ctcggctcaa agaccaactg cggatgggtc ggtaacttcg gctactgggg ccagggcacc     360
caagtgacag tctcctcc                                                   378
```

<210> SEQ ID NO 187
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187

```
caggtccagt tgcaggagag cgggggtgga agcgtcctcg ccggagggag cctccgtttg      60
agctgcgtcg cctcaggcta cggctacaat tacatcggat ggttcagaca gacgcctggt     120
```

```
aaagagcggg aaggcgtcgc cgtgatttat atcggtggcg gagacaccta ttacgctgac    180
tcagtgaagg ggcgtttcac cgcaagccgg gacaacgcta agagcaccct gtacctccag    240
atgaactctc tcgaacctga ggacactgca atgtattact gcgtggctcg ttactgcgtc    300
gggagtgtct acgcctgcct gaggggcggg catgatgagt atgcccactg gggacaagga    360
acacaggtga ctgtctccag t                                              381

<210> SEQ ID NO 188
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
caggttcagc tccaggagtc tggtggcggt tccgtgctgg ccggggggctc tctgcgcctg    60 tcttgtgtcg cctcagggta cggctataac tacattggct ggttcagaca dacccctggg    120
aaagagcggg agggtgtggc tgtcatttac accggcggag cgacaccta ctatgccgat     180 tcagttaagg gcaggtttac cgcgagccgt gacaacgcga agtctactct gtacctgcaa    240
atgaacagcc tggaacctga ggatactgcg atgtactatt gtgtggcccg gtactgcgta    300
ggctcagtgt atgcctgcct gcgcgggggt cacgacgagt acgcacactg gggacaggga    360
actcaggtca ccgtgtctag c                                              381

<210> SEQ ID NO 189
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189
caggtgcaac tccaggagtc cggcgggggc tccgtccaag ctggtggctc actgaggctt    60
agctgtgctg cctccggctt tacttttcgac gatttcgaca tgggttggta tcgccaggct   120
ccgggcaatg agtgcgagct ggtctctacc atttccgatg acggctctac ctactatgcc   180
aacagtgtta agggtaggtc ttccatctcc cgcgacaacg ctaagaatat ggtgtacttg   240
cagatgaact ctctgaagcc tgaggacact gctgtctact attgcgctgc cgaaggtgcc   300
ctgggctcaa agactaattg cggctgggtc ggtaactttg gctactgggg tcagggggact  360 caggtgaccg tcagctcc                                                 378

<210> SEQ ID NO 190
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
caggtccagt tgcaggaaag cggcgggggc tctgttcagg caggcggaag ccttcgtctg   60
tcctgtactg ccagtggttt cacctttgat gactttgaca tgggctggta tcggcaagcc  120
cccggaaacg agtgcgagct ggtatccacc atttccgatg acgggtccac gtactatgct  180
gatagcgtga agggcaggtc ttccatcagc cgggacaacg ccaagaacac agtgtatttg  240
```
cagatgaacc gcctcaagcc agaagacacc ggggtatatt actgtgcagc ggaaggtgcc    300
ctgggtagca agatgaactg cggatgggtg ggtaattttg gatactgggg ccagggcacg    360
caggttacag tgtccagc                                                  378

<210> SEQ ID NO 191
<211> LENGTH: 369
<212> TYPE: PRT
<213> ORGANISM: Homo sapiens

<400> SEQUENCE: 191

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Val Val Ile Ser Val Gly Ser Met Gly Leu
            260                 265                 270

Ile Ile Ser Leu Leu Cys Val Tyr Phe Trp Leu Glu Arg Thr Met Pro
        275                 280                 285

Arg Ile Pro Thr Leu Lys Asn Leu Glu Asp Leu Val Thr Glu Tyr His
    290                 295                 300

Gly Asn Phe Ser Ala Trp Ser Gly Val Ser Lys Gly Leu Ala Glu Ser
305                 310                 315                 320

Leu Gln Pro Asp Tyr Ser Glu Arg Leu Cys Leu Val Ser Glu Ile Pro
                325                 330                 335

Pro Lys Gly Gly Ala Leu Gly Glu Gly Pro Gly Ala Ser Pro Cys Asn

```
                340                 345                 350
Gln His Ser Pro Tyr Trp Ala Pro Pro Cys Tyr Thr Leu Lys Pro Glu
        355                 360                 365
Thr
```

<210> SEQ ID NO 192
<211> LENGTH: 240
<212> TYPE: PRT
<213> ORGANISM: Homo sapiens

<400> SEQUENCE: 192

```
Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
                20                  25                  30

Leu Pro Leu Pro Glu Val Gln Cys Phe Val Phe Asn Val Glu Tyr Met
            35                  40                  45

Asn Cys Thr Trp Asn Ser Ser Glu Pro Gln Pro Thr Asn Leu Thr
        50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240
```

<210> SEQ ID NO 193
<211> LENGTH: 369
<212> TYPE: PRT
<213> ORGANISM: Mus musculus

<400> SEQUENCE: 193

```
Met Leu Lys Leu Leu Leu Ser Pro Arg Ser Phe Leu Val Leu Gln Leu
1               5                   10                  15

Leu Leu Leu Arg Ala Gly Trp Ser Ser Lys Val Leu Met Ser Ser Ala
                20                  25                  30

Asn Glu Asp Ile Lys Ala Asp Leu Ile Leu Thr Ser Thr Ala Pro Glu
            35                  40                  45

His Leu Ser Ala Pro Thr Leu Pro Leu Pro Glu Val Gln Cys Phe Val
        50                  55                  60
```

Phe Asn Ile Glu Tyr Met Asn Cys Thr Trp Asn Ser Ser Glu Pro
65                  70                  75                  80

Gln Ala Thr Asn Leu Thr Leu His Tyr Arg Tyr Lys Val Ser Asp Asn
            85                  90                  95

Asn Thr Phe Gln Glu Cys Ser His Tyr Leu Phe Ser Lys Glu Ile Thr
                100                 105                 110

Ser Gly Cys Gln Ile Gln Lys Glu Asp Ile Gln Leu Tyr Gln Thr Phe
            115                 120                 125

Val Val Gln Leu Gln Asp Pro Gln Lys Pro Gln Arg Arg Ala Val Gln
130                 135                 140

Lys Leu Asn Leu Gln Asn Leu Val Ile Pro Arg Ala Pro Glu Asn Leu
145                 150                 155                 160

Thr Leu Ser Asn Leu Ser Glu Ser Gln Leu Glu Leu Arg Trp Lys Ser
            165                 170                 175

Arg His Ile Lys Glu Arg Cys Leu Gln Tyr Leu Val Gln Tyr Arg Ser
                180                 185                 190

Asn Arg Asp Arg Ser Trp Thr Glu Leu Ile Val Asn His Glu Pro Arg
            195                 200                 205

Phe Ser Leu Pro Ser Val Asp Glu Leu Lys Arg Tyr Thr Phe Arg Val
210                 215                 220

Arg Ser Arg Tyr Asn Pro Ile Cys Gly Ser Ser Gln Gln Trp Ser Lys
225                 230                 235                 240

Trp Ser Gln Pro Val His Trp Gly Ser His Thr Val Glu Glu Asn Pro
            245                 250                 255

Ser Leu Phe Ala Leu Glu Ala Val Leu Ile Pro Val Gly Thr Met Gly
                260                 265                 270

Leu Ile Ile Thr Leu Ile Phe Val Tyr Cys Trp Leu Glu Arg Met Pro
            275                 280                 285

Pro Ile Pro Pro Ile Lys Asn Leu Glu Asp Leu Val Thr Glu Tyr Gln
290                 295                 300

Gly Asn Phe Ser Ala Trp Ser Gly Val Ser Lys Gly Leu Thr Glu Ser
305                 310                 315                 320

Leu Gln Pro Asp Tyr Ser Glu Arg Phe Cys His Val Ser Glu Ile Pro
            325                 330                 335

Pro Lys Gly Gly Ala Leu Gly Glu Gly Pro Gly Gly Ser Pro Cys Ser
                340                 345                 350

Leu His Ser Pro Tyr Trp Pro Pro Cys Tyr Ser Leu Lys Pro Glu
            355                 360                 365

Ala

<210> SEQ ID NO 194
<211> LENGTH: 241
<212> TYPE: PRT
<213> ORGANISM: Mus musculus

<400> SEQUENCE: 194

Trp Ser Ser Lys Val Leu Met Ser Ser Ala Asn Glu Asp Ile Lys Ala
1               5                   10                  15

Asp Leu Ile Leu Thr Ser Thr Ala Pro Glu His Leu Ser Ala Pro Thr
            20                  25                  30

Leu Pro Leu Pro Glu Val Gln Cys Phe Val Phe Asn Ile Glu Tyr Met
        35                  40                  45

Asn Cys Thr Trp Asn Ser Ser Ser Glu Pro Gln Ala Thr Asn Leu Thr
50                  55                  60

```
Leu His Tyr Arg Tyr Lys Val Ser Asp Asn Asn Thr Phe Gln Glu Cys
 65                  70                  75                  80

Ser His Tyr Leu Phe Ser Lys Glu Ile Thr Ser Gly Cys Gln Ile Gln
                 85                  90                  95

Lys Glu Asp Ile Gln Leu Tyr Gln Thr Phe Val Val Gln Leu Gln Asp
            100                 105                 110

Pro Gln Lys Pro Gln Arg Arg Ala Val Gln Lys Leu Asn Leu Gln Asn
        115                 120                 125

Leu Val Ile Pro Arg Ala Pro Glu Asn Leu Thr Leu Ser Asn Leu Ser
130                 135                 140

Glu Ser Gln Leu Glu Leu Arg Trp Lys Ser Arg His Ile Lys Glu Arg
145                 150                 155                 160

Cys Leu Gln Tyr Leu Val Gln Tyr Arg Ser Asn Arg Asp Arg Ser Trp
                165                 170                 175

Thr Glu Leu Ile Val Asn His Glu Pro Arg Phe Ser Leu Pro Ser Val
            180                 185                 190

Asp Glu Leu Lys Arg Tyr Thr Phe Arg Val Arg Ser Arg Tyr Asn Pro
        195                 200                 205

Ile Cys Gly Ser Ser Gln Gln Trp Ser Lys Trp Ser Gln Pro Val His
    210                 215                 220

Trp Gly Ser His Thr Val Glu Glu Asn Pro Ser Leu Phe Ala Leu Glu
225                 230                 235                 240

Ala

<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 195

His His His His His His
1               5

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 196

His His His His His His His His
1               5

<210> SEQ ID NO 197
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Gly
      Ser" repeating units

<400> SEQUENCE: 197
```

```
Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
                20                  25                  30

Gly Gly Gly Ser Gly Gly Gly Ser
        35                  40

<210> SEQ ID NO 198
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(50)
<223> OTHER INFORMATION: This sequence may encompass 1-10 "Gly Gly Gly
      Ser Gly" repeating units

<400> SEQUENCE: 198

Gly Gly Gly Ser Gly Gly Gly Gly Ser Gly Gly Gly Ser Gly Gly
1               5                   10                  15

Gly Gly Ser Gly Gly Gly Gly Ser Gly Gly Gly Ser Gly Gly Gly
                20                  25                  30

Gly Ser Gly Gly Gly Ser Gly Gly Gly Ser Gly Gly Gly Gly
        35                  40                  45

Ser Gly
    50

<210> SEQ ID NO 199
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-10 "Gly Gly Ser
      Gly" repeating units

<400> SEQUENCE: 199

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
                20                  25                  30

Gly Gly Ser Gly Gly Gly Ser Gly
        35                  40

<210> SEQ ID NO 200
<211> LENGTH: 6
<212> TYPE: PRT
<213> ORGANISM: Artificial Sequence
<220> FEATURE:
<223> OTHER INFORMATION: Description of Artificial Sequence: Synthetic
      His tag
<220> FEATURE:
<221> NAME/KEY: SITE
```

```
<222> LOCATION: (1)..(6)
<223> OTHER INFORMATION: This sequence may encompass 3-6 residues

<400> SEQUENCE: 200

His His His His His His
1               5
```